(12) United States Patent
Koide et al.

(10) Patent No.: US 12,065,409 B2
(45) Date of Patent: Aug. 20, 2024

(54) ANALOGS OF 2-PRALIDOXIME AS ANTIDOTES AGAINST ORGANOPHOSPHORUS NERVE AGENTS

(71) Applicant: University of Pittsburgh—Of the Commonwealth System of Higher Education, Pittsburgh, PA (US)

(72) Inventors: Kazunori Koide, Pittsburgh, PA (US); Kiflai Bein, Mars, PA (US); George D. Leikauf, Gibsonia, PA (US); Robert Kruger Bressin, West Homestead, PA (US); James Proviano Burrows, West Homestead, PA (US); Adriana Gambino, Pittsburgh, PA (US); Dianne Pham, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 800 days.

(21) Appl. No.: 17/058,429

(22) PCT Filed: May 30, 2019

(86) PCT No.: PCT/US2019/034641
§ 371 (c)(1),
(2) Date: Nov. 24, 2020

(87) PCT Pub. No.: WO2020/027905
PCT Pub. Date: Feb. 6, 2020

(65) Prior Publication Data
US 2021/0317084 A1    Oct. 14, 2021

Related U.S. Application Data

(60) Provisional application No. 62/677,813, filed on May 30, 2018.

(51) Int. Cl.
| | | |
|---|---|---|
| *C07D 213/53* | (2006.01) | |
| *A61K 9/00* | (2006.01) | |
| *A61K 45/06* | (2006.01) | |

(52) U.S. Cl.
CPC .......... *C07D 213/53* (2013.01); *A61K 9/0019* (2013.01); *A61K 45/06* (2013.01)

(58) Field of Classification Search
CPC .................................................. C07D 213/53
See application file for complete search history.

(56) References Cited

U.S. PATENT DOCUMENTS

| | | | |
|---|---|---|---|
| 4,352,810 A | 10/1982 | Benschop et al. | |
| 5,726,314 A * | 3/1998 | Powers ................ | C07D 213/65 |
| | | | 546/331 |
| 9,249,100 B2 | 2/2016 | Quinn et al. | |
| 2007/0093518 A1 | 4/2007 | Wetherell et al. | |
| 2016/0244741 A1 | 8/2016 | Russell et al. | |

OTHER PUBLICATIONS

Bravo et al (2005) : STN International, CAPLUS database, Accession No. 2005 : 592428.*
Malovana et al (2002) : STN International, CAPLUS database, Accession No. 2002 : 555067.*
Acharya et al., "In vitro reactivation of sarin-inhibited human acetylcholinesterase (AChE) by bis-pyridinium oximes connected by xylene linkers," Toxicology in Vitro, 2011, pp. 251-256, vol. 25.
Comba et al., "Tuning of the Properties of Transition-Metal Bispidine Complexes by Variation of the Basicity of the Aromatic Donor Groups," Inorganic Chemistry, 2013, pp. 6481-6501, vol. 52(11).
Demar et al., "Pro-2-PAM therapy for central and peripheral cholinesterases," Chemico-Biological Interactions, 2010, pp. 191-198, vol. 187.
Ekstrom et al., "Novel Nerve-Agent Antidote Design Based on Crystallographic and Mass Spectrometric Analyses of Tabun-Conjugated Acetylcholinesterase in Complex with Antidotes," Clinical Pharmacology & Therapeutics, 2007, pp. 282-292.
"Executive Summary," National Research Council, "Guidelines for Chemical Warfare Agents in Military Field Drinking Water," 1995, pp. 1-12.
Hornberg et al., "Crystal structures of oxime-bound fenamiphos-acetylcholinesterases: Reactivation involving flipping of the His447 ring to form a reactive Glu334-His447-oxime triad," Biochemical Pharmacology, 2010, pp. 507-515, vol. 79.
Kuca et al., "Chemical warfare agents," Molecular, Clinical, and Environmental Toxicology, 2010, p. 543, vol. 2.
Limnios et al., "2,2,2,-Trifluoroacetophenone as an Organocatalyst for the Oxidation of Tertiary Amines and Azines to N-Oxides," Chemistry (A European Journal), 2014, pp. 559-563, vol. 20.
Lorke et al., "Entry of Oximes into the Brain: A Review," Current Medicinal Chemistry, 2008, pp. 743-753, vol. 15.
Mercey et al., "Reactivators of Acetylcholinesterase Inhibited by Organophosphorus Nerve Agents," Accounts of Chemical Research, 2012, pp. 756-766, vol. 45(5).
"1-Methylpyridinium-2-aldoxime Chloride," PubChem, 2005, pp. 1-19.
Sakurada et al., "Pralidoxime Iodide (2-PAM) Penetrates across the Blood-Brain Barrier," Neurochemical Research, 2003, pp. 1401-1407, vol. 28(9).
Tanga et al., "Syntheses of Five Potential Heterocyclic Amine Food Mutagens," J. Heterocycl. Chem, 1997, pp. 117-127, vol. 34(3).
Remington: The Science and Practice of Pharmacy, Troy et al., editors, 21st edition, 2005, chapters 37, 39, 41, 42, and 45, Lippincott, Williams & Wilkins, Baltimore, MD.

* cited by examiner

*Primary Examiner* — Golam M Shameem
(74) *Attorney, Agent, or Firm* — The Webb Law Firm

(57) ABSTRACT

Provided herein are compounds useful in treating exposure to an organophosphorus compound, such as a nerve agent, pesticide, or, generally, an acetylcholinesterase inhibitor, such as sarin. Compositions, e.g. pharmaceutical compositions or dosage forms, comprising the compounds also are provided herein. Methods of treating a patient exposed to a nerve agent, pesticide, or, generally, an acetylcholinesterase inhibitor, e.g., an organophosphorus compound, such as sarin, also are provided.

12 Claims, 61 Drawing Sheets

1H NMR spectrum of (E)-2-((hydroxyimino)methyl)-1,4-dimethylpyridin-1-ium iodide (ADG2078, 400 MHz, DMSO-d6, 293K).

13C NMR spectrum of (E)-2-((hydroxyimino)methyl)-1,4-dimethylpyridin-1-ium iodide (ADG2078, 100 MHz, DMSO-d6, 293K).

$^{13}$C NMR spectrum of (E)-2-((hydroxyimino)methyl)-1-methyl-4-(propylthio)pyridin-1-ium iodide (ADG2293, 100 MHz, 293 K, DMSO-d$_6$).

13C NMR spectrum of (E)-4-(butylthio)-2-{(hydroxyimino)methyl}-1-methylpyridin-1-ium iodide (ADG2294, 100 MHz, 293 K, DMSO-d6).

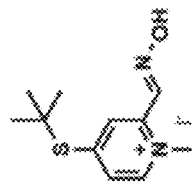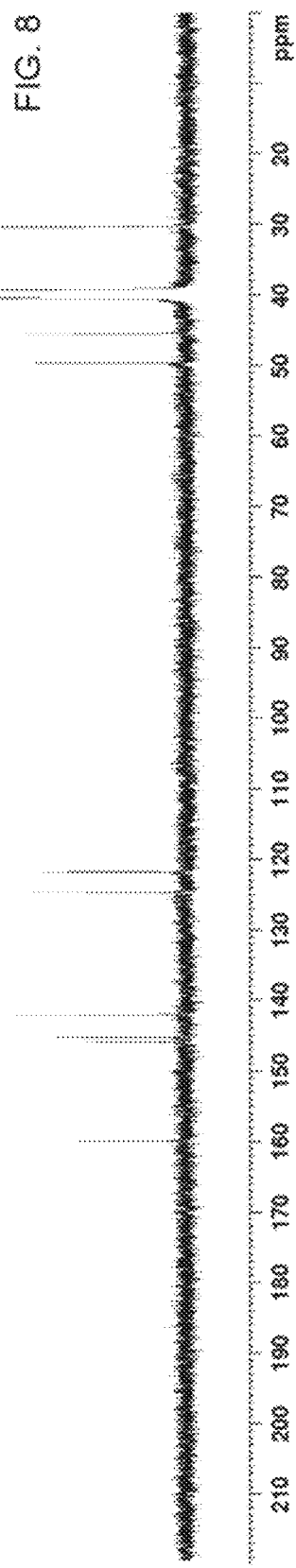
FIG. 8

1H NMR spectrum of (E)-2-((hydroxyimino)methyl)-1-methyl-4-(phenylthio)pyridin-1-ium iodide) (ADG3002, 400 MHz, 293 K, DMSO-d6)

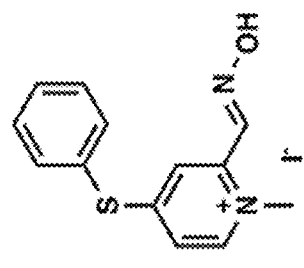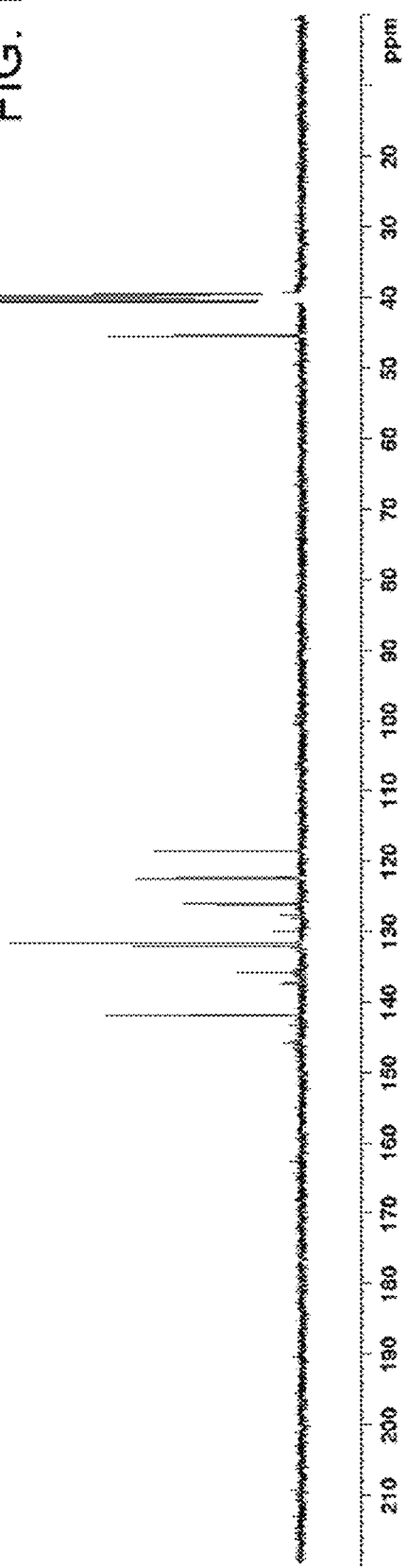
FIG. 10
13C NMR spectrum of (E)-2-((hydroxyimino)methyl)-1-methyl-4-(phenylthio)pyridin-1-ium iodide) (ADG3002, 100 MHz, 293 K, DMSO-d6)

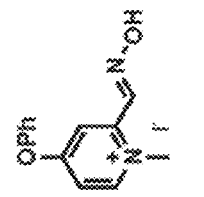
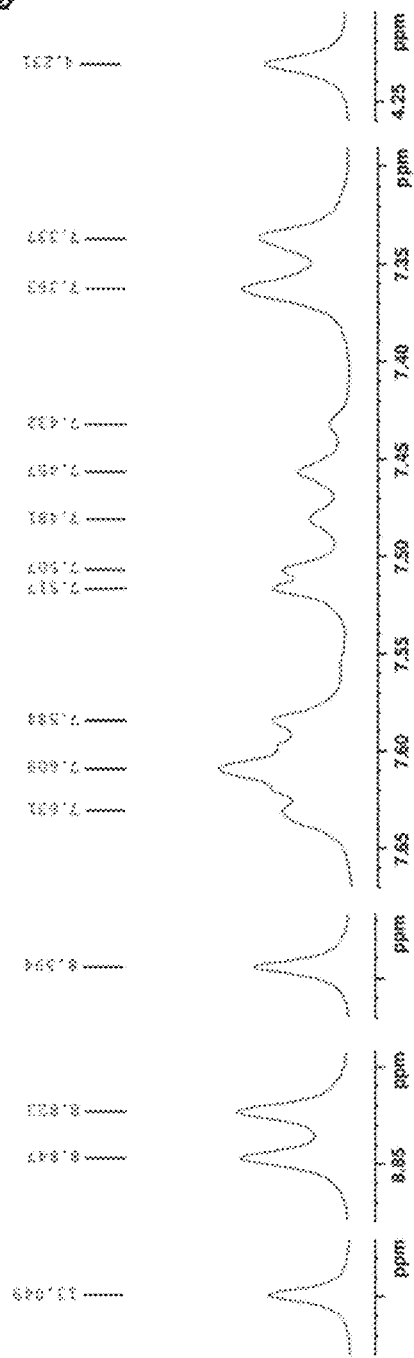
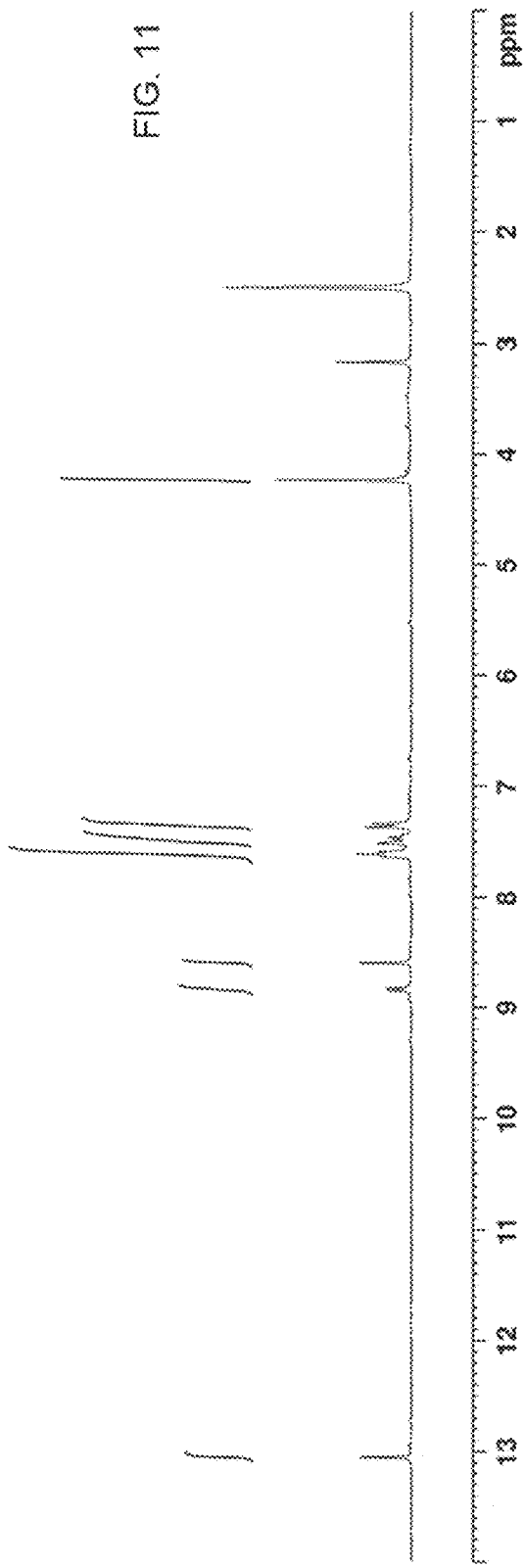
FIG. 11

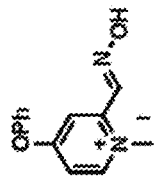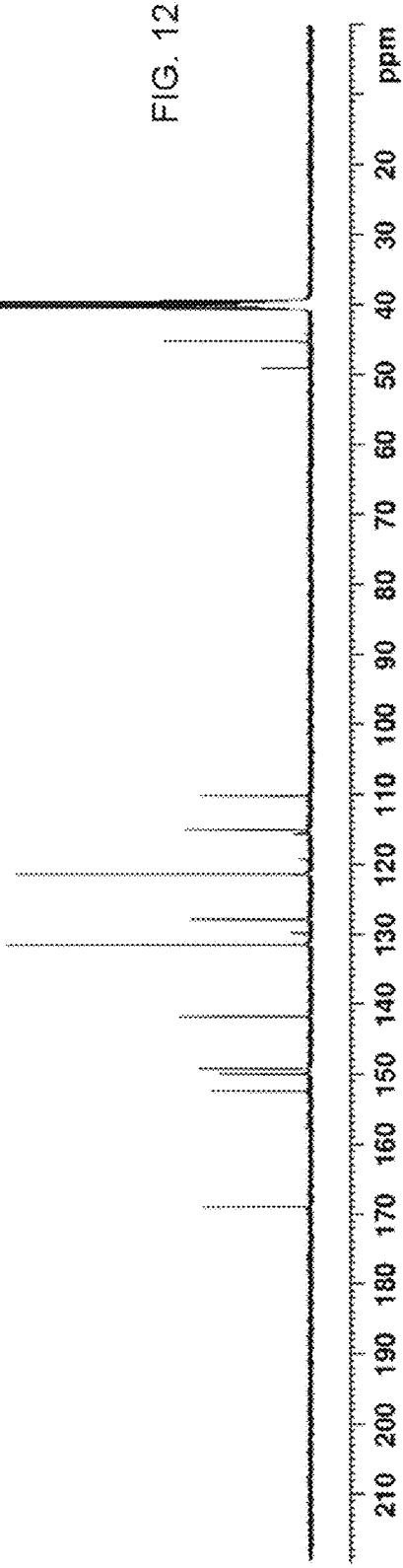
FIG. 12
13C NMR spectrum of (E)-2-((hydroxyimino)methyl)-1-methyl-4-phenoxypyridin-1-ium iodide (ADG303, 100 MHz, 293 K, DMSO-d6).

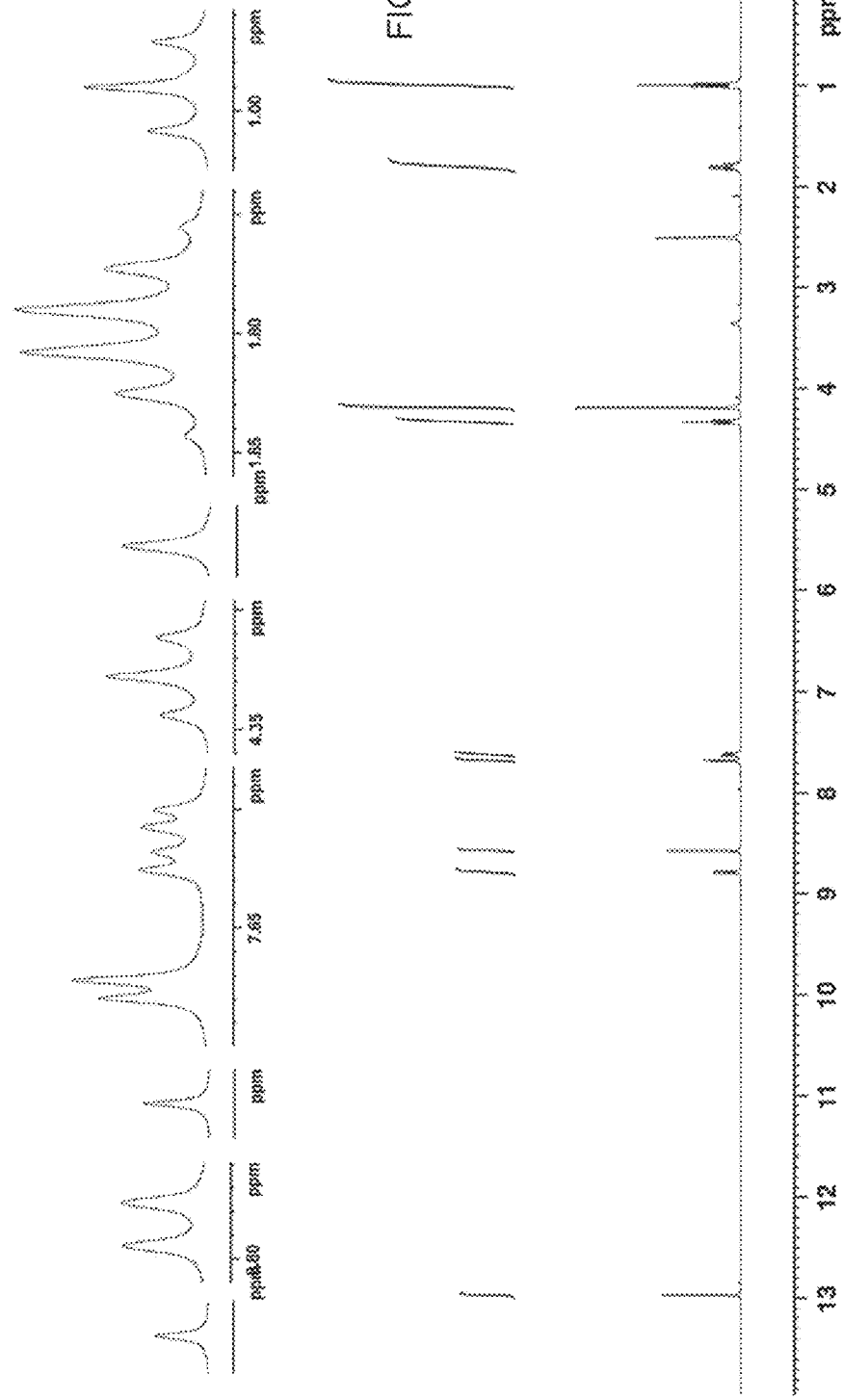
FIG. 13

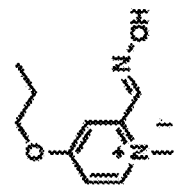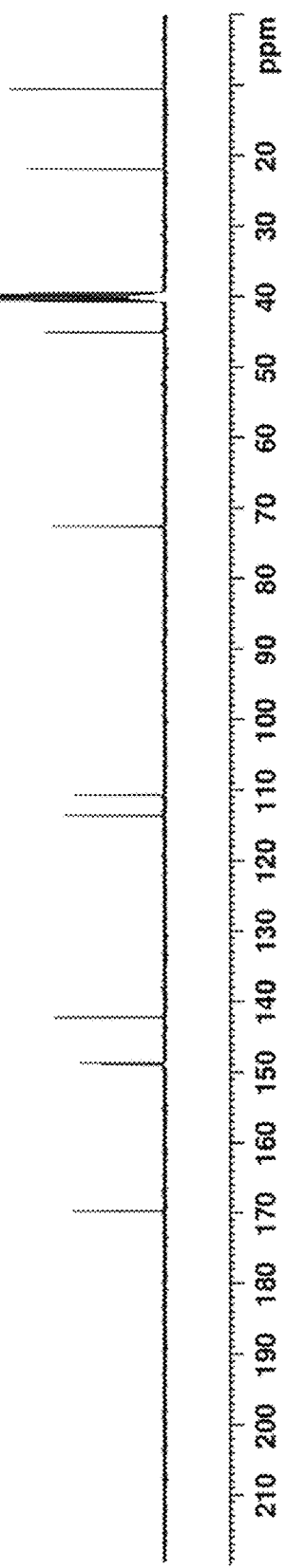
FIG. 14
13C NMR spectrum of (E)-2-((hydroxyimino)methyl)-1-methyl-4-propoxypyridin-1-ium iodide (ADG3035, 100 MHz, 293 K, DMSO-d6).

13C NMR spectrum of (E)-2-((hydroxyimino)methyl)-4-(isopropylthio)-1-methylpyridin-1-ium iodide (ADG3060, 100 MHz, 293 K, DMSO-d6)

13C NMR spectrum of (E)-2-((hydroxyimino)methyl)-1-methyl-4-(p-tolyloxy)pyridin-1-ium iodide (ADG3092, 100 MHz, 293 K, DMSO-d6).

$^{13}C$ NMR spectrum of (E)-2-((hydroxyimino)methyl)-1-methyl-4-(o-tolyloxy)pyridin-1-ium iodide (ADG3110, 100 MHz, 293 K, DMSO-$d_6$).

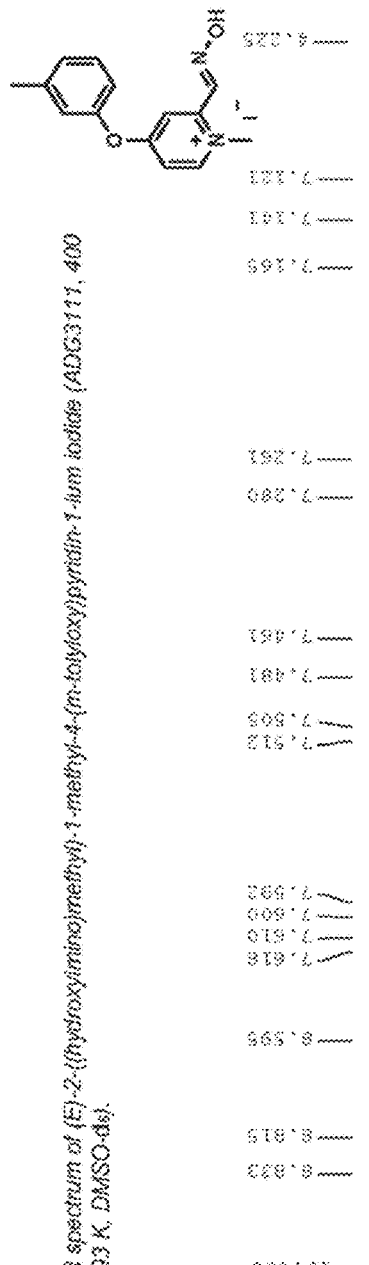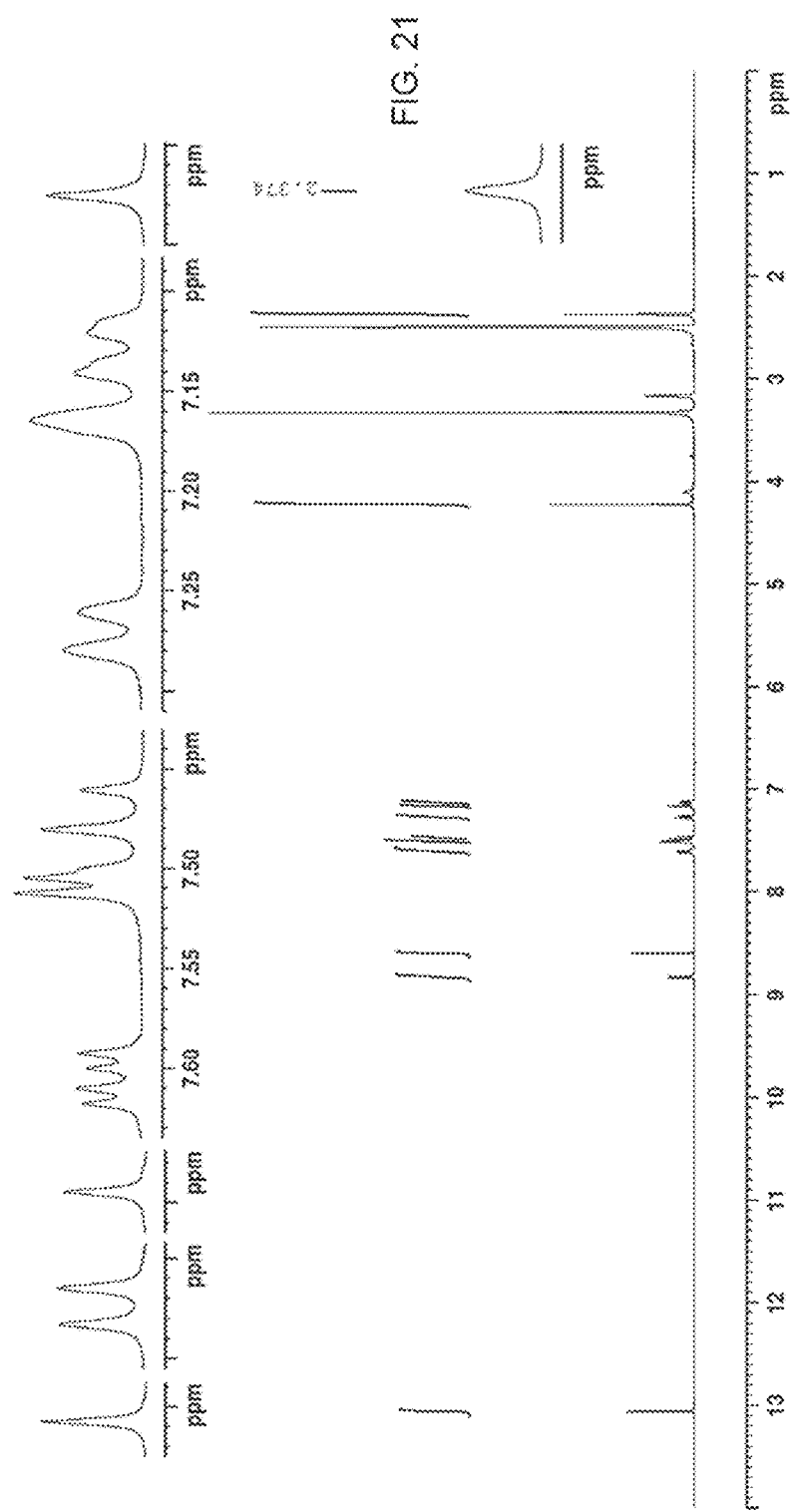
FIG. 21

13C NMR spectrum of (E)-2-((hydroxyimino)methyl)-1-methyl-4-(m-tolyloxy)pyridin-1-ium iodide (ADG3111, 100 MHz, 293 K, DMSO-$d_6$).

$^{13}$C NMR spectrum of (E)-2-((hydroxyimino)methyl)-1-methyl-4-(4-fluorophenoxy)pyridin-1-ium iodide (ADG3116, 100 MHz, 293 K, DMSO-$d_6$).

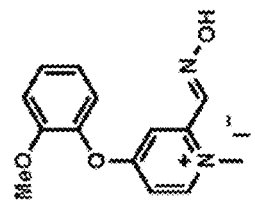
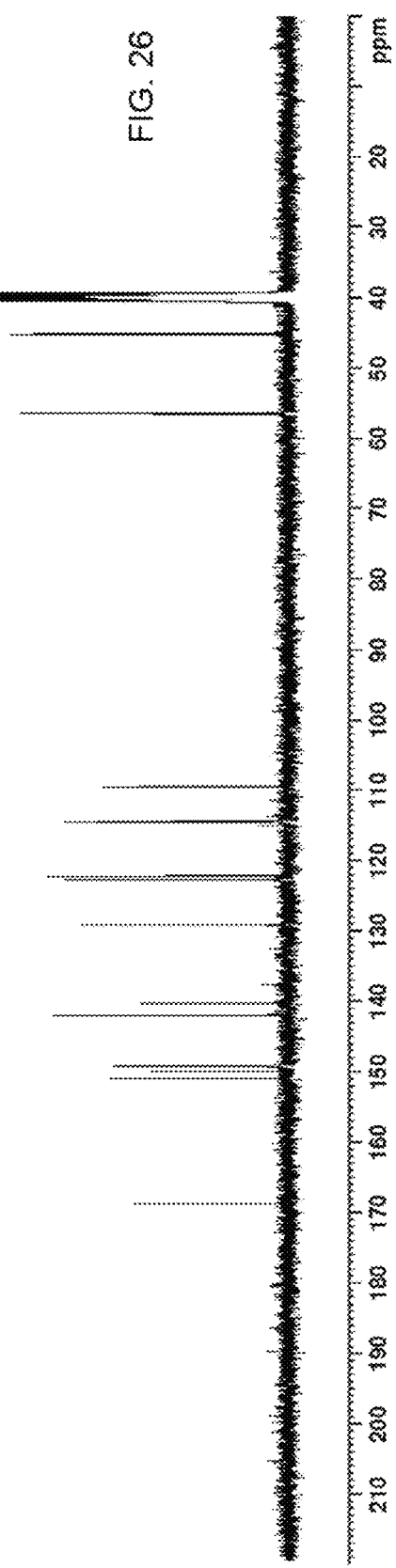
FIG. 26
13C NMR spectrum of (E)-2-((hydroxyimino)methyl)-1-methyl-4-(2-methoxyphenoxy)pyridin-1-ium iodide (ADG3120, 100 MHz, 293 K, DMSO-d6).

$^1$H NMR spectrum of (E)-2-((hydroxyimino)methyl)-1-methyl-4-(4-methoxyphenoxy)pyridin-1-ium iodide (ADG3121, 400 MHz, 293 K, DMSO-d$_6$).

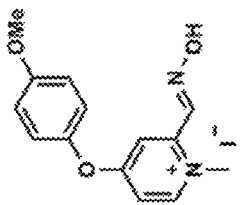
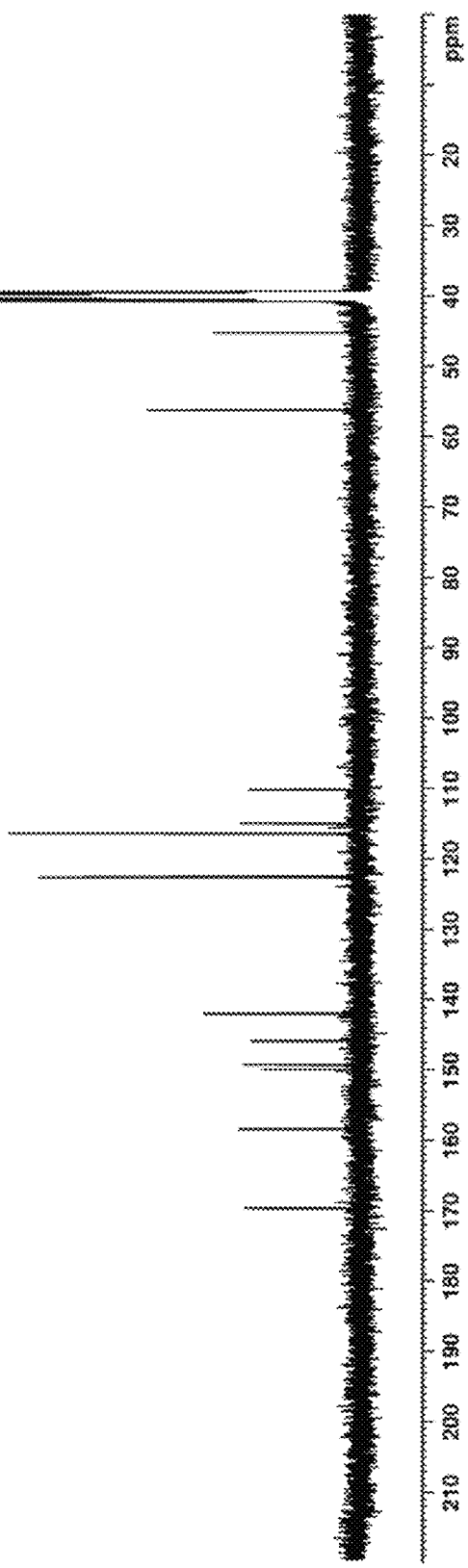
FIG. 28
$^{13}C$ NMR spectrum of (E)-2-((hydroxyimino)methyl)-1-methyl-4-(4-methoxyphenoxy)pyridin-1-ium iodide (ADG3121, 100 MHz, 293 K, DMSO-$d_6$).

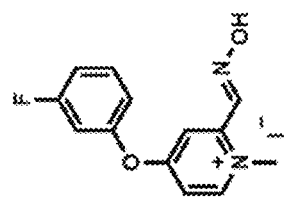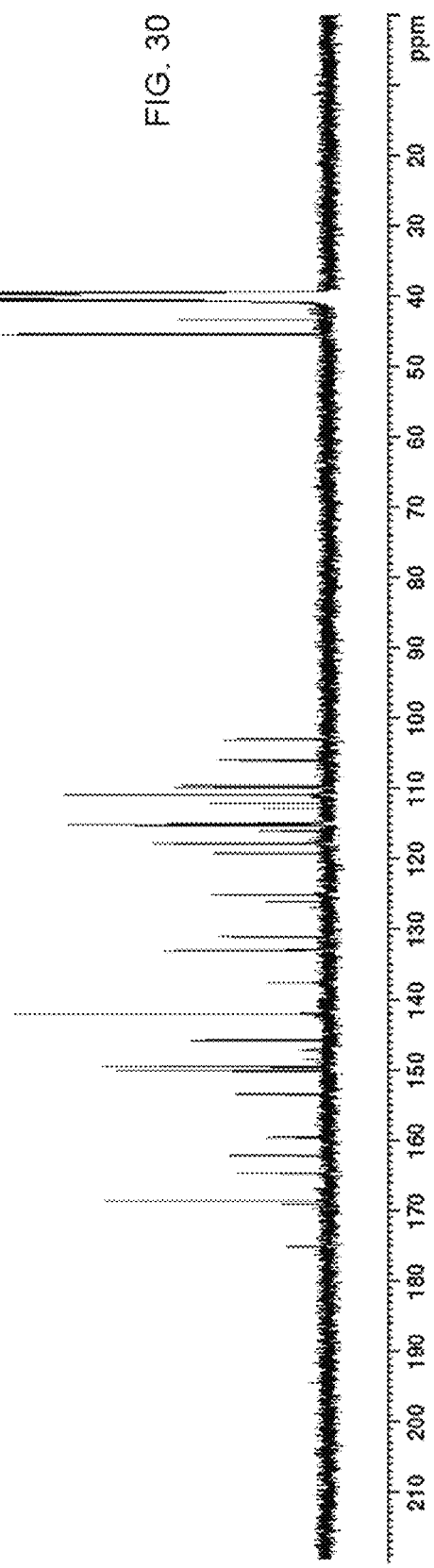
FIG. 30
13C NMR spectrum of (E)-2-((hydroxyimino)methyl)-1-methyl-4-(3-fluorophenoxy)pyridin-1-ium iodide (ADG3123, 100 MHz, 293 K, DMSO-d6).

$^1$H NMR spectrum of (E)-2-(hydroxyimino)methyl)-1-methyl-4-(3-methoxyphenoxy)pyridin-1-ium iodide (ADG7128, 400 MHz, 293 K, DMSO-d6).

13C NMR spectrum of (E)-2-((hydroxyimino)methyl)-1-methyl-4-(3-methoxyphenoxy)pyridin-1-ium iodide (ADG3128, 100 MHz, 293 K, DMSO-$d_6$).

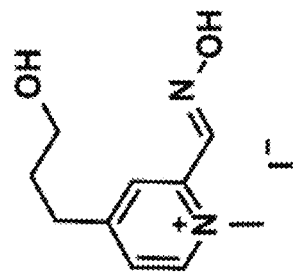
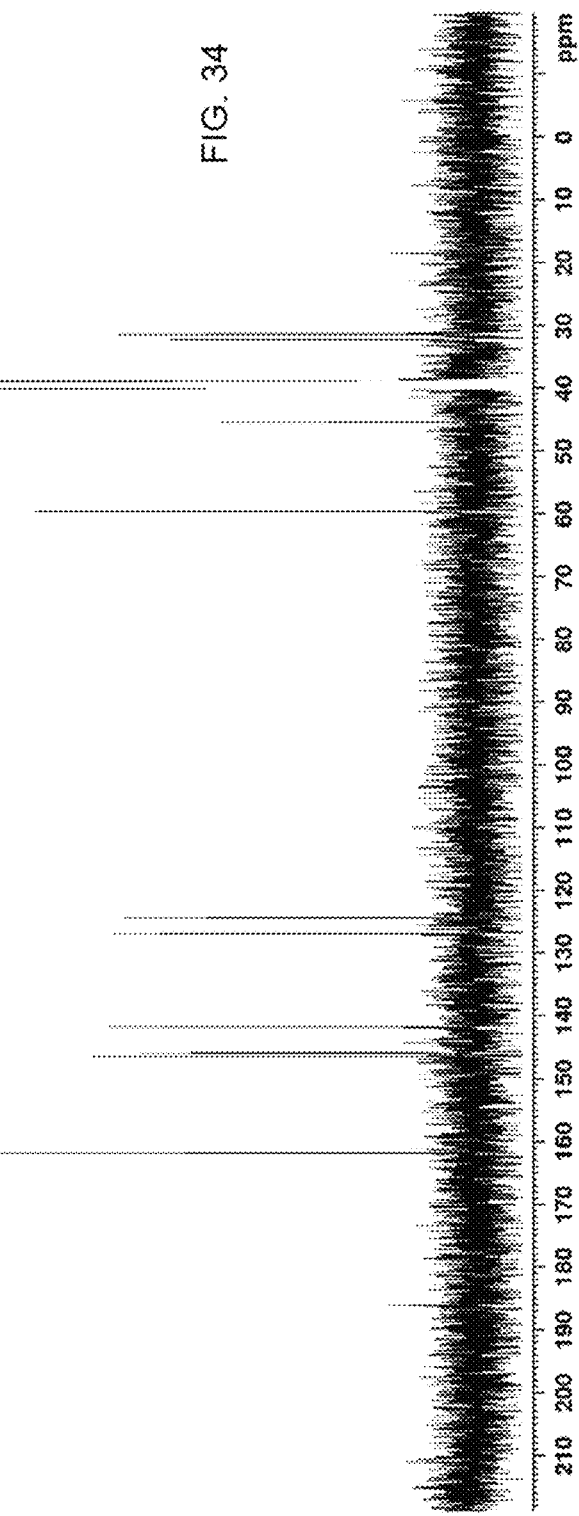
FIG. 34
13C NMR spectrum of (E)-2-((hydroxyimino)methyl)-4-(3-hydroxypropyl)-1-methylpyridin-1-ium iodide (RKB6186, 100 MHz, DMSO-d6, 293K)

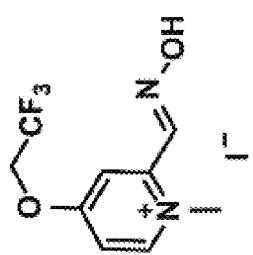
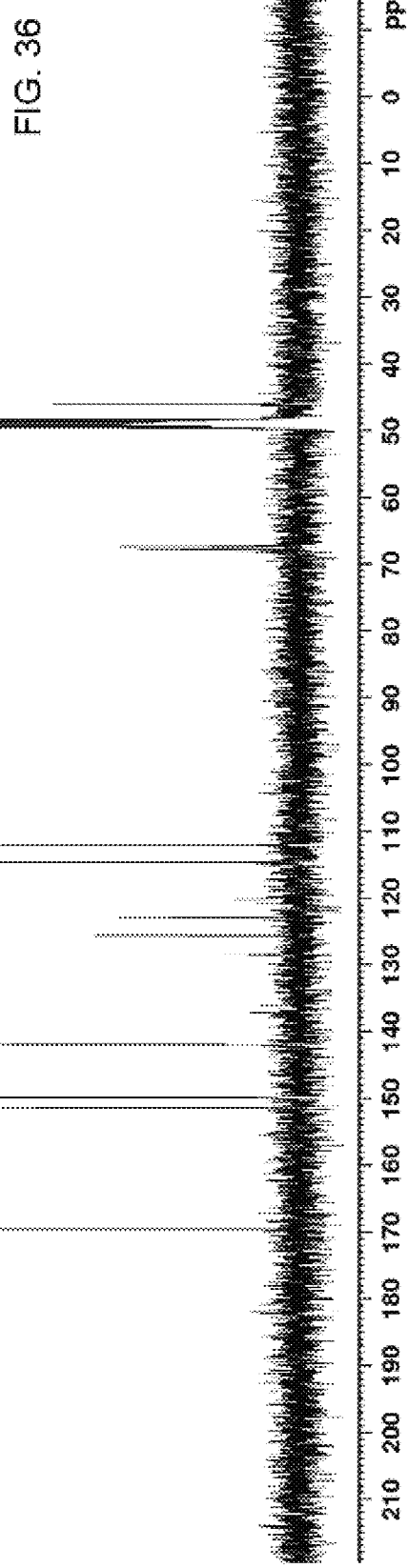
FIG. 36
13C NMR spectrum of (E)-2-((hydroxyimino)methyl)-1-methyl-4-(2,2,2-trifluoroethoxy)pyridin-1-ium iodide (RKB6220, 100 MHz, CD₃OD, 293K)

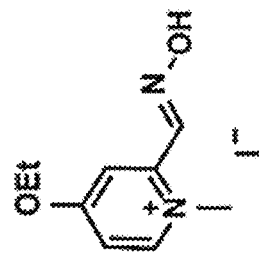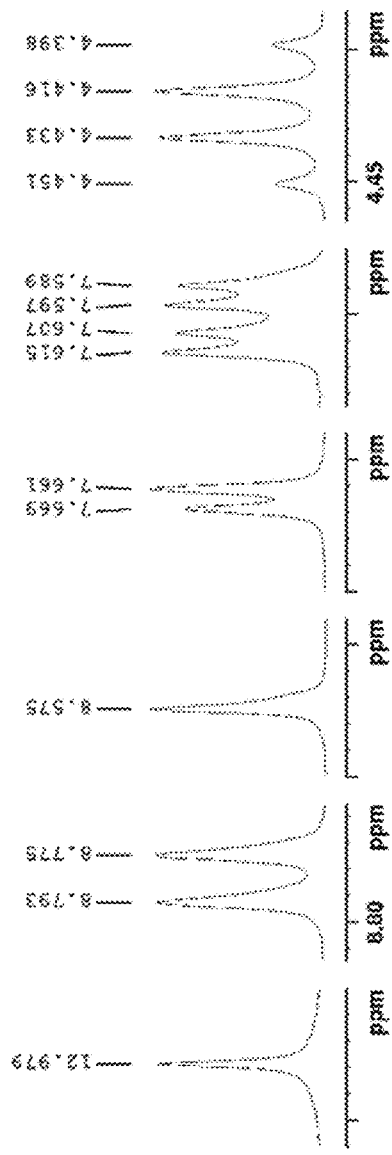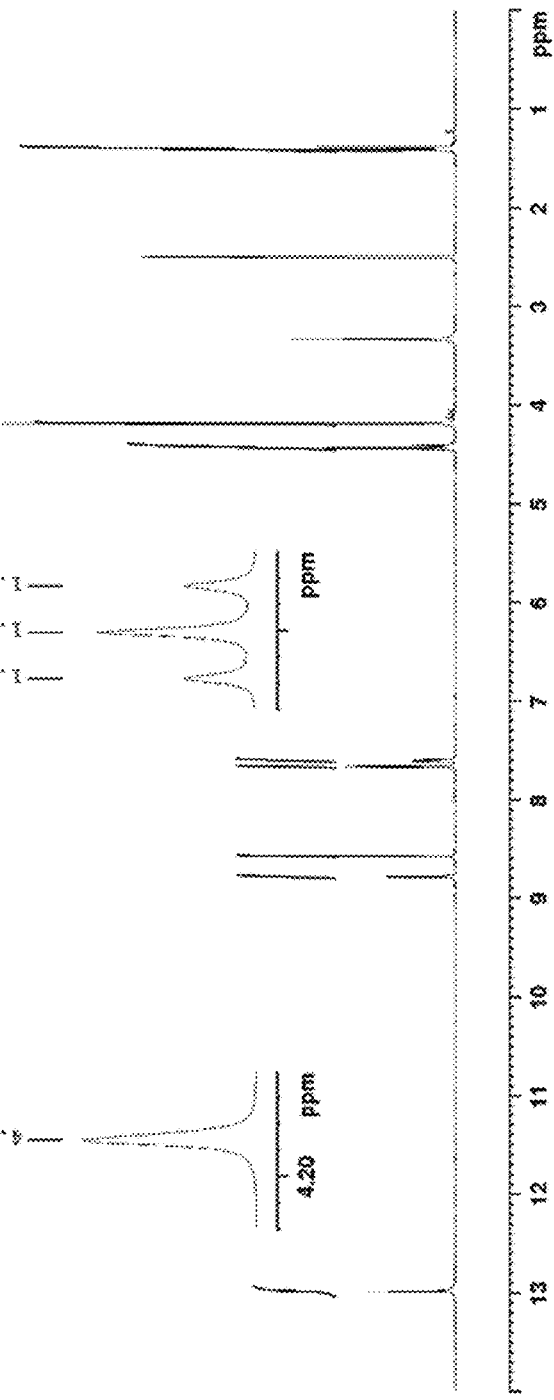
FIG. 37

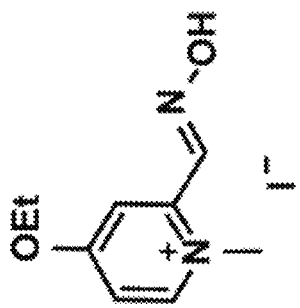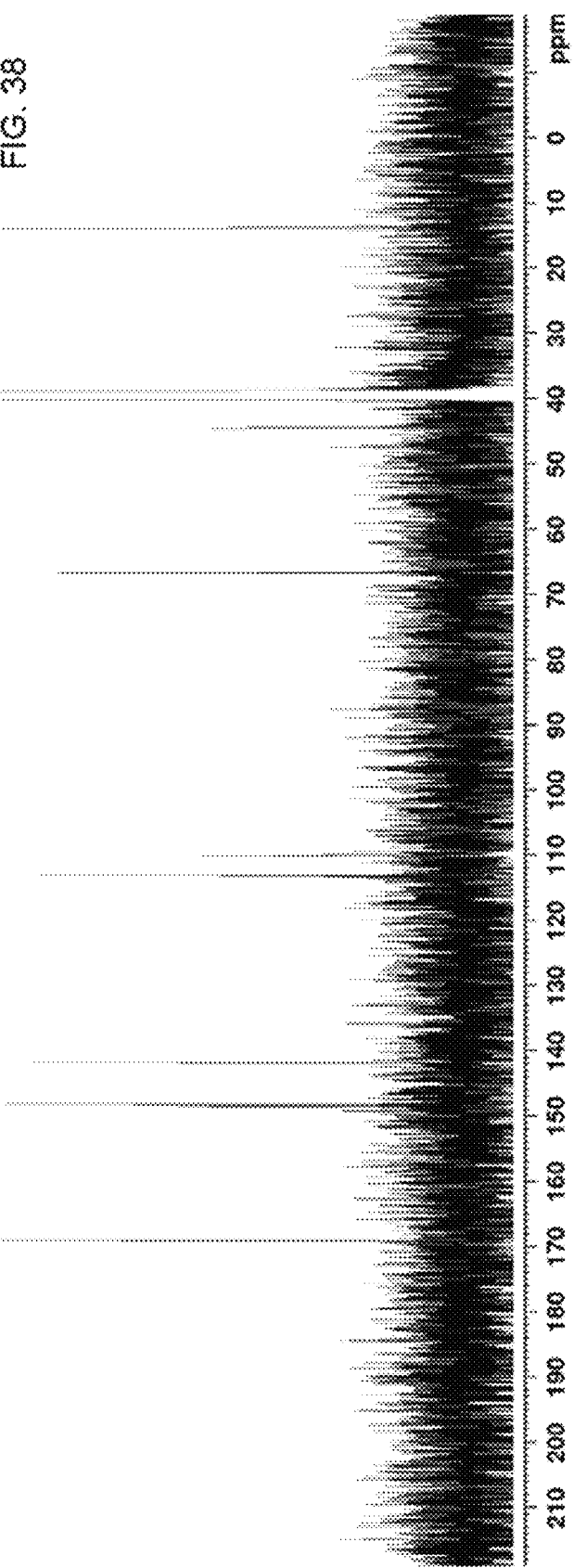
FIG. 38
13C NMR spectrum of (E)-4-ethoxy-2-((hydroxyimino)methyl)-1-methylpyridin-1-ium iodide (RxKB6229, 100 MHz, DMSO-d6, 293K)

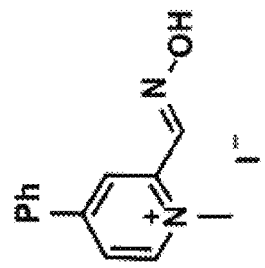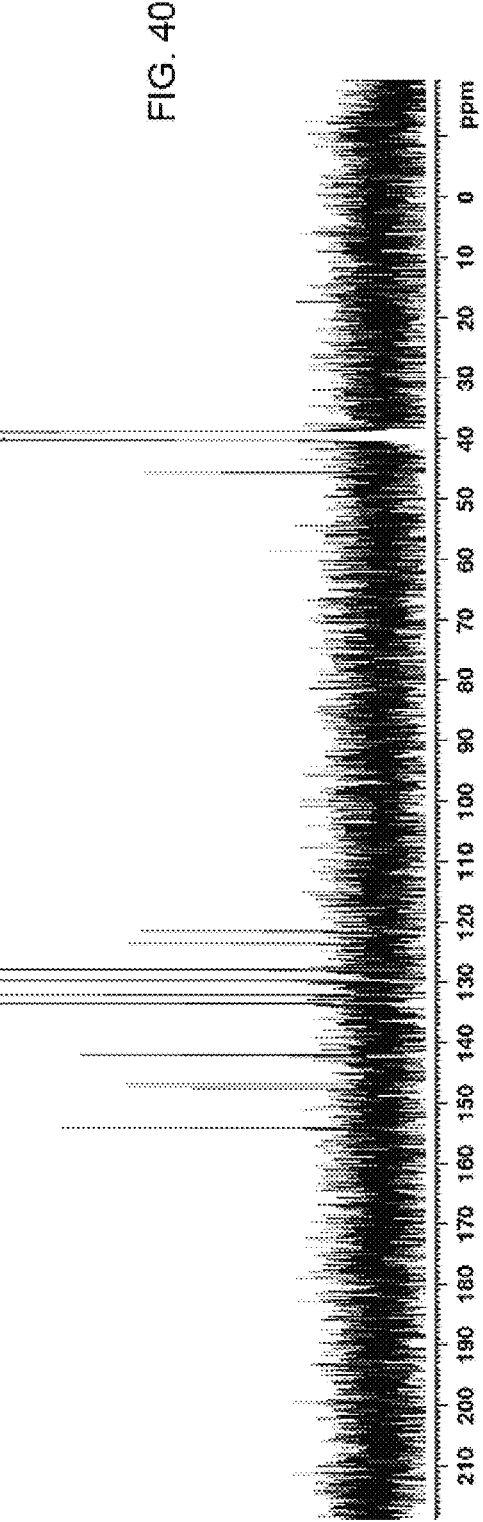
FIG. 40
13C NMR spectrum of (E)-2-((hydroxyimino)methyl)-1-methyl-4-phenylpyridin-1-ium iodide (RKB6242, 100 MHz, DMSO-$d_6$, 293K)

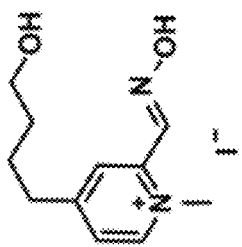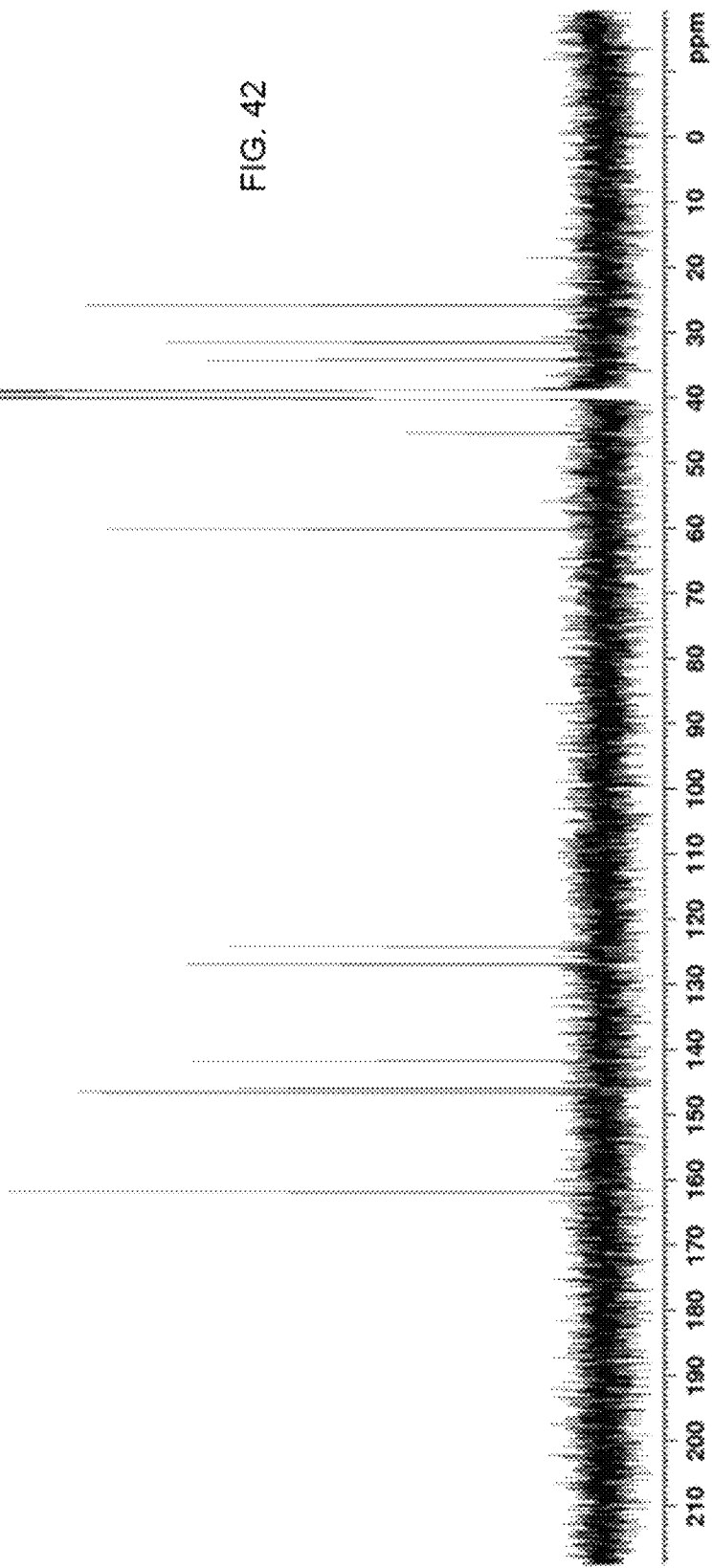
FIG. 42
$^{13}C$ NMR spectrum of (E)-4-(4-hydroxybutyl)-2-((hydroxyimino)methyl)-1-methylpyridin-1-ium iodide (RKB6259, 100 MHz, DMSO-$d_6$, 293K)

13C NMR spectrum of (E)-2-((hydroxyimino)methyl)-1-methyl-4-(prop-2-yn-1-yloxy)pyridin-1-ium iodide (RKB6284, 100 MHz, DMSO-d6, 293K)

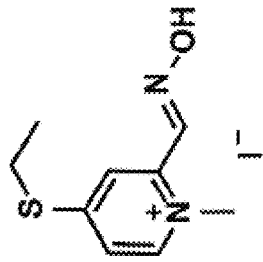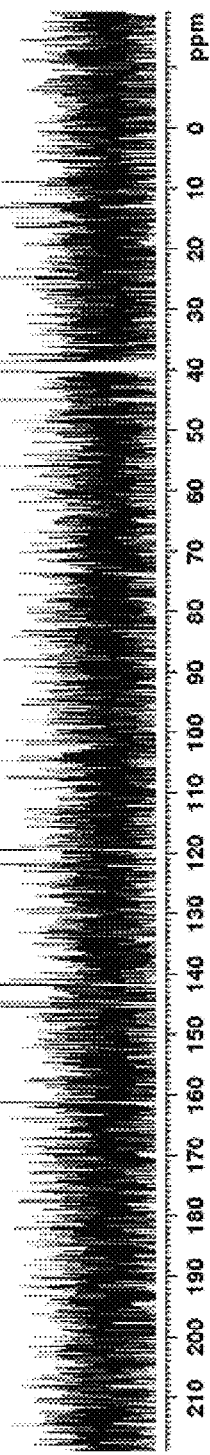
FIG. 46
13C NMR spectrum of (E)-4-(ethylthio)-2-((hydroxyimino)methyl)-1-methylpyridin-1-ium iodide (RKB7070, 100 MHz, DMSO-$d_6$, 293K)

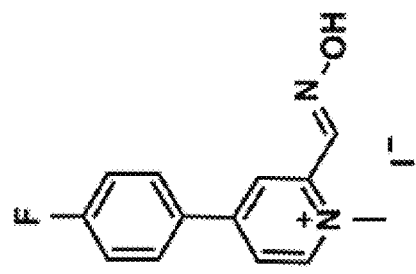
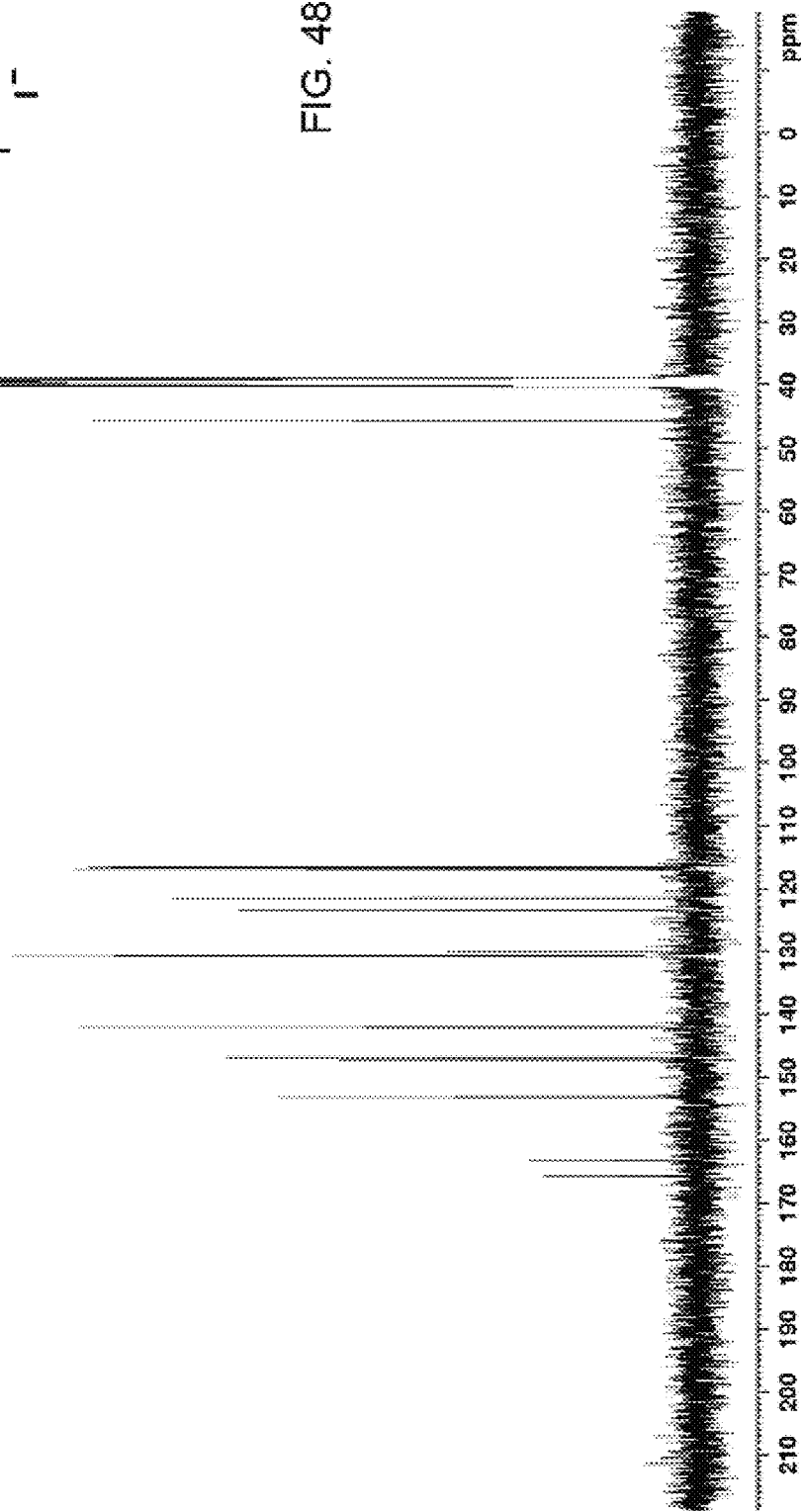
FIG. 48
13C NMR spectrum of (E)-4-(4-fluorophenyl)-2-((hydroxyimino)methyl)-1-methylpyridin-1-ium (RKB8122, 100 MHz, DMSO-$d_6$, 293K)

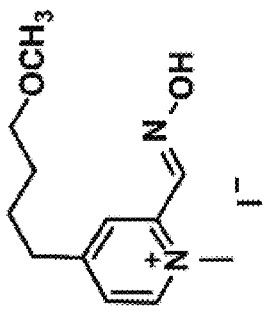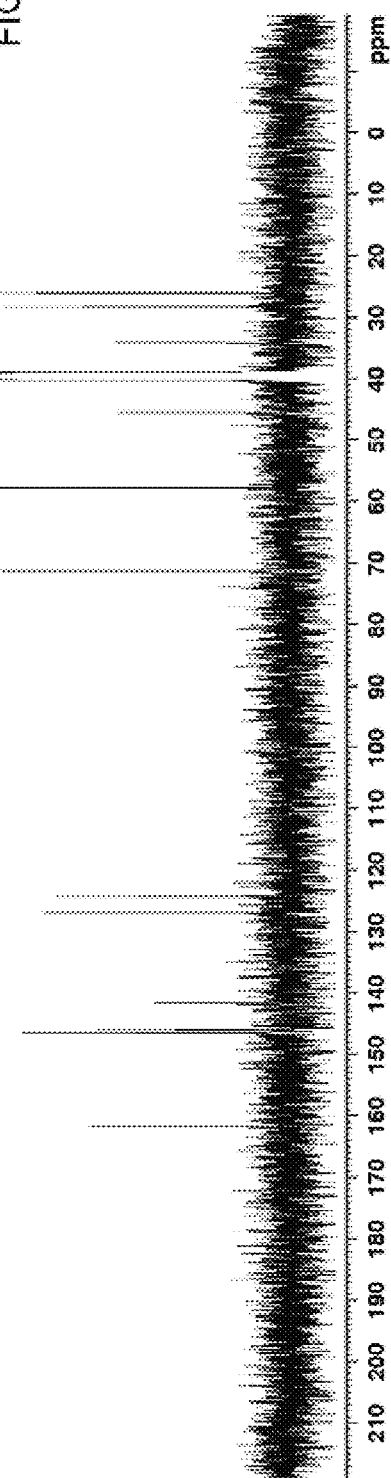
FIG. 50
13C NMR spectrum of (E)-2-((hydroxyimino)methyl)-4-(4-methoxybutyl)-1-methylpyridin-1-ium iodide (RKB8160, 100 MHz, DMSO-d6, 293K)

13C NMR spectrum of (E)-2-((hydroxyimino)methyl)-4-(2-methoxyphenyl)-1-methylpyridin-1-ium iodide (RKB8218, 100 MHz, DMSO-d6, 293K)

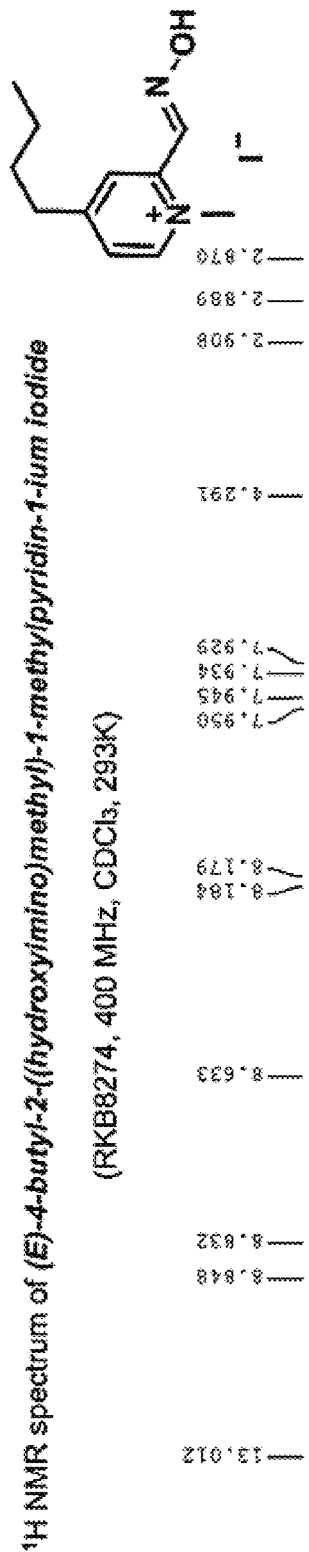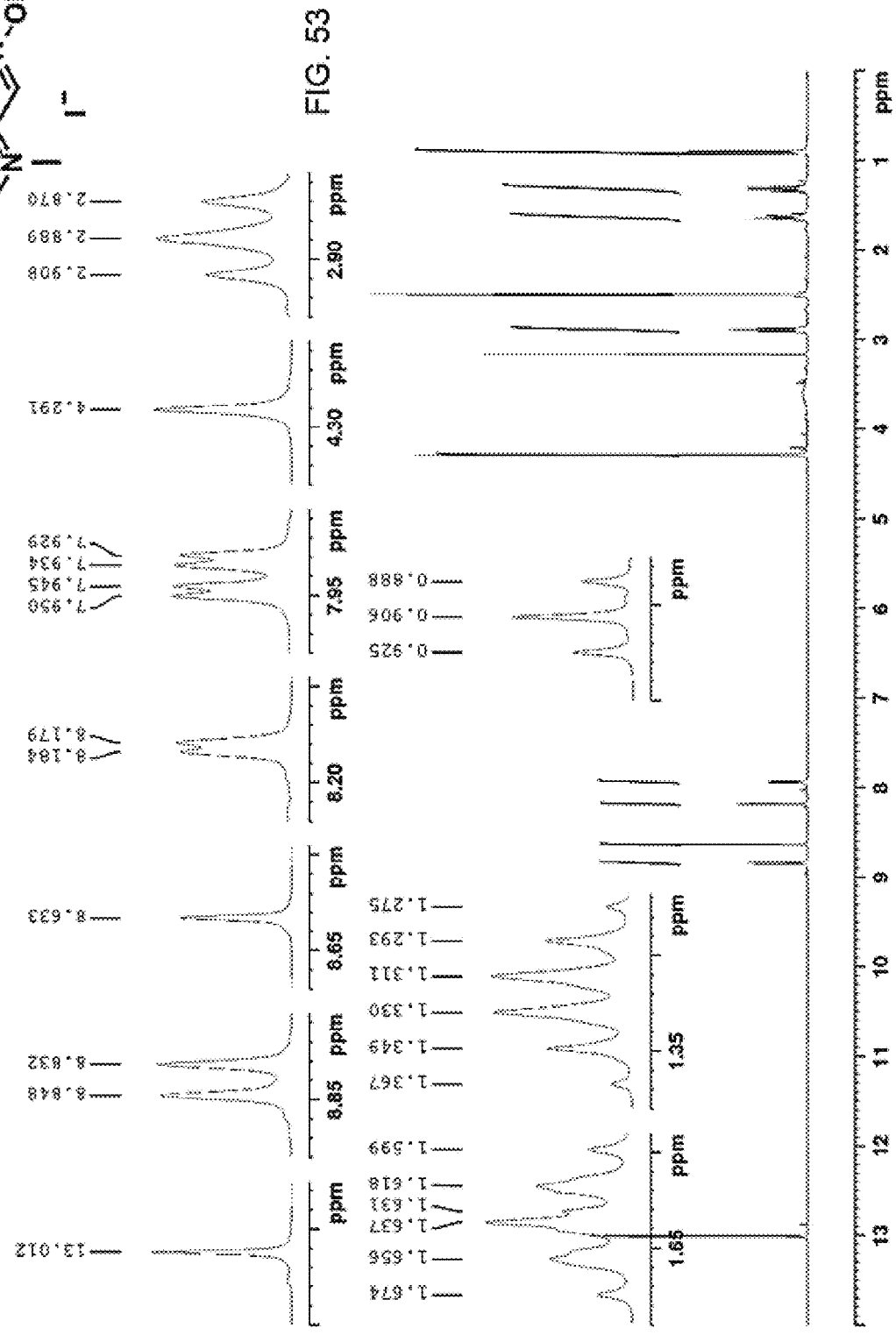
FIG. 53
$^1$H NMR spectrum of (E)-4-butyl-2-((hydroxyimino)methyl)-1-methylpyridin-1-ium iodide (RKB8274, 400 MHz, CDCl$_3$, 293K)

13C NMR spectrum of (E)-4-butyl-2-{(hydroxyimino)methyl}-1-methylpyridin-1-ium iodide (RKB8274, 100 MHz, CDCl3, 293K)

ANALOGS OF 2-PRALIDOXIME AS ANTIDOTES AGAINST ORGANOPHOSPHORUS NERVE AGENTS

CROSS REFERENCE TO RELATED APPLICATIONS

This application is the United States national phase of International Application No. PCT/US2019/034641 filed May 30, 2019, and claims benefit of U.S. Provisional Patent Application No. 62/677,813, filed May 30, 2018, the disclosures of which are hereby incorporated by reference in their entirety.

STATEMENT REGARDING FEDERAL FUNDING

This invention was made with government support under Grant No. HDTRA1-16-1-0041, awarded by the Department of Defense/Defense Threat Reduction Agency. The government has certain rights in the invention.

Provided herein are antidotes against organophosphorus nerve agents, and methods of treating a patient exposed to an organophosphorus nerve agent.

Acetylcholinesterase (AChE) catalyzes the hydrolysis of the neurotransmitter acetylcholine. Its activity can be permanently inhibited by organophosphorus nerve agents (OPNAs) that phosphylate the active serine residue. OPNAs are some of the most toxic synthetic substances, with subcutaneous $LD_{50}$s ranging from 20-165 μg/kg for soman, 43-158 μg/kg for sarin, and 28 μg/kg for VX in small laboratory animals. The use of these chemical weapons is a major public health and safety concern because inhibition of AChE can lead to a toxic accumulation of acetylcholine in nerve synapses. This results in the over stimulation of cholinergic receptors, which can cause seizures, respiratory arrest, and death.

Several small molecules have been developed to reactivate the inhibited enzyme. Current reactivators contain a pyridinium moiety, which engages in associative cation-pi interactions with aromatic amino acids lining the enzyme's active site. Favorable, yet transient, binding interactions results in an increase in activity. While the positive charge is necessary for binding and reactivation, it prevents these compounds from crossing the blood brain barrier (BBB) and limits the bioavailability. The concentration of 2-pralidoxime (2-PAM), the current clinically used antidote in the United States, within the brain only reaches 4-10% of the blood plasma level, so reactivation is limited to the peripheral nervous system.

There is a need for compounds that are useful antidotes against organophosphorus nerve agent that also cross the blood-brain barrier.

SUMMARY

According to one aspect of the invention, provided herein is a compound having the structure:

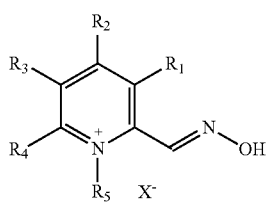

wherein:
$R_1$ and $R_3$ are H; $R_4$ is H or methyl
$R_2$ is H; methyl; phenyl, halomethyl;

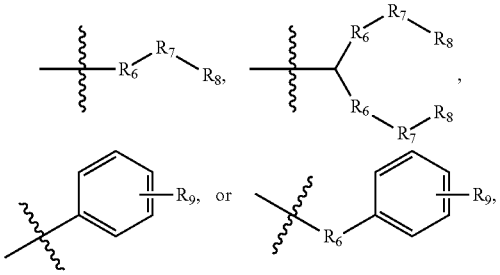

wherein each instance of $R_6$ is, independently, C, O, S, N, carbonyl, sulfinyl, or sulfonyl, each instance of $R_7$ is, independently, a $C_1$-$C_4$ saturated alkane, each instance of $R_8$ is, independently, H, hydroxyl, halo, halomethyl, phenyl, alkoxyl, amine, carboxyl, N($C_1$-$C_4$ alkyl)$_2$, NH($C_1$-$C_4$ alkyl), or azide, and $R_9$ is H, halo, methoxyl, methyl; prop-2-yn-1-yloxyl; 4-hydroxybut-1-yn-1-yl; 3-hydroxyprop-1-yn-1-yl; or phenylethynyl;
$R_5$ is methyl or 3-hydroxypropyl (—$CH_2CH_2CH_2OH$) when $R_2$ and $R_4$ are H; and
$X^-$ is a counterion.

According to another aspect, a composition is provided comprising the above-described compound, and a pharmaceutically-acceptable carrier.

In another aspect of the invention a unit dosage form is provided, comprising a composition comprising the above-described compound, and a pharmaceutically-acceptable carrier.

In a further aspect a method of treating a patient exposed to an organophosphorus compound is provided. The method comprises administering to the patient an amount of the above-described composition or compound effective to treat a patient for exposure to the organophosphorus compound.

DETAILED DESCRIPTION

Figure 1:
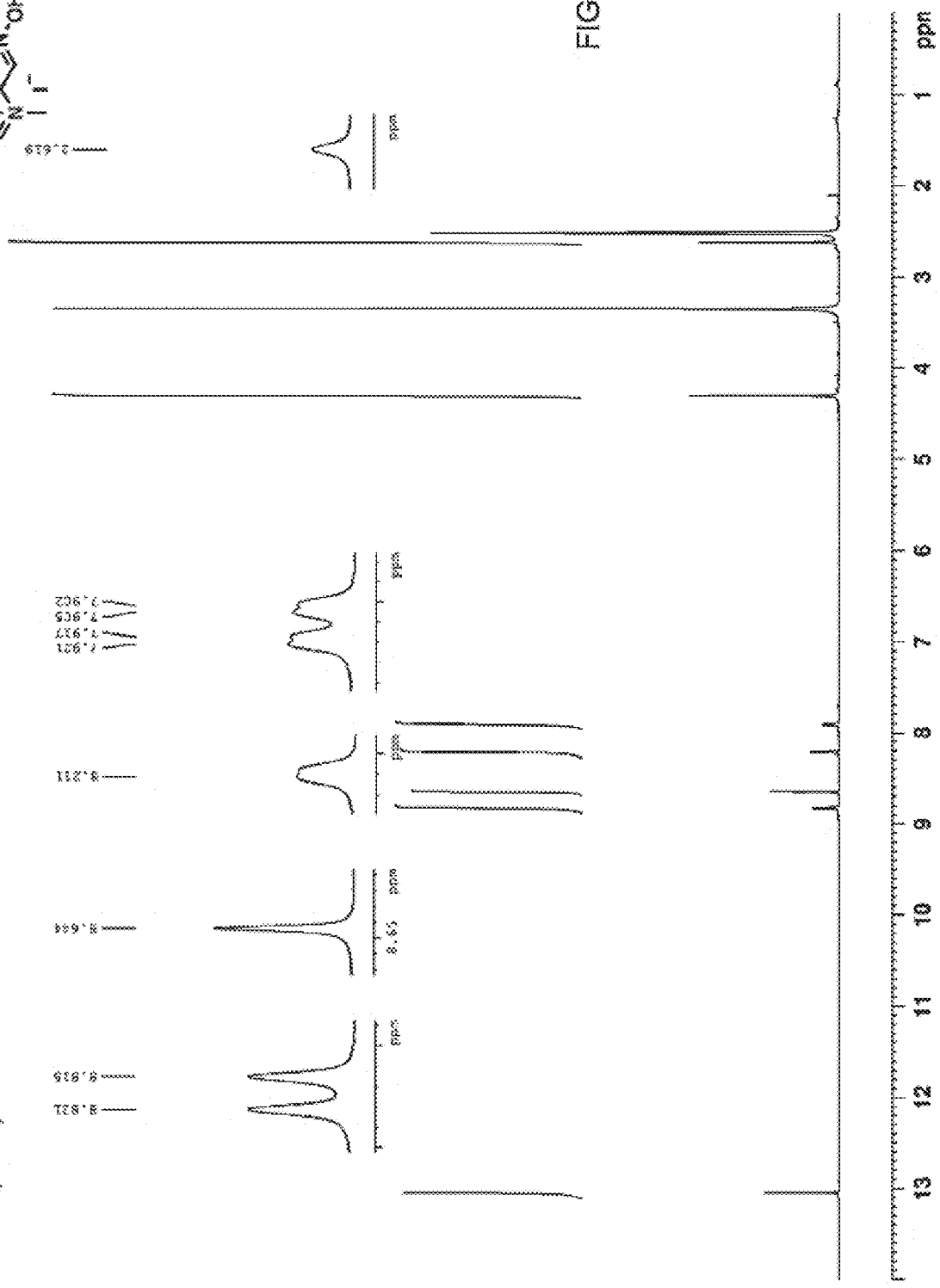
FIGS. 1-54 provide $^1$H and/or $^{13}$C NMR spectra for selected compounds described herein, as indicated.
Figure 2:
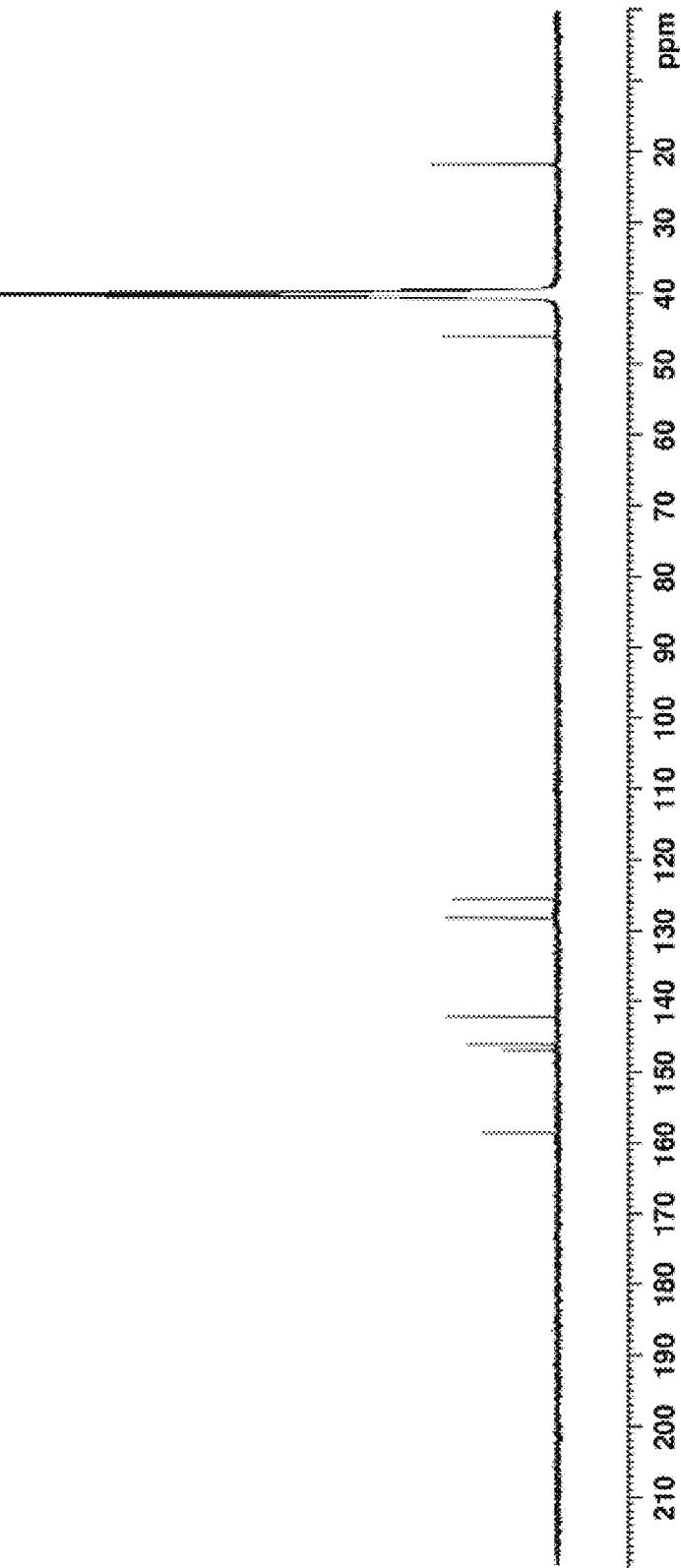
Figure 3:
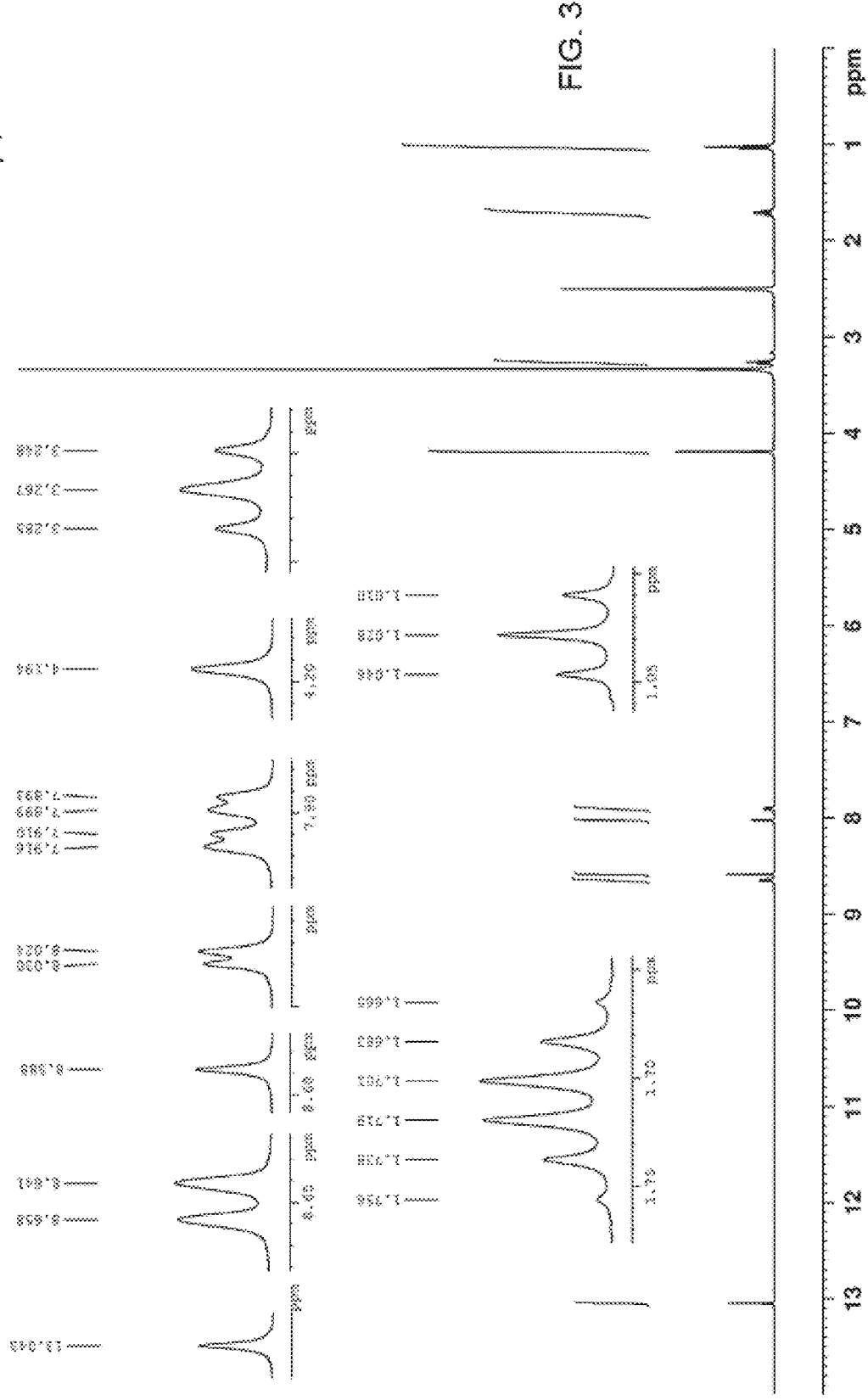
Figure 4:
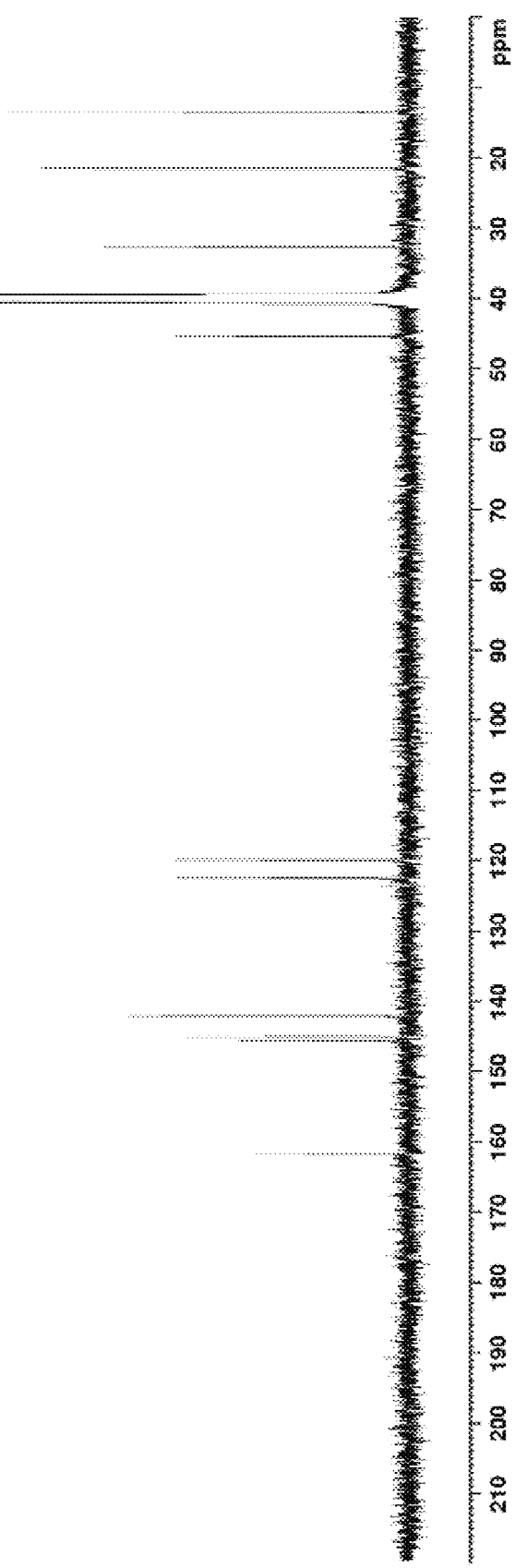
Figure 5:
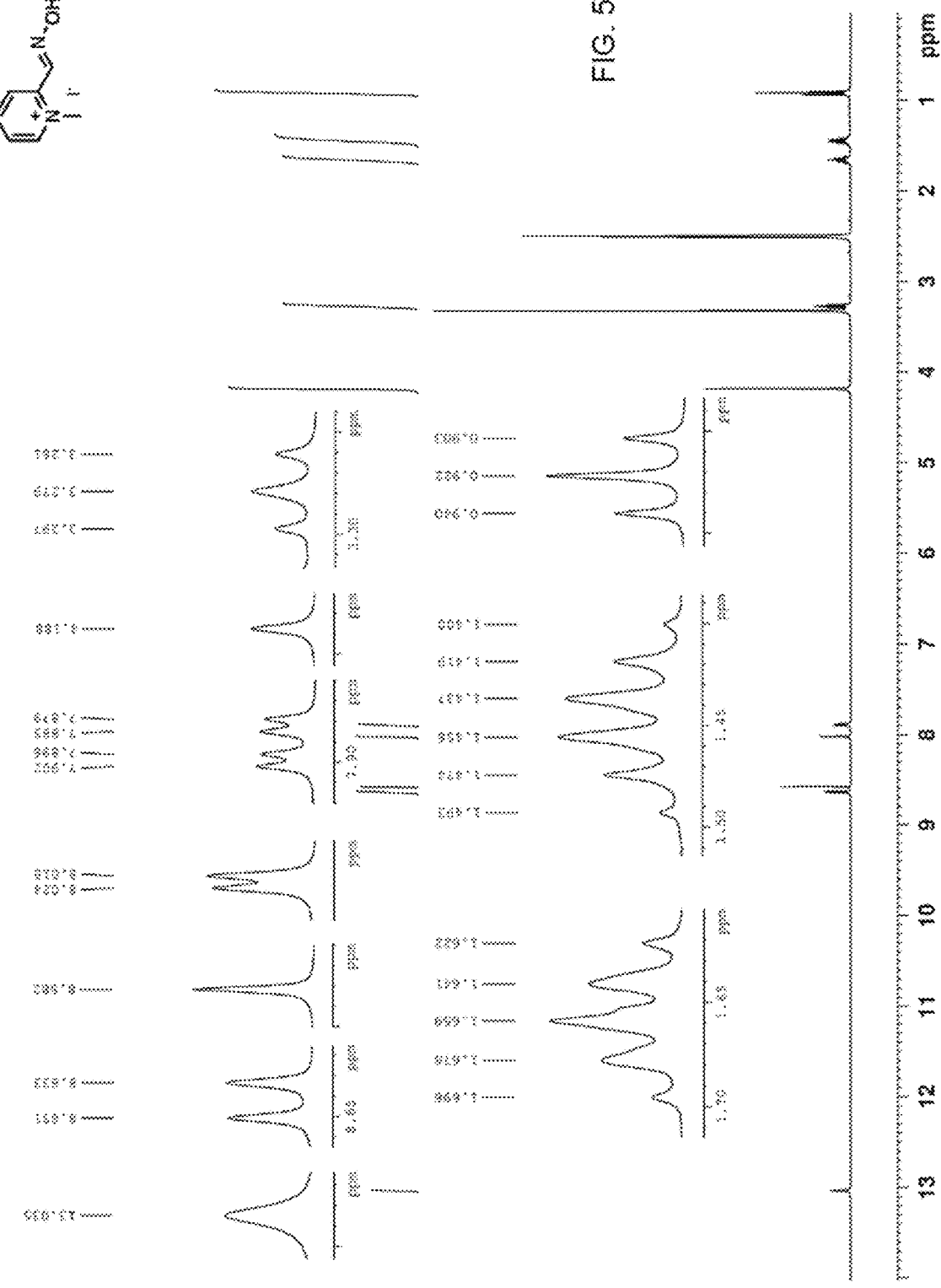
Figure 6:
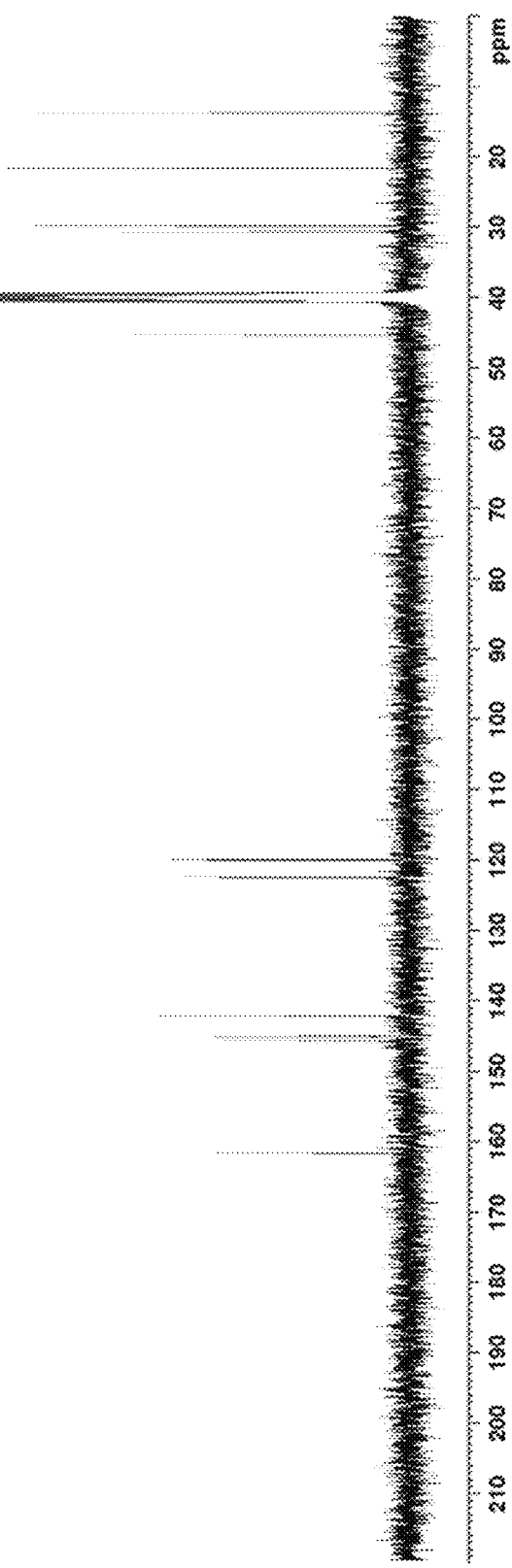
Figure 7:
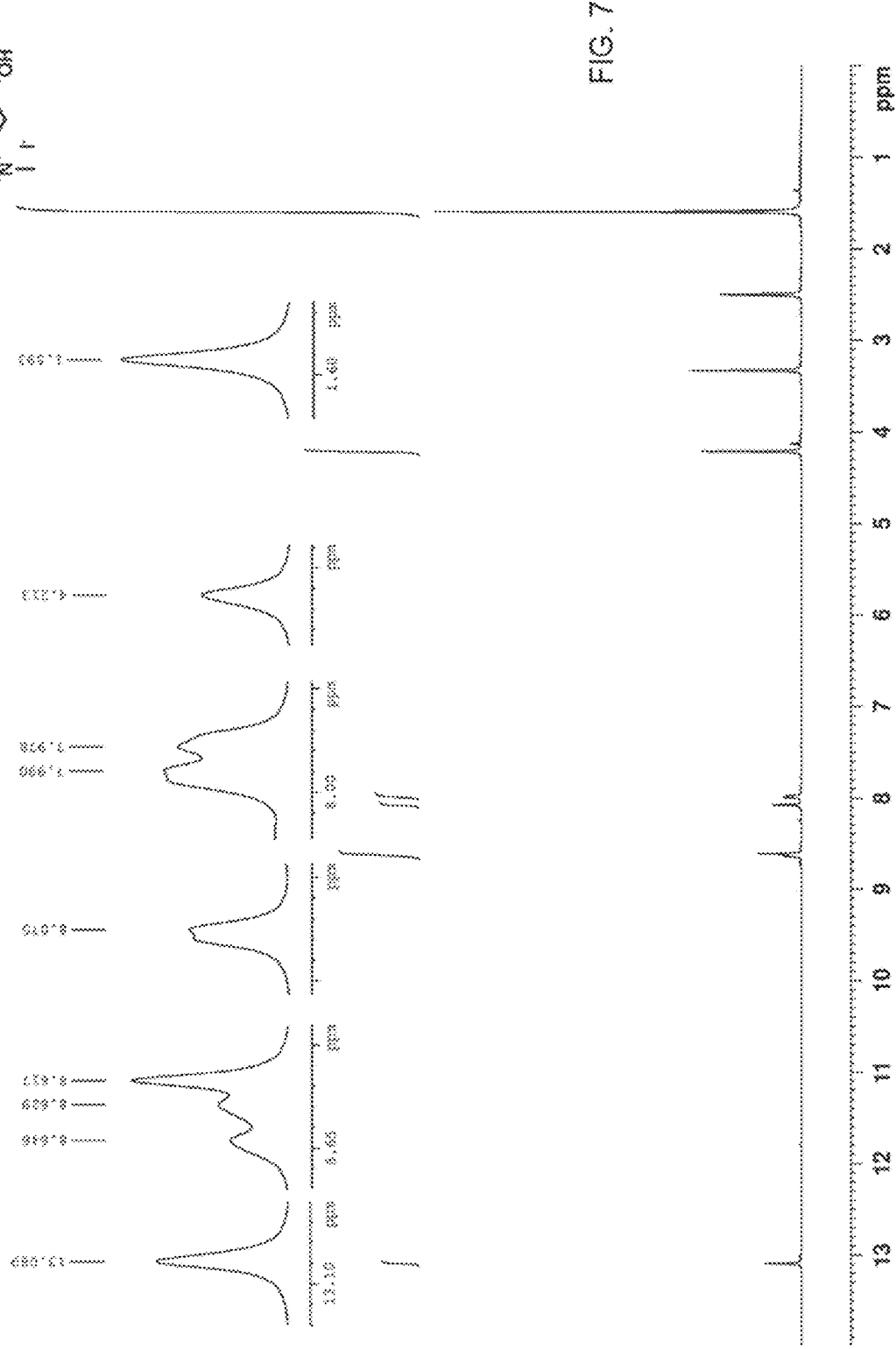
Figure 9:
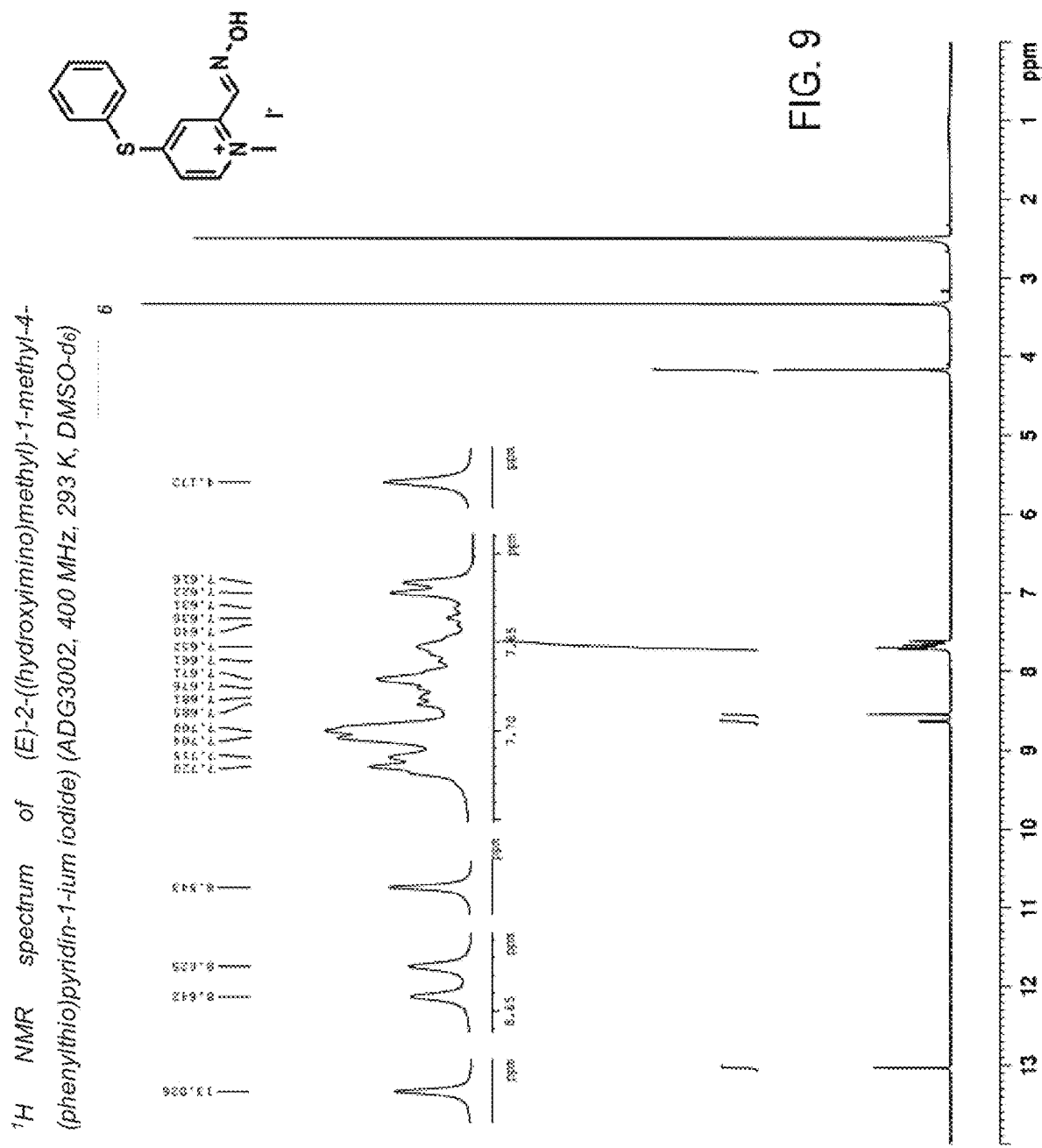
Figure 15:
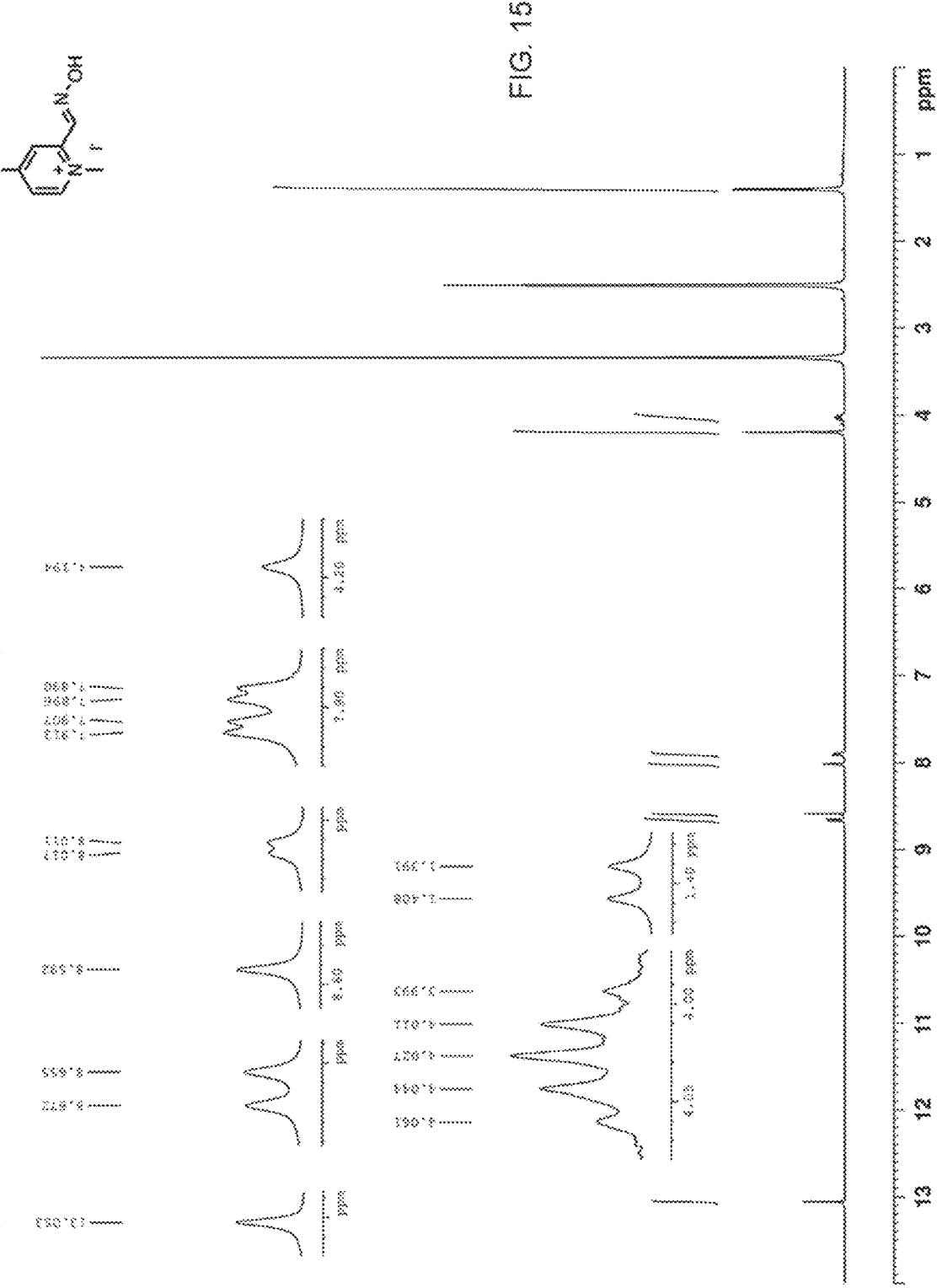
Figure 16:
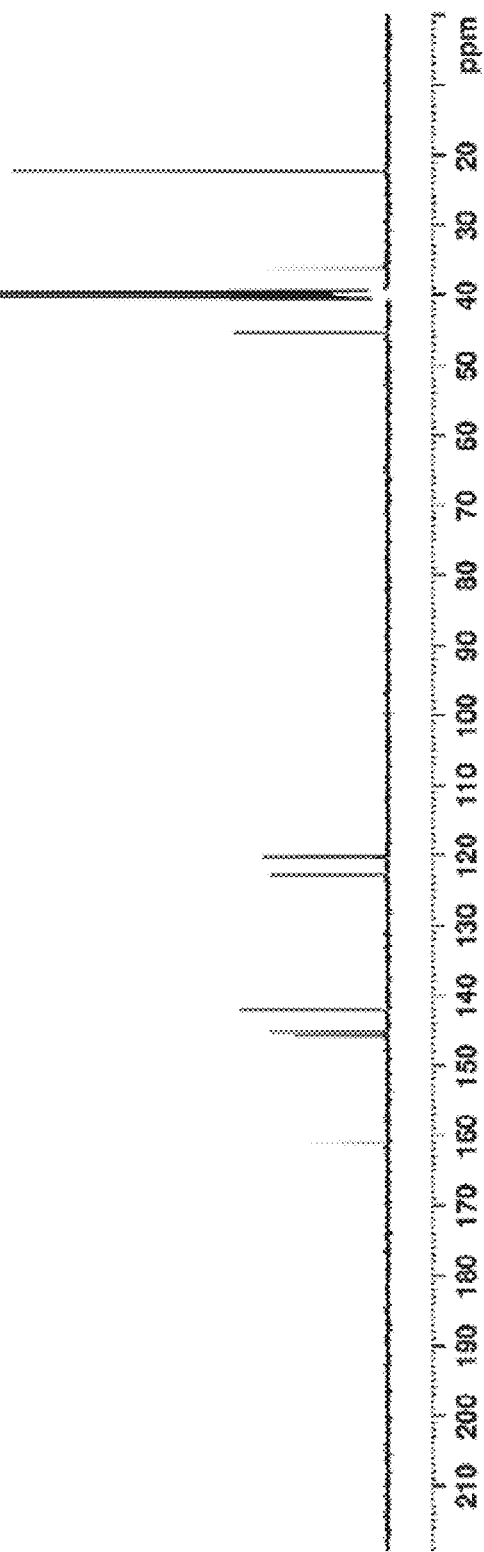
Figure 17:
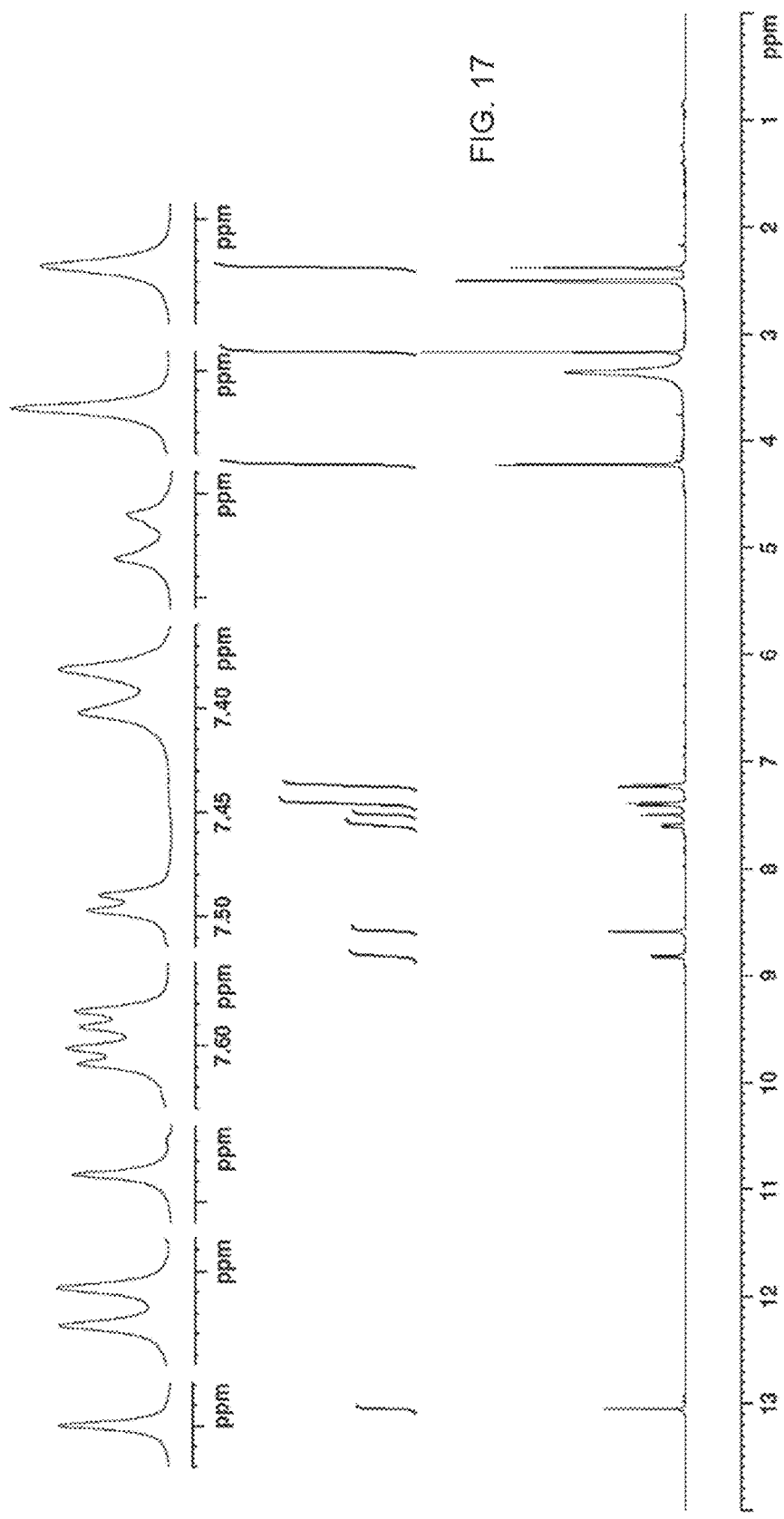
Figure 18:
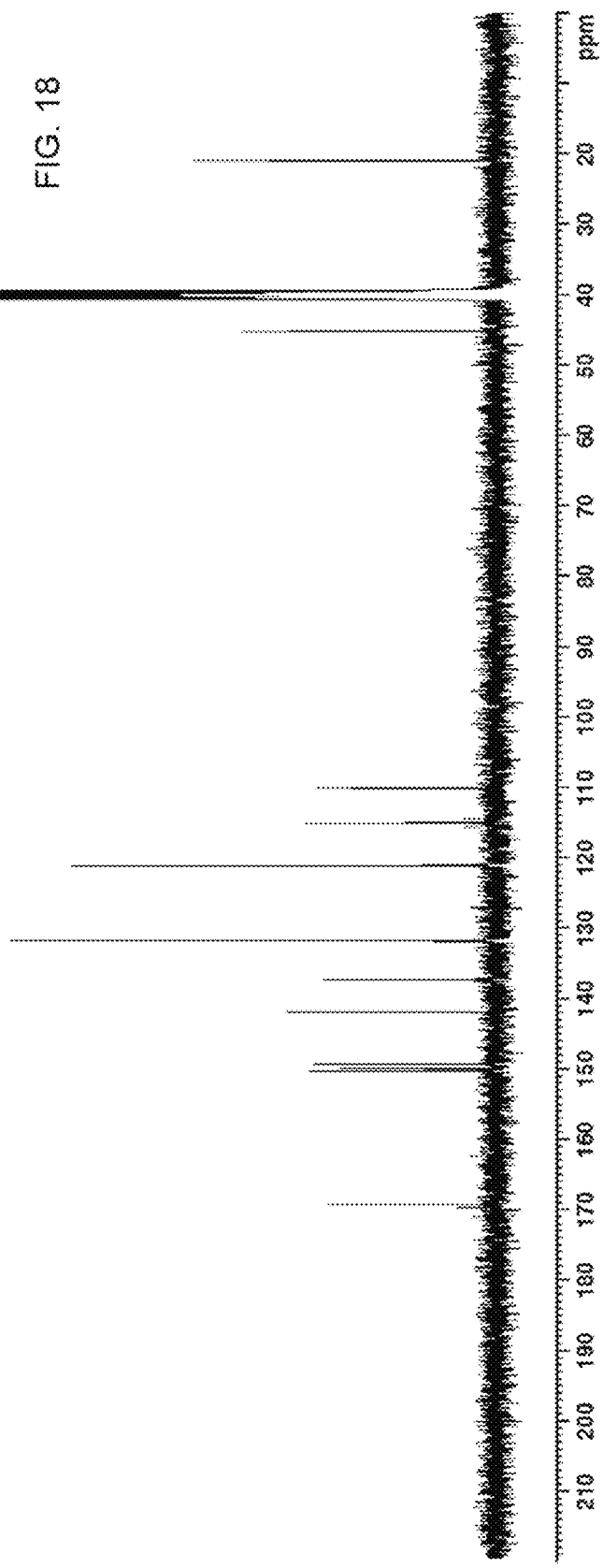
Figure 19:
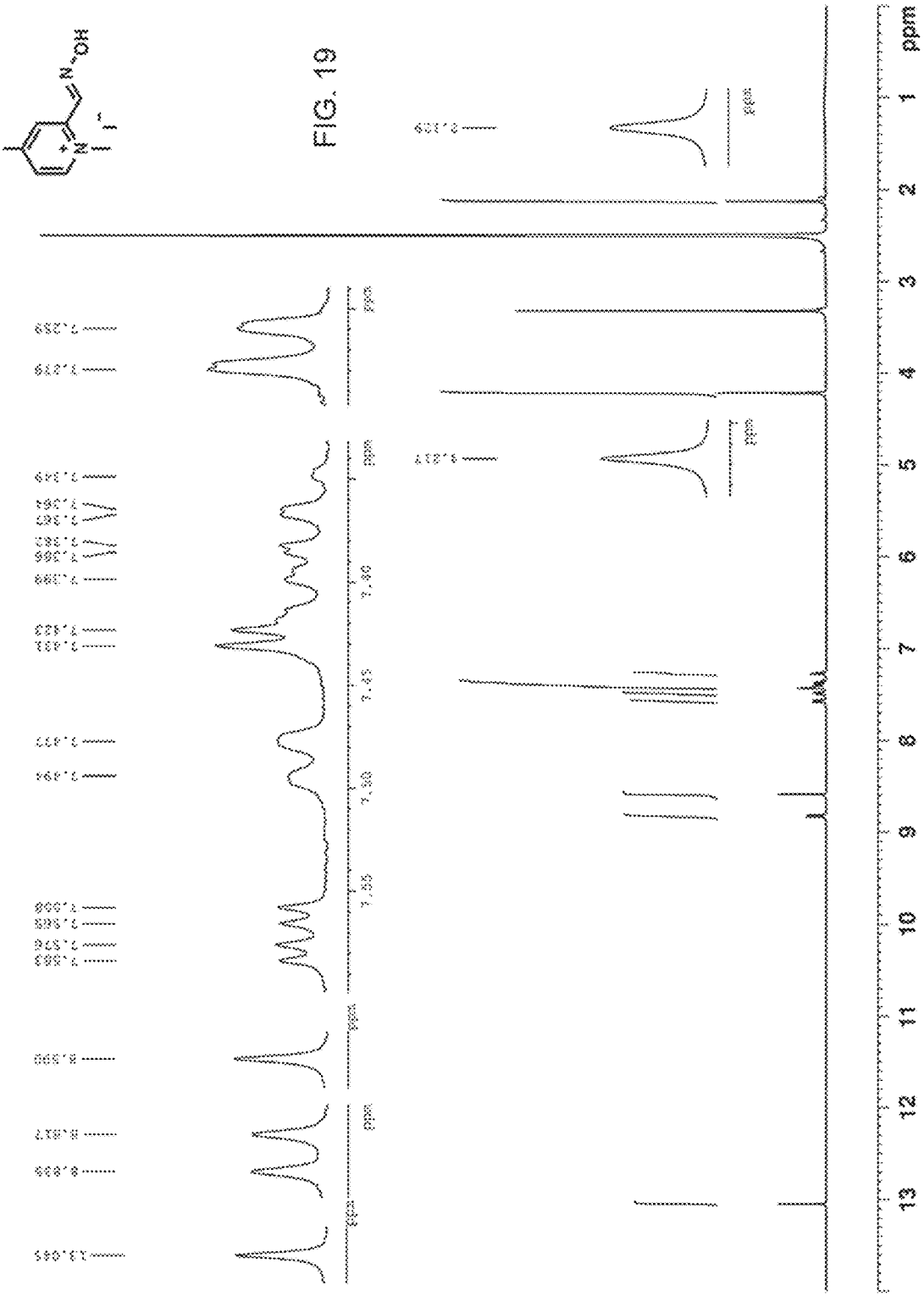
Figure 20:
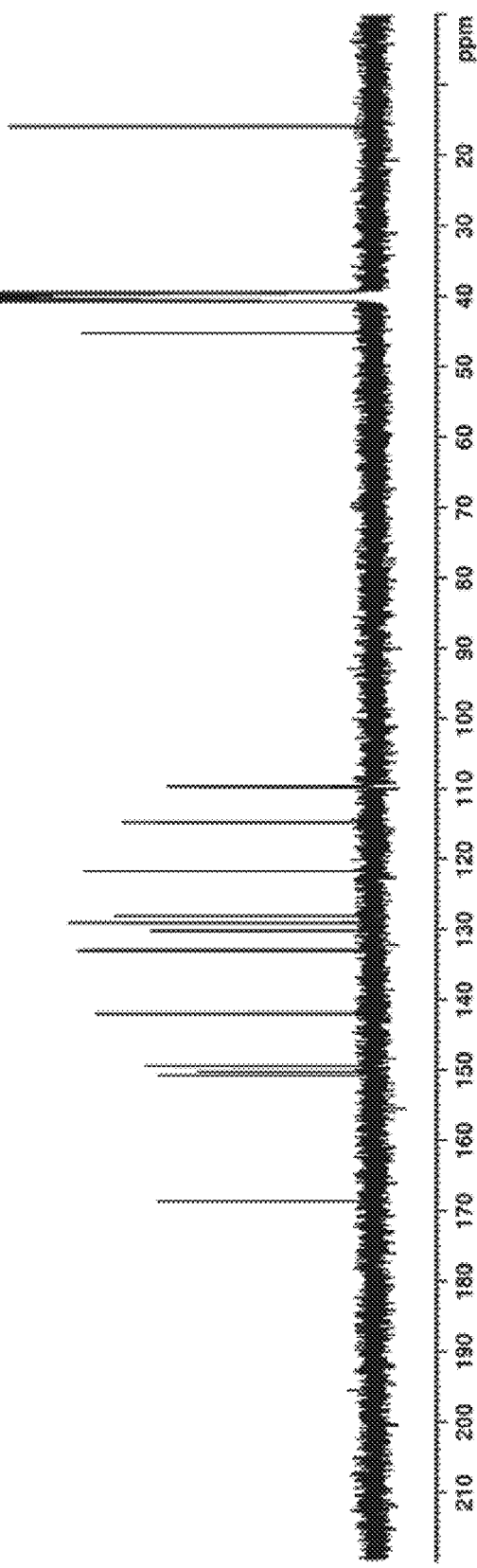
Figure 22:
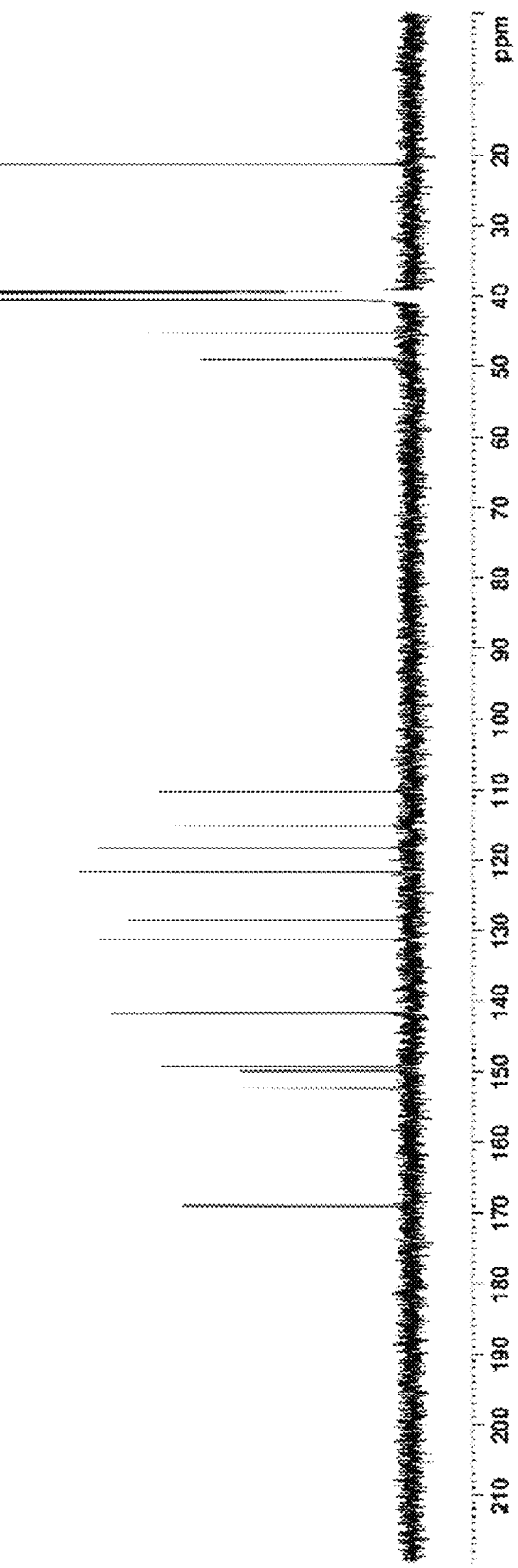
Figure 23:
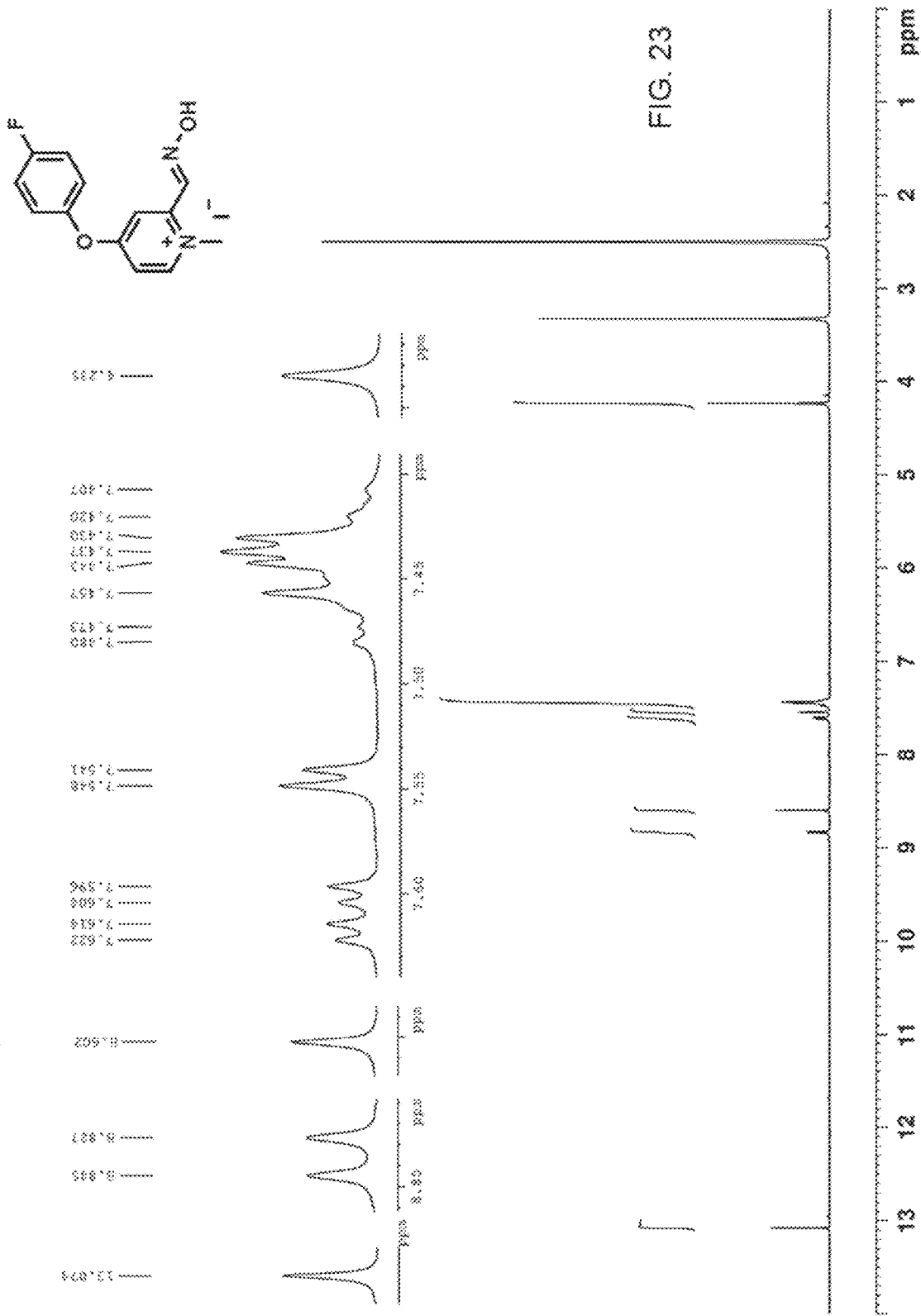
Figure 24:
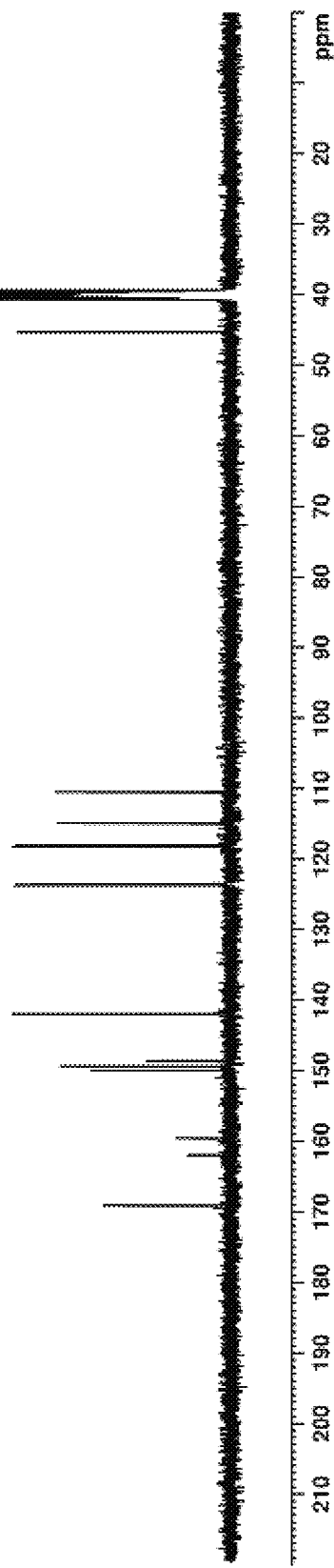
Figure 25:
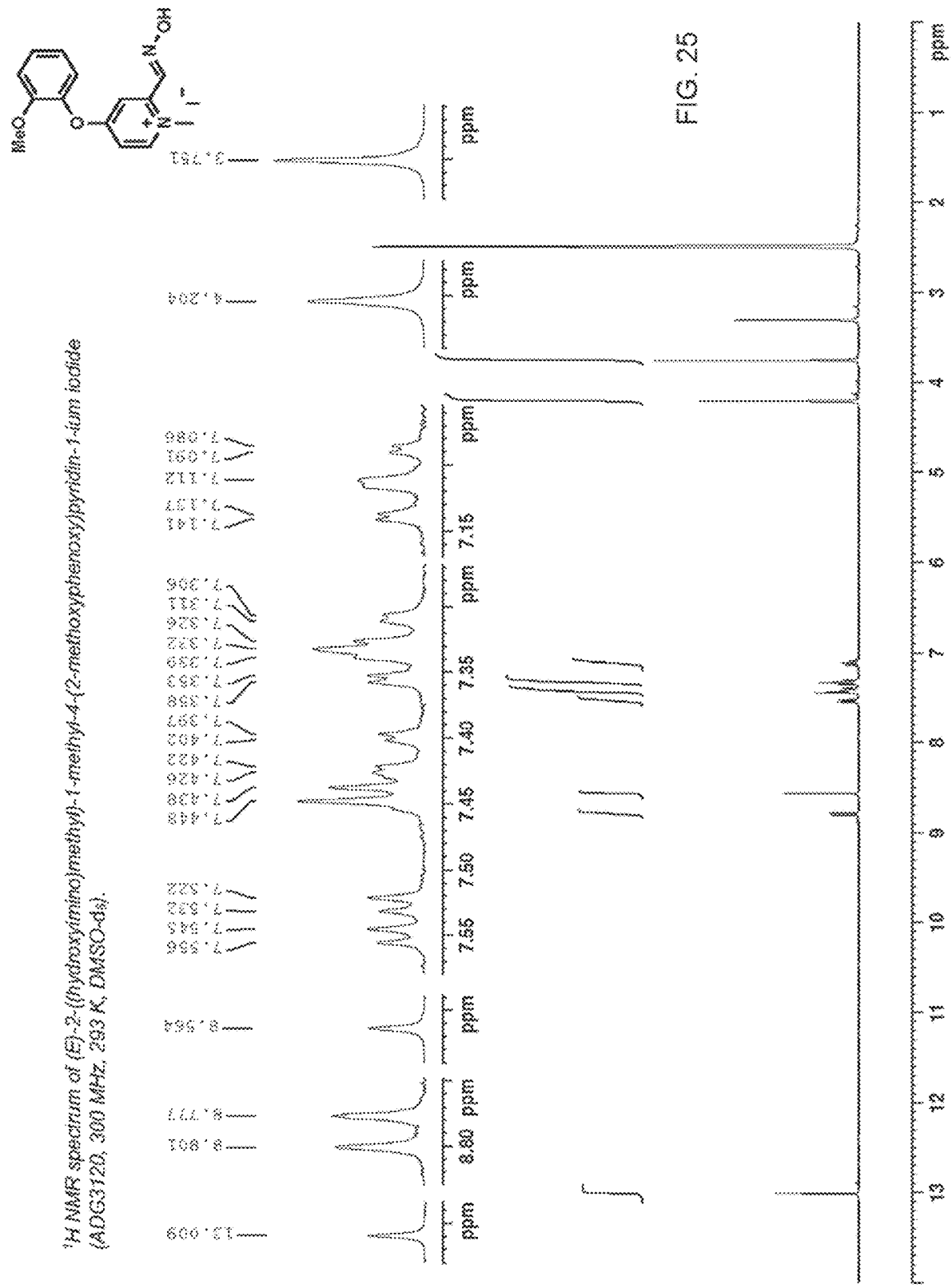
Figure 27:
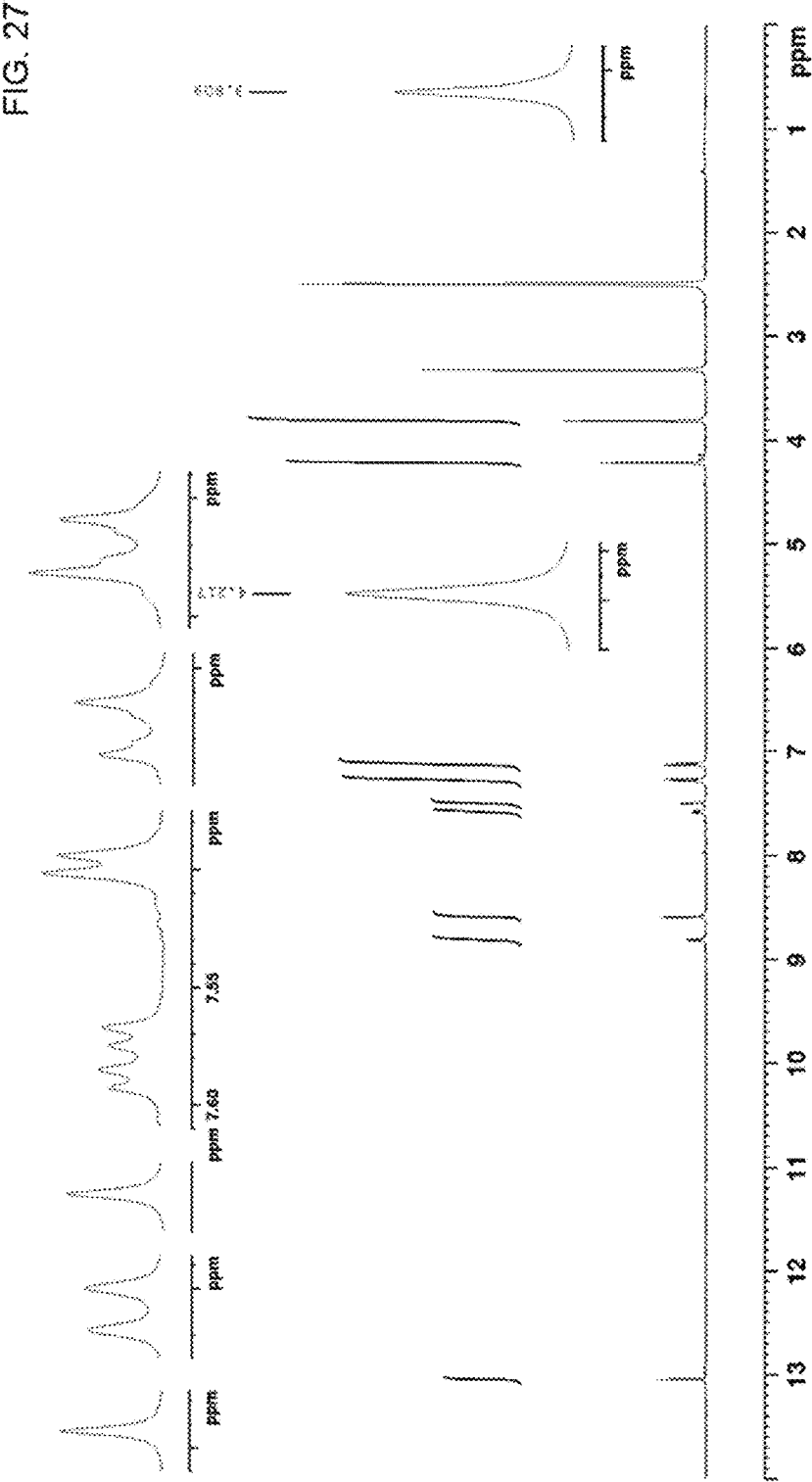
Figure 29:
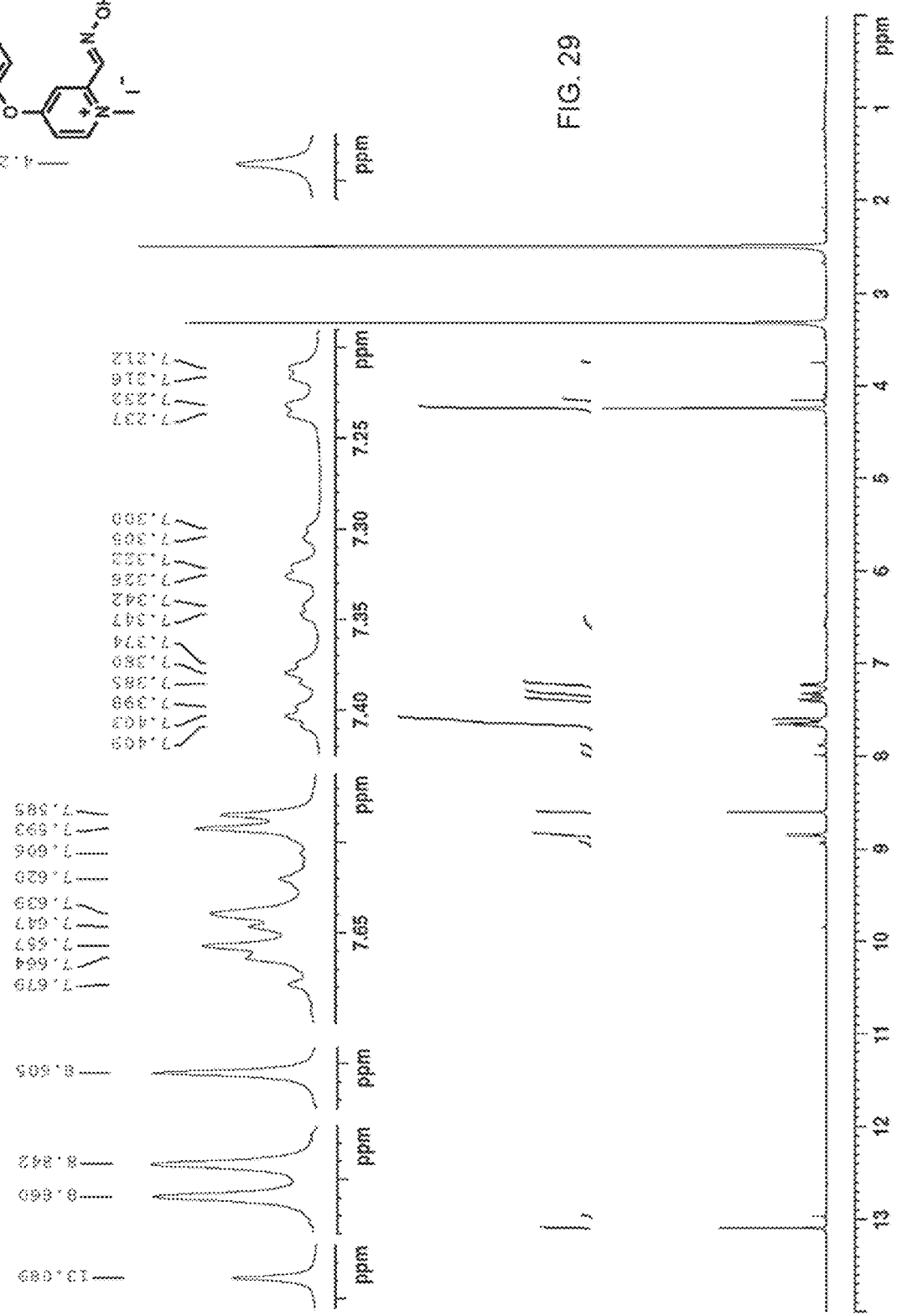
Figure 31:
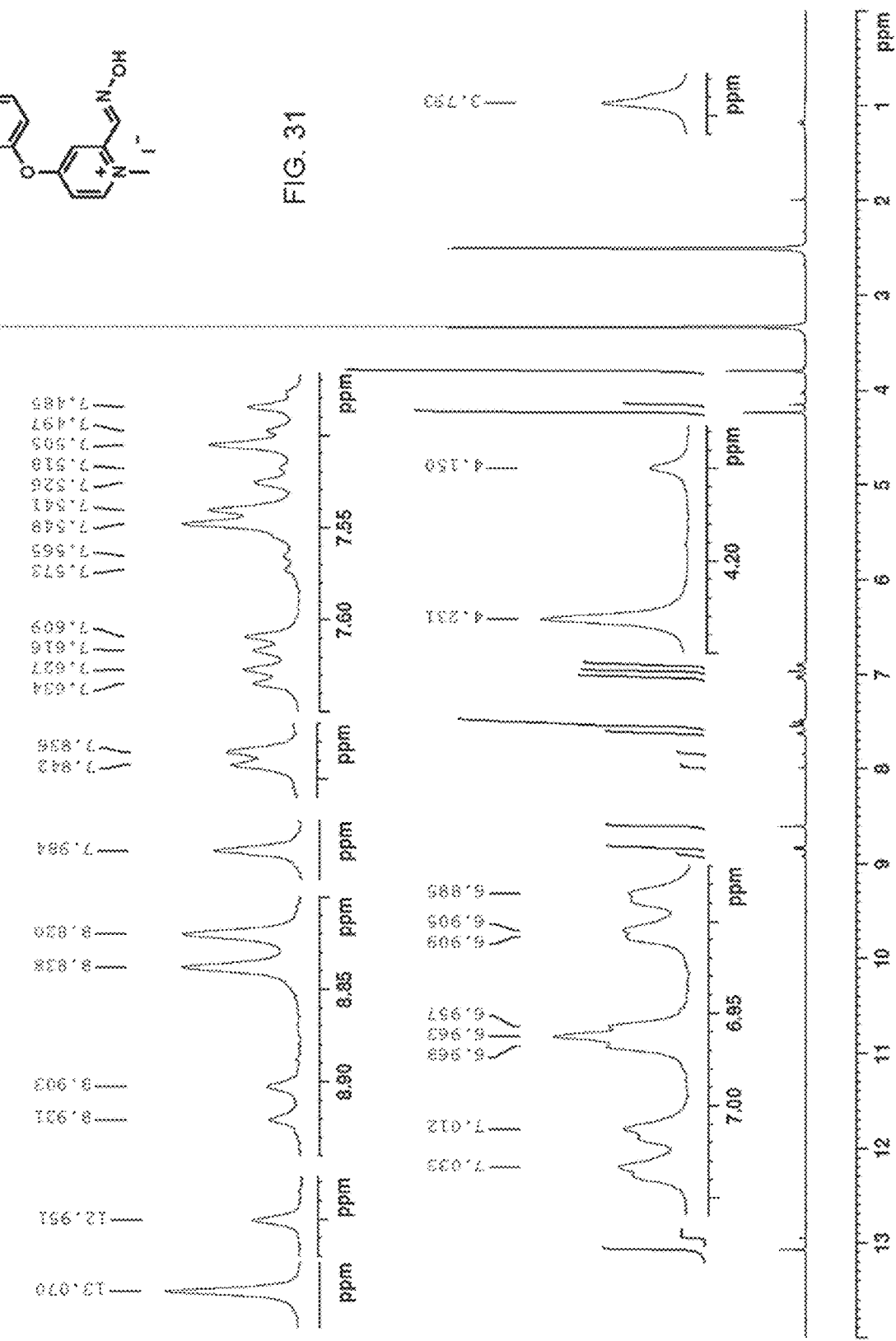
Figure 32:
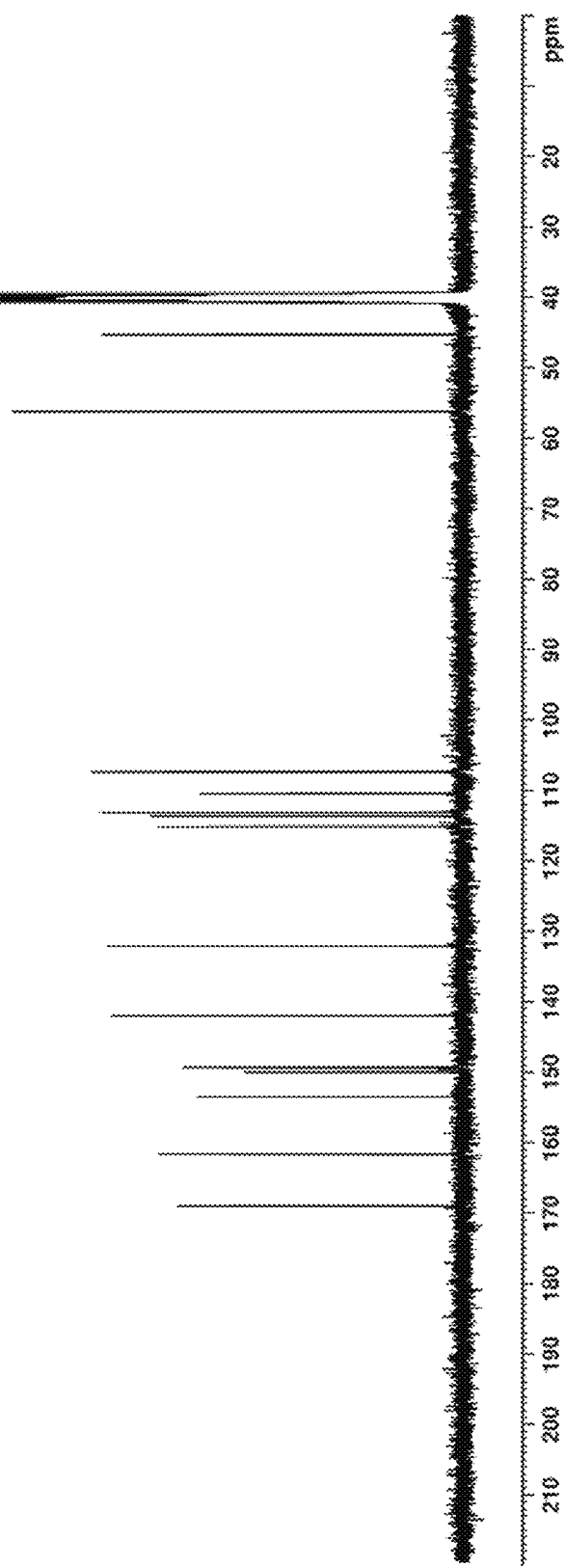
Figure 33:
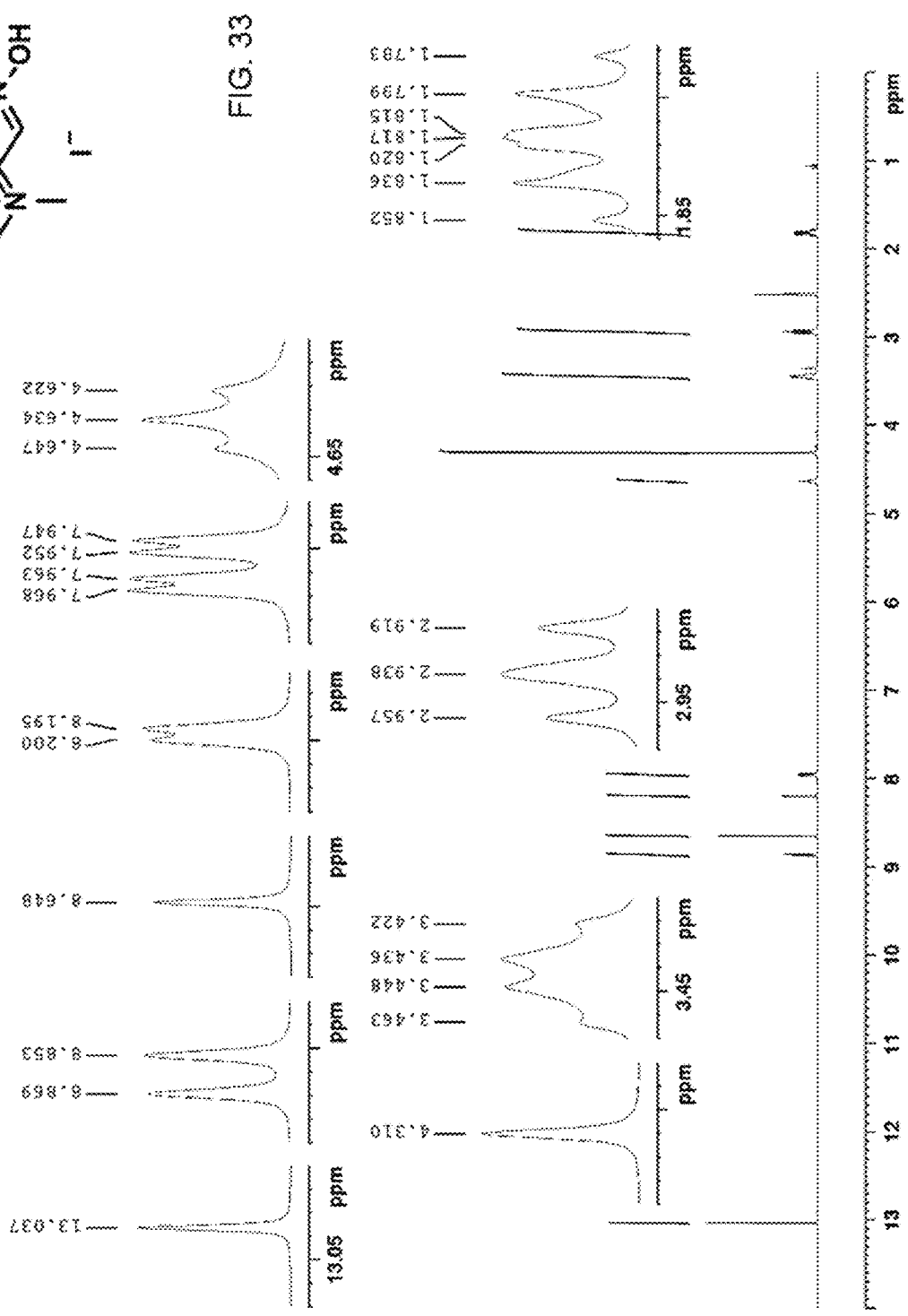
Figure 35:
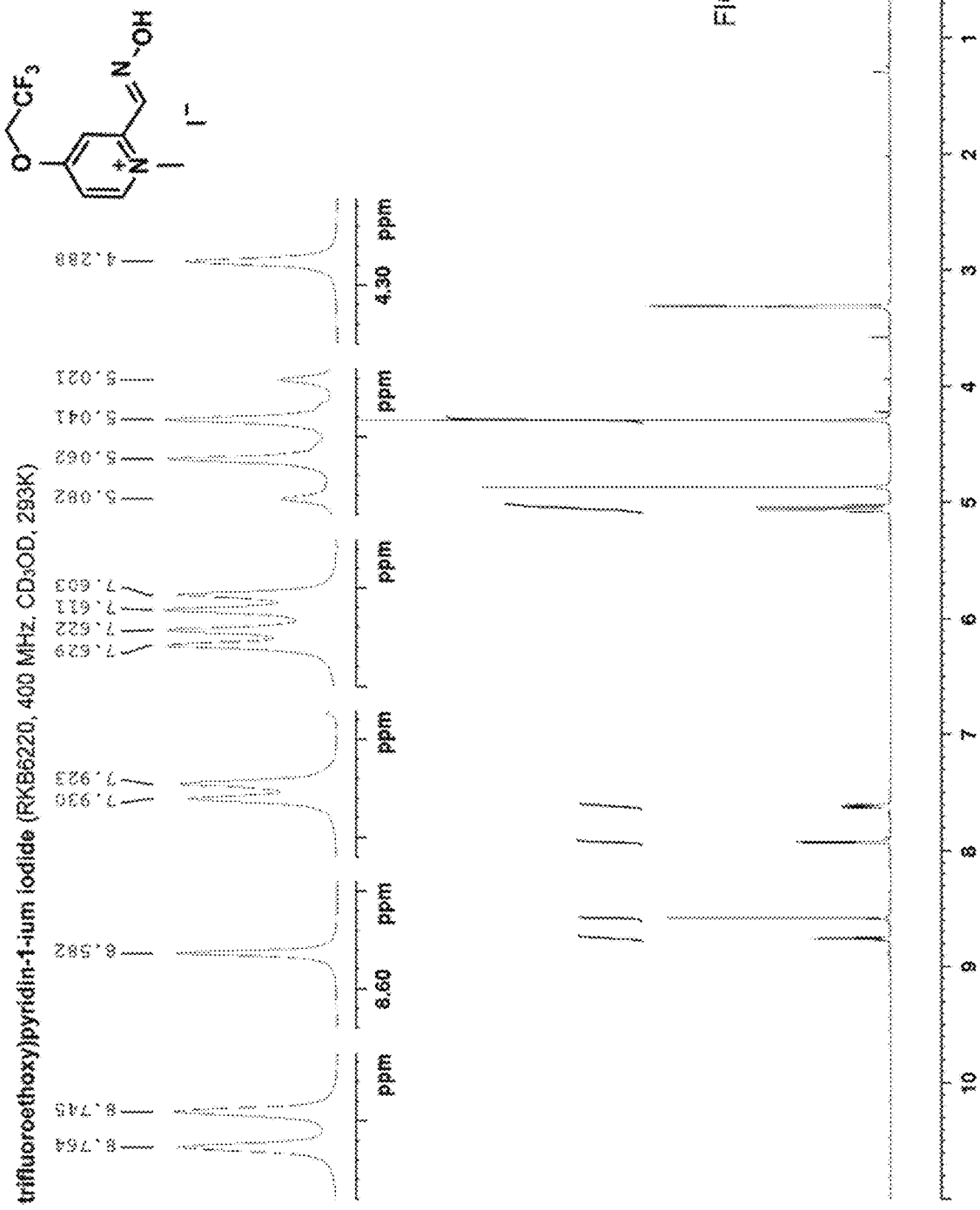
Figure 39:
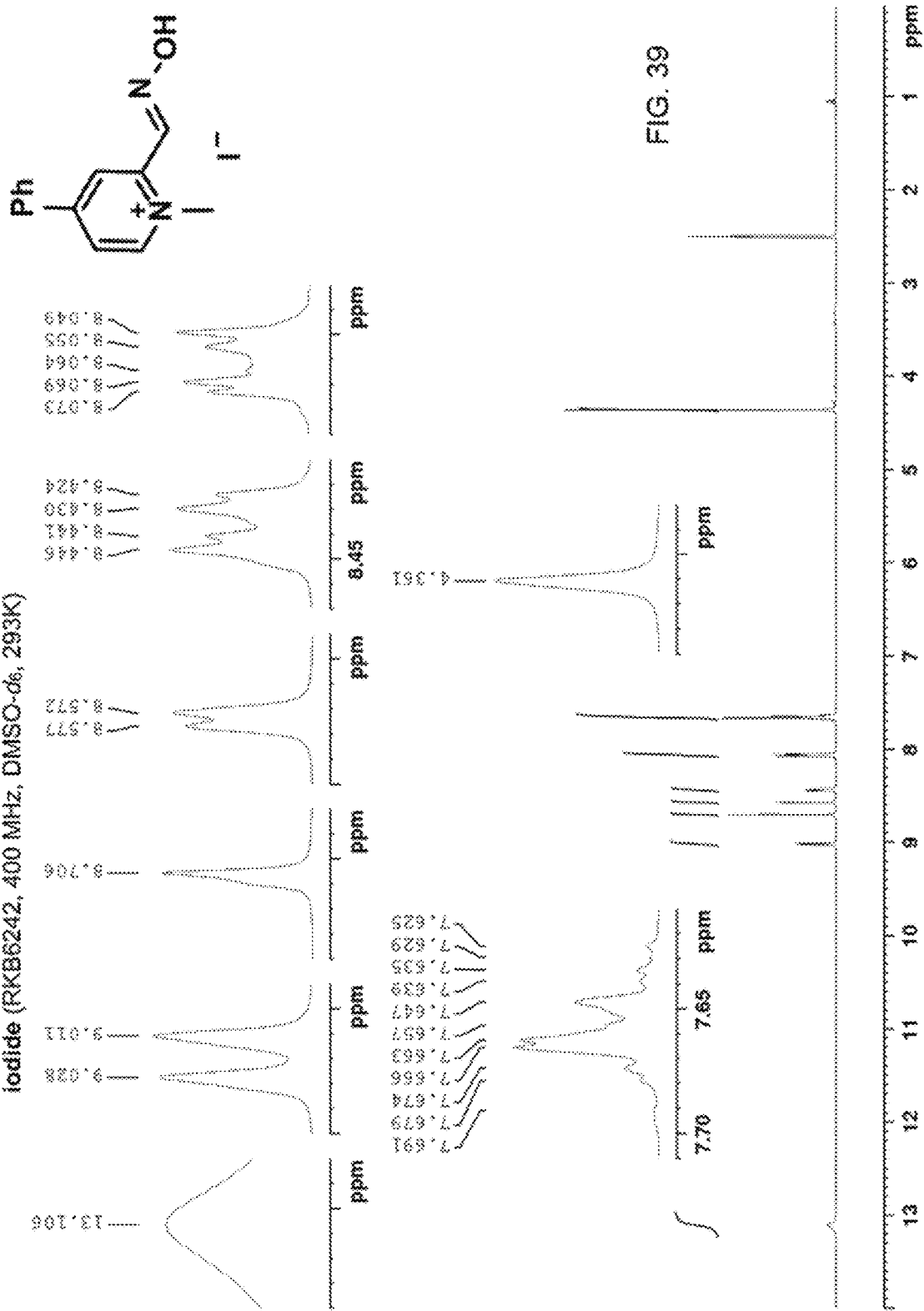
Figure 41:
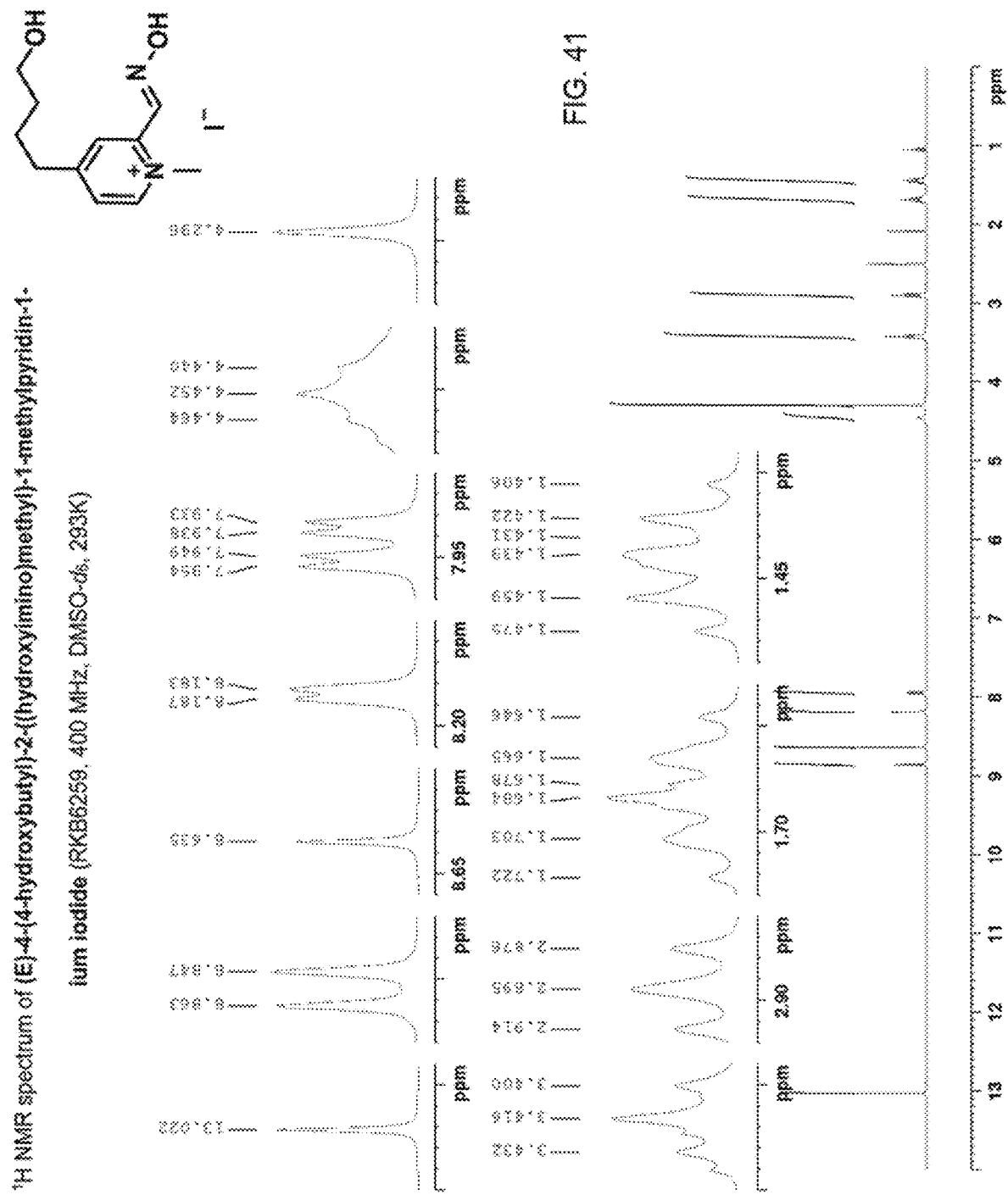
Figure 43:
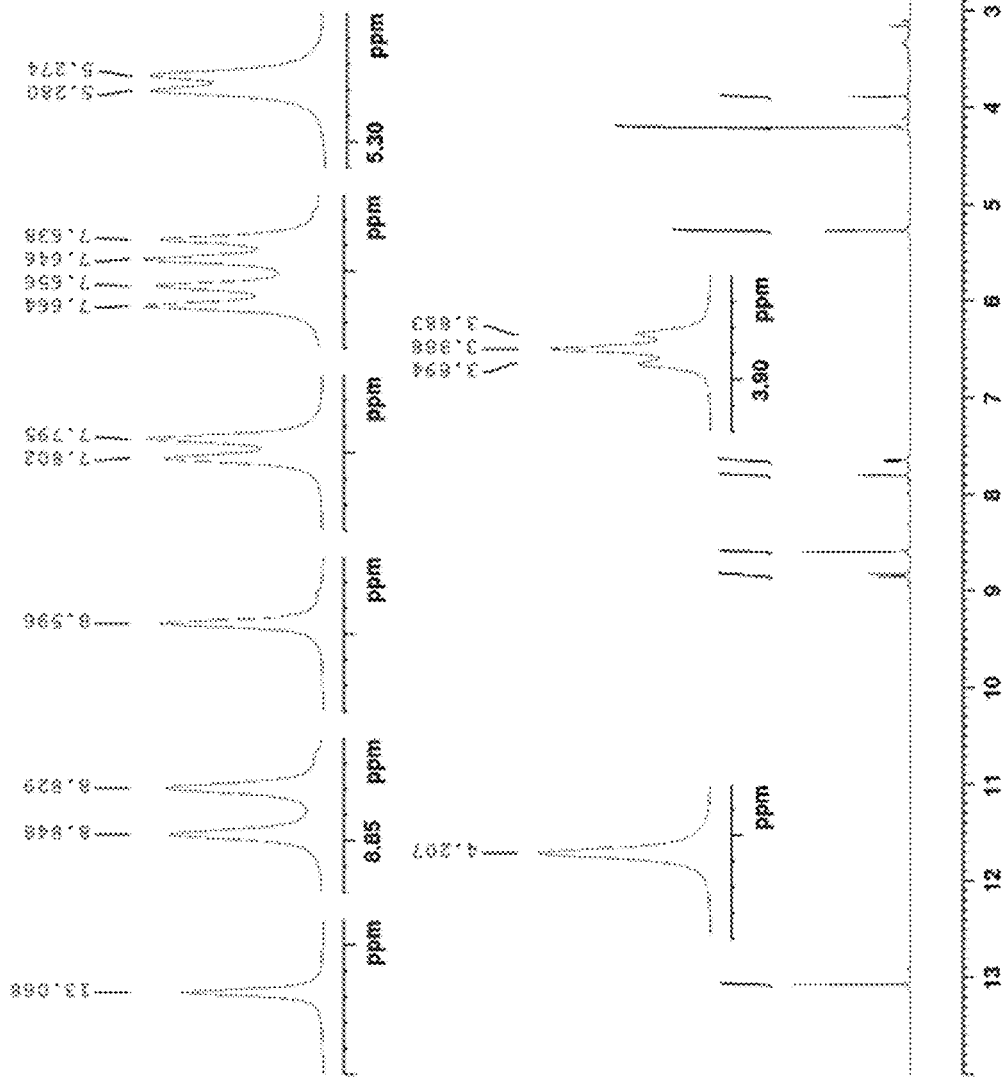
Figure 44:
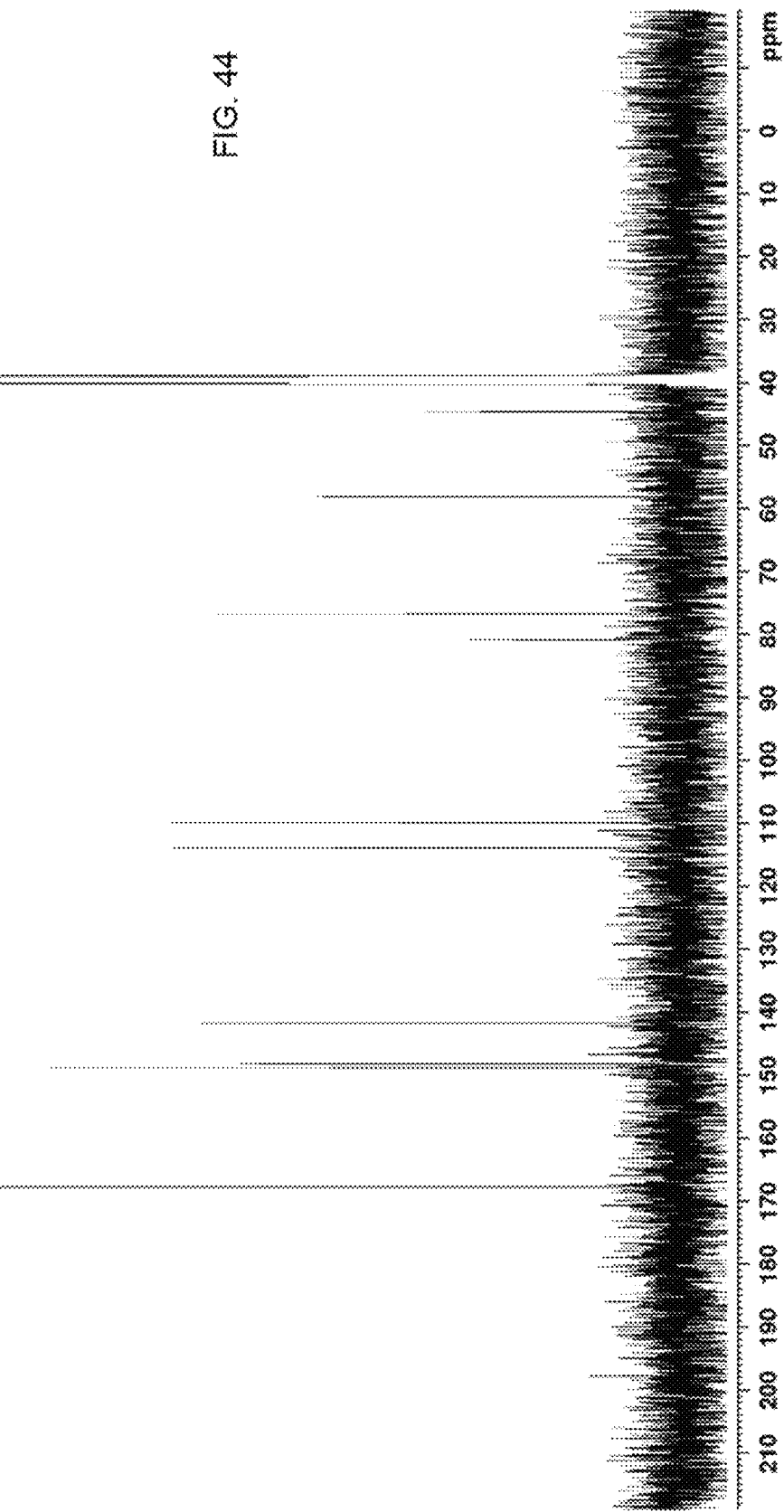
Figure 45:
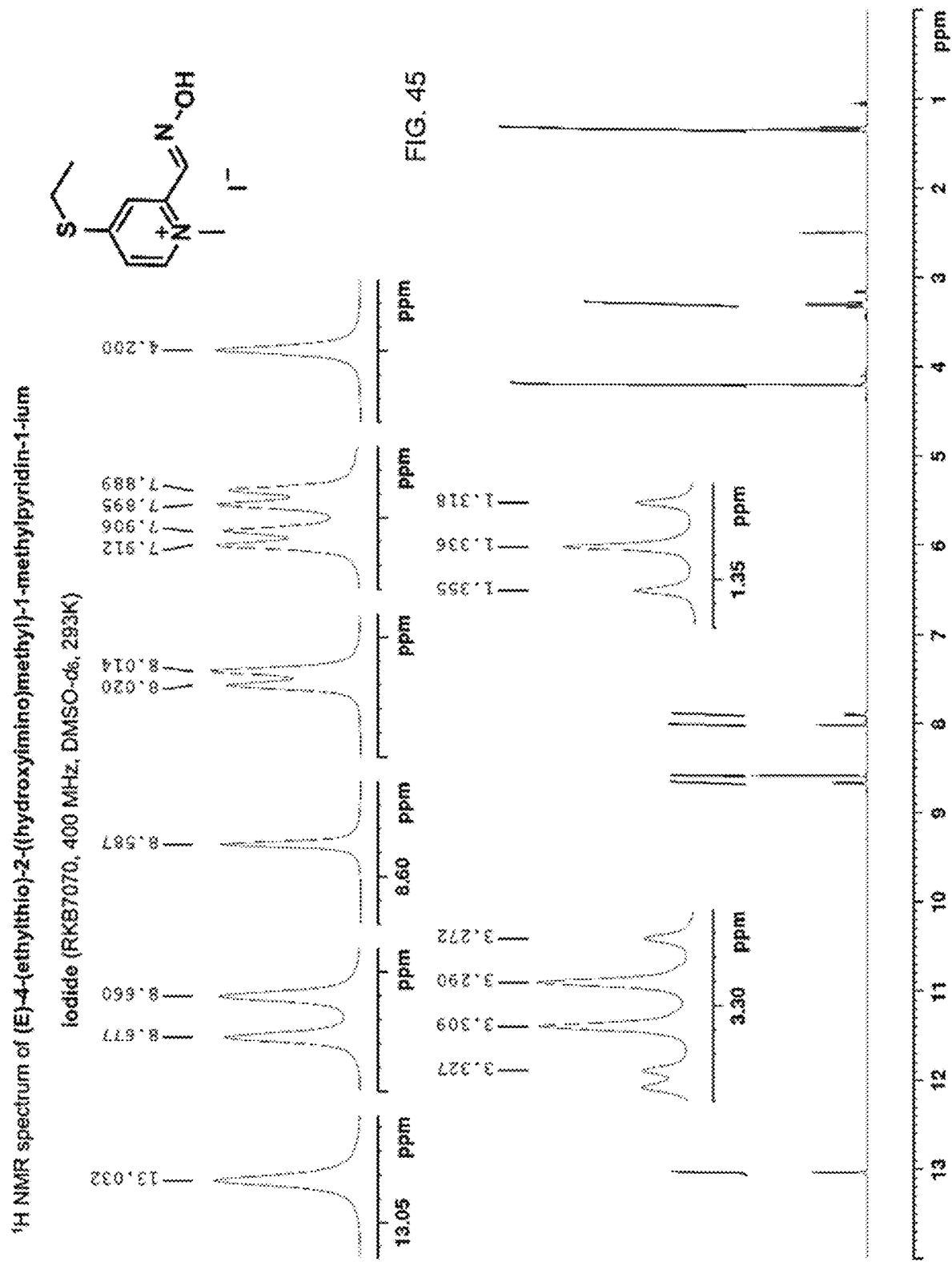
Figure 47:
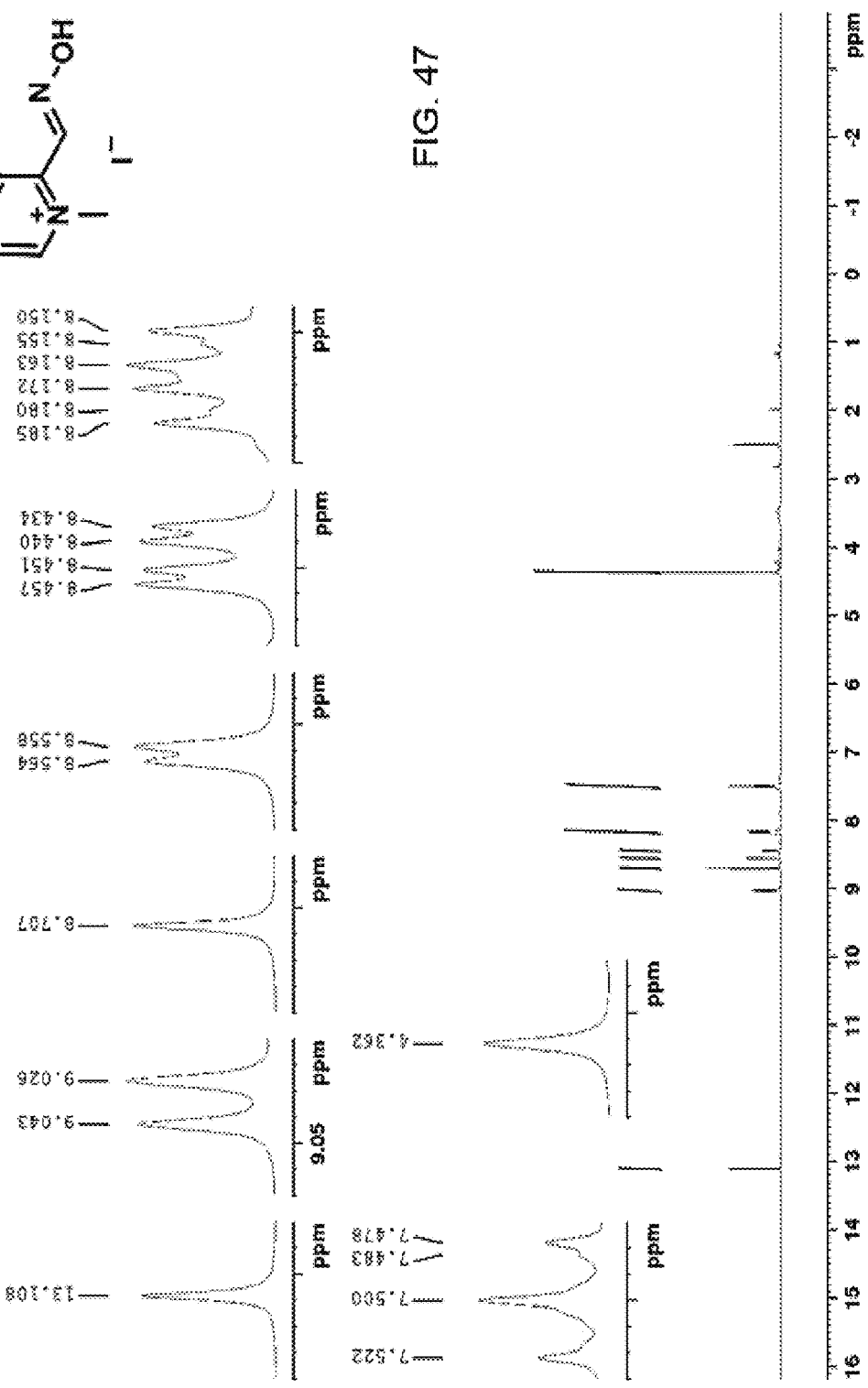
Figure 49:
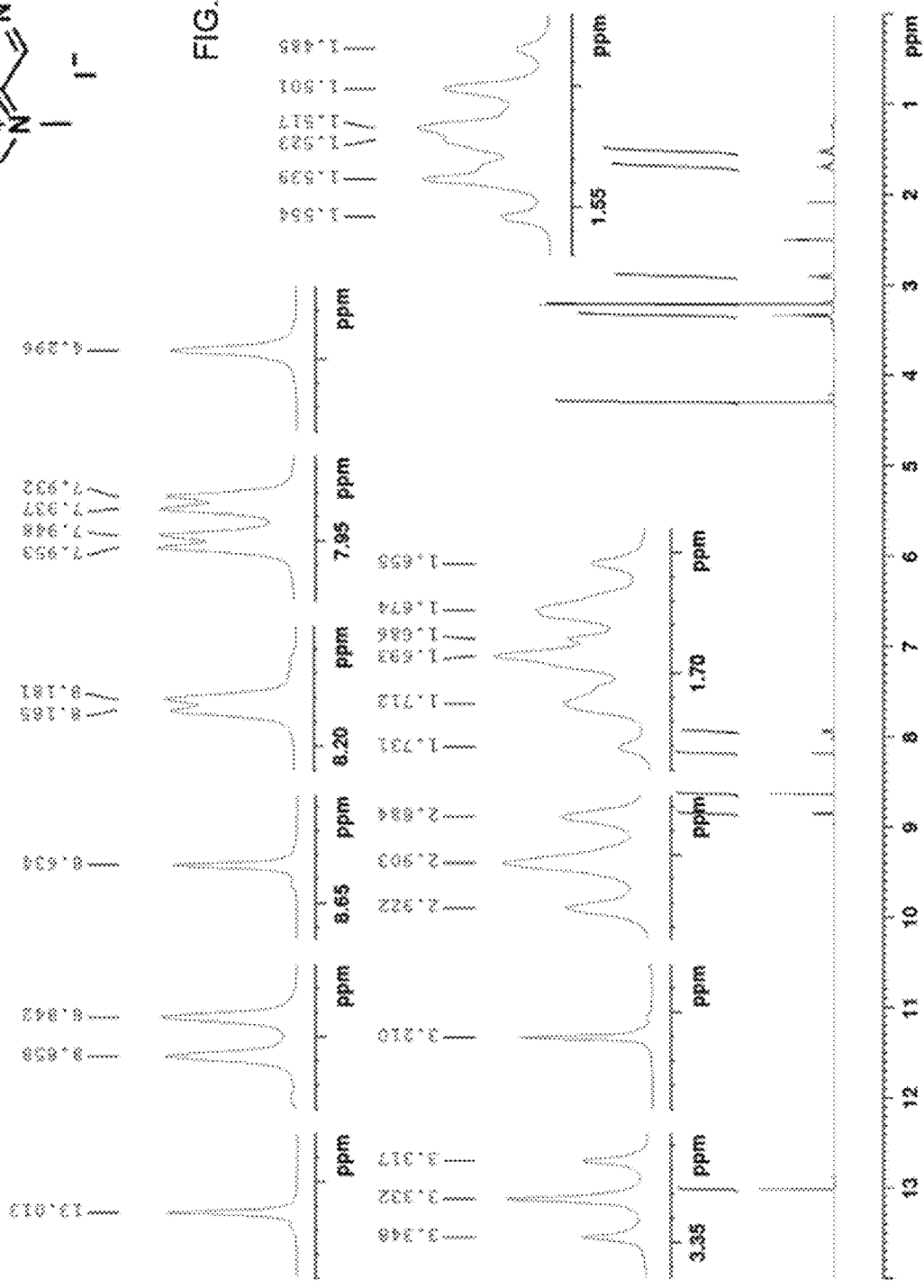
Figure 51:
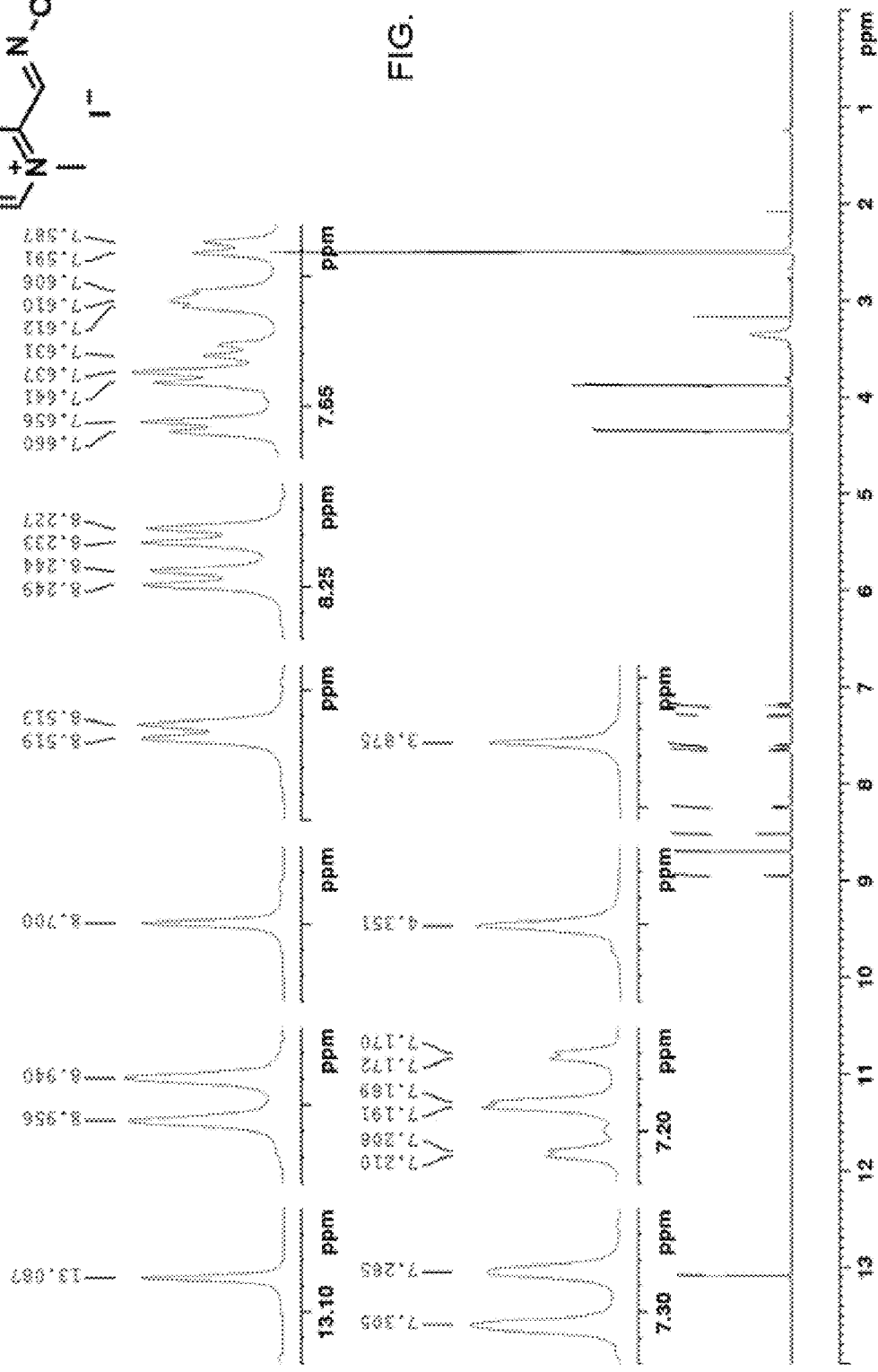
Figure 52:
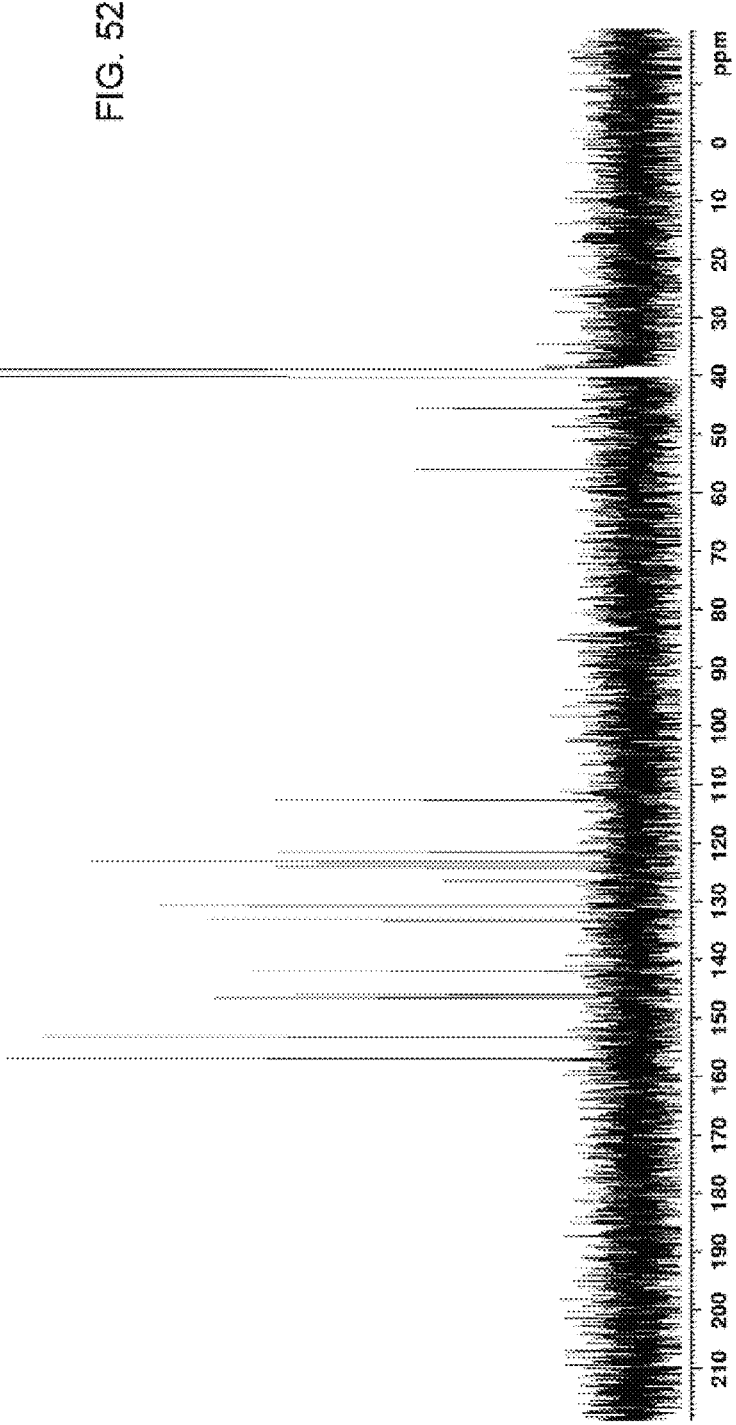
Figure 54:
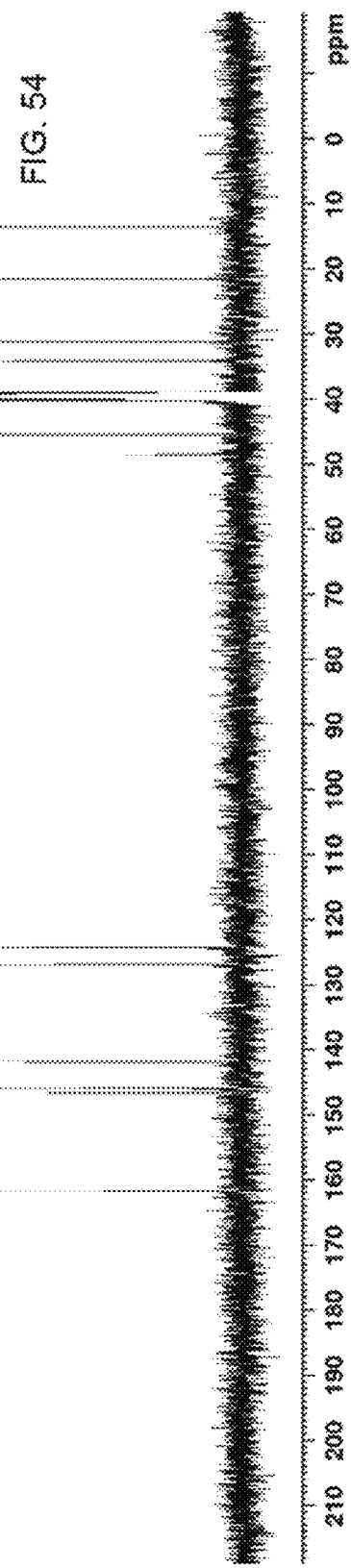

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. "Comprising" and like terms are open-ended. The term "consisting essentially of" limits the scope of a claim to the specified materials or steps and those that do not materially affect the basic and novel characteristics of the claimed invention. The term "consisting of" excludes any element, step, or ingredient not specified in the claim. The terms "a" and "an" refer to one or more.

As used herein, the term "patient" refers to members of the animal kingdom including but not limited to human beings and implies no relationship between a doctor or veterinarian and a patient.

"Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Alkylene" and "substituted alkylene" refer to divalent alkyl and divalent substituted alkyl, respectively, including, without limitation, ethylene (—$CH_2$—$CH_2$—).

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. Examples of alkenylene include without limitation, ethenylene (—CH=CH—) and all stereoisomeric and conformational isomeric forms thereof. "Substituted alkenylene" refers to divalent substituted alkene.

"Alkyne or alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne. 1-pentyne, 2-pentyne. 1-hexyne, 2-hexyne. 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy). —O— ethyl (ethoxy), —O-propyl (propoxy), —O-isopropyl (isopropoxy). —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "thioether" refers to ($C_1$-$C_{10}$)alkyl group wherein one or more of the alkyl group's carbon atoms is replaced with an —S— group. The term thioether includes —$CH_2$—($SCH_2$—$CH_2$)$_q$—$SP_1$ compounds where $P_1$ is a protecting group, —H, or a ($C_1$-$C_{10}$)alkyl. Exemplary thioethers include dimethylthioether, ethylmethyl thioether. "Alkylthio" refers to an —S-alkyl group. "Alkylamino" refers to an —N-alkyl group.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or heteroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"Halogen," "halide," and "halo" refers to —F, —Cl, —Br, and/or —I.

Unless chirality is specifically indicated, any compound described herein includes any stereoisomers thereof, and can include racemic mixtures.

Acid and base addition salts may be prepared by contacting a free base form of a compound with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Non-limiting examples of pharmaceutically-acceptable acid salts (e.g., counterions) include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, and phthalate.

Provided herein are compounds and compositions useful for counteracting the effect of exposure of a patient to a nerve agent, pesticide, or an acetylcholinesterase inhibitor, such as an organophosphorus compound. In one embodiment, the nerve agent, pesticide, or acetylcholinesterase inhibitor is sarin.

In use, any compound described herein, including pharmaceutically acceptable salts thereof, may be admixed with any pharmaceutically acceptable carrier or carriers, such as water, saline, physiological salt solutions, Ringer's solution or any other carrier customarily used for administration of drugs to the subject in question (see, generally, Troy, D B, Editor, Remington: The Science and Practice of Pharmacy, 21st edition, ed. Paul Beringer et al., Lippincott, Williams & Wilkins, Baltimore, MD Easton, Pa. (2005) (see, e.g., Chapters 37, 39, 41, 42 and 45 for examples of powder, liquid, parenteral, intravenous and oral solid formulations and methods of making such formulations).

According to one non-limiting example, the compounds described herein are formulated into a composition, such as a drug product with one or more additional pharmaceutically acceptable excipients for oral, intravenous or subcutaneous administration, such as, without limitation: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts. Although "inactive", excipients, e.g., in carrier systems or delivery systems, ingredients may facilitate and aid in increasing the delivery, stability or bioavailability of an active ingredient in a drug product. The composition can be formulated in a classical manner using solid or liquid vehicles, diluents and additives appropriate to the desired mode of administration. The compositions optionally comprise one or more additional active agents, as are broadly known in the pharmaceutical, medicinal, veterinary or biological arts.

A dosage form is a composition, optionally including a device, for delivery of a therapeutic agent, such as a 2-pralidoxime analog compound according to any aspect or embodiment described herein, optionally along with a muscarinic acetylcholine receptor antagonist and/or a benzodiazepine, in a therapeutic composition to a patient. A unit dose provides a single dose of a therapeutic composition to a patient, and a dosage form may provide multiple single doses, though typically a dosage form provides a single unit dose, as in a capsule, tablet, or autoinjection device.

In any case, as used herein, any agent or agents used for treating exposure of a patient to a nerve agent, pesticide, or an acetylcholinesterase inhibitor, such as an organophosphorus compound, for example sarin, is administered in an amount effective to improve one or more symptoms of exposure of a patient to a nerve agent, pesticide, or an acetylcholinesterase inhibitor, namely in an amount and in a dosage regimen effective to treat exposure of a patient to a nerve agent, pesticide, or an acetylcholinesterase inhibitor, such as an organophosphorus compound, for example sarin. According to one non-limiting embodiment, an effective dose ranges from 0.05 to 200 mg/kg/day, and in certain embodiments less than 100 mg/kg/day, including any increment or range therebetween, including 0.1 mg/kg/day, 0.5 mg/kg/day, 1 mg/kg/day, 5 mg/kg/day, 10 mg/kg/day, 20 mg/kg/day, 25 mg/kg/day, 50 mg/kg/day, 75 mg/kg/day, 100 mg/kg/day, etc. However, for each compound described herein, an effective dose or dose range is expected to vary from that of other compounds described herein for any number of reasons, including the molecular weight of the compound, bioavailability in the dosage form, route of administration, specific activity (e.g., EC50), etc. In vitro (including ex vivo), the composition is used, for example, in culture medium. Exemplary and non-limiting effective ranges range from 100 nM to 25 µM, 200 nM to 3 µM, 200 nM to 1.5 µM, including all increments therebetween. Once again, the effective range and optimal concentration range depends on the specific activity (e.g., EC50) of the composition, as well as a variety of other conditions. In any case, the effective range (e.g., the therapeutic window) between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding agents, such as histone deacetylase inhibitors. Different concentrations of the agents described herein are expected to achieve similar results. The compounds can be administered orally one or more times daily, for example two to four times daily, once every two, three, four, five or more days, weekly, monthly, etc., including increments therebetween. In certain delivery methods, it is possible to deliver the drug continuously, or substantially continuously as in the case of, for example, intravenous or transdermal delivery routes. A person of ordinary skill in the pharmaceutical and medical arts will appreciate that it will be a matter of design choice and/or optimization to identify a suitable dosage regimen for treating exposure of a patient to a nerve agent, pesticide, or an acetylcholinesterase inhibitor, such as an organophosphorus compound, for example sarin.

The compounds described herein may be administered in any manner that is effective to treat exposure of a patient to a nerve agent, pesticide, or an acetylcholinesterase inhibitor, such as an organophosphorus compound, for example sarin.

Examples of delivery routes include, without limitation: topical, for example, epicutaneous, inhalational, enema, ocular, otic and intranasal delivery; enteral, for example, orally, by gastric feeding tube or swallowing, and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral or intravenous approaches being preferred for treating exposure of a patient to a nerve agent, pesticide, or an acetylcholinesterase inhibitor, such as an organophosphorus compound, for example sarin.

In one embodiment, the compositions described herein comprising a 2-pralidoxime analog are administered by an autoinjection device (an "autoinjector"), e.g., a spring-loaded syringe, such as an autoinjection "pen" as are broadly-known in the pharmaceutical arts, for example as are currently used to deliver atropine and 2-pralidoxime (see, e.g., the DUODOTE® injection system, available from Meridian Medical Technologies, Inc.), e.g., for use by the military and first responders. As such, a dosage form, in the form of an autoinjection device, delivers a therapeutic composition comprising the 2-pralidoxime analog, and, optionally, one or both of an muscarinic acetylcholine receptor antagonist, such as atropine or scopolamine, or a benzodiazepine, such as alprazolam, clobazam, clonazepam, clorazepate, chlordiazepoxide, diazepam, estazolam, lorazepam, oxazepam, temazepam, or triazolam.

In use, any 2-pralidoxime analog compound as described herein, whether or not incorporated as a drug product, is useful, and finds use in: methods of treating, e.g., as an antidote to, exposure of a patient to an organophosphorus compound, such as a nerve agent, pesticide, or an acetylcholinesterase inhibitor, for example sarin. In any such method, the compound or composition is used in an amount effective to achieve the stated goal (e.g., in amounts and dosage regimens as illustrated herein), e.g., treating exposure of a patient to a nerve agent, pesticide, or an acetylcholinesterase inhibitor, such as an organophosphorus compound, for example sarin. A suitable end-point may be prevention of lethality or improvement of one or more clinical symptoms of exposure of a patient to a nerve agent, pesticide, or an acetylcholinesterase inhibitor, such as an organophosphorus compound, for example sarin for each method are provided herein. Severe clinical symptoms of exposure of a patient to sarin include: loss of consciousness, convulsions; paralysis, and respiratory failure possibly leading to death.

The compounds described herein may be co-administered with one or more additional therapeutic agents useful for treating a patient exposed to a nerve agent, pesticide, or an acetylcholinesterase inhibitor, such as an organophosphorus compound, for example sarin. The compounds are reactivators of phosphorylated acetylcholine esterase. In one example, an effective amount of a muscarinic acetylcholine receptor antagonist, such as atropine or scopolamine, is co-administered with a 2-pralidoxime analog compound described herein. In another example, an effective amount of a benzodiazepine, such as diazepam, is co-administered with a 2-pralidoxime analog described herein. The one or more additional therapeutic agents may be administered either as part of the same dosage form as the 2-pralidoxime analog, or separately.

Figure 55:
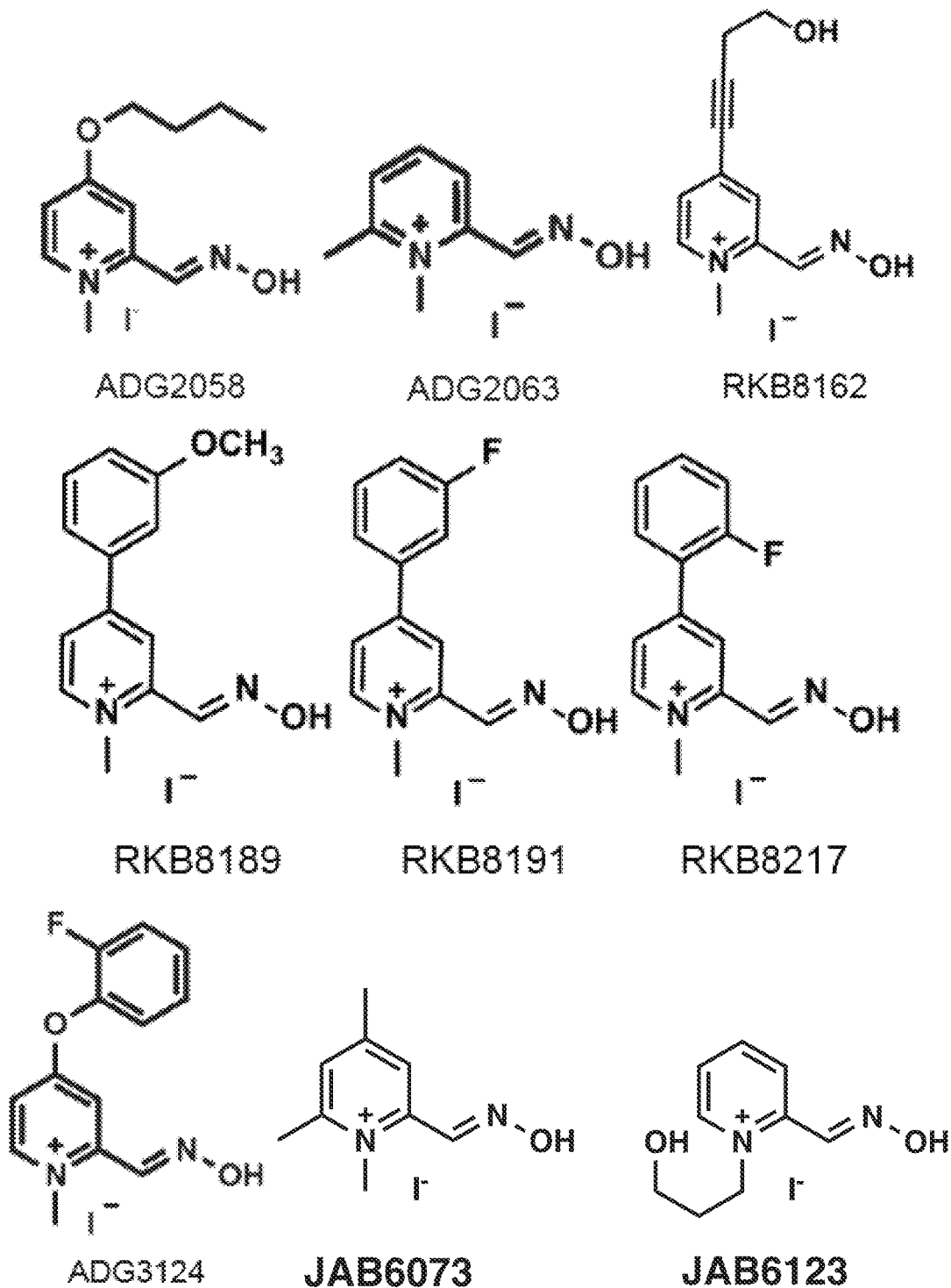
FIG. 55 provides structures for additional compounds disclosed herein.

Therefore provided herein are 2-pralidoxime analogs useful as antidotes against organophosphorus nerve agents, such as sarin. Organophosphorus nerve agents, such as sarin, phosphorylate the active serine residue of acetylcholinesterase. The described 2-pralidoxime analog compounds act to dephosphorylate phosphorylated acetylcholinesterase, and thereby reactivate that enzyme. The compounds have the structure:

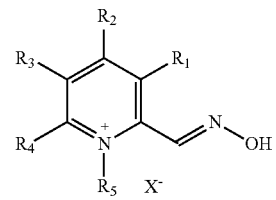

wherein:
$R_1$ and $R_3$ are H; $R_4$ is H or methyl;
$R_2$ is H; methyl; phenyl, halomethyl;

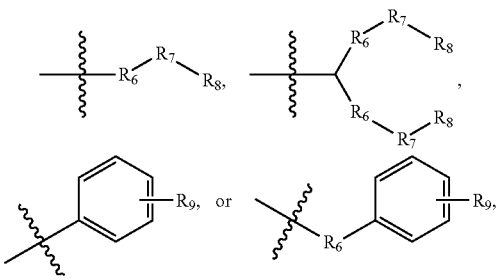

wherein each instance of $R_6$ is, independently, C, O, S, N, carbonyl, sulfinyl, or sulfonyl, each instance of $R_7$ is, independently, a $C_1$-$C_4$ saturated alkane, each instance of $R_8$ is, independently, H, hydroxyl, halo, halomethyl, phenyl, $C_1$-$C_4$ alkoxyl, amine, carboxyl, N($C_1$-$C_4$ alkyl)$_2$, NH($C_1$-$C_4$ alkyl), or azide, and $R_9$ is H, halo, methoxyl, methyl; prop-2-yn-1-yloxyl; 4-hydroxybut-1-yn-1-yl; 3-hydroxyprop-1-yn-1-yl; or phenylethynyl;

$R_5$ is methyl or 3-hydroxypropyl (—$CH_2CH_2CH_2OH$) when $R_2$ and $R_4$ are H; and $X^-$ is a counterion. In various embodiments, the counterion is $Cl^-$ or $I^-$. Nonlimiting examples of the compounds are depicted in FIGS. 1-55, e.g., ADG2058, ADG2063, ADG2078, ADG2173, ADG2180, ADG2293, ADG2294, ADG3001, ADG3002, ADG3003, ADG3035, ADG3060, ADG3092, ADG3110, ADG3111, ADG3116, ADG3120, ADG3121, ADG3123, ADG3124, ADG3128, RKB6186, RKB6220, RKB6229, RKB6242, RKB6259, RKB6284, RKB7070, RKB8122, RKB8160, RKB8162, RKB8189, RKB8191, RKB8217, RKB8218, RKB8274, JAB5117, JAB6073, or JAB6123, or any pharmaceutically-acceptable salt of the preceding. FIGS. 1-55 depict iodide salts of those compounds. Reference to "any pharmaceutically acceptable salts of any of those stated compounds, include any pharmaceutically-acceptable salt of the stated compound, including iodide salts. For example, ADG2058 refers to the iodide salt of that compound as shown in FIG. 1. "Any pharmaceutically-acceptable salt" of ADG2058, incudes the iodide counterion, as well as any pharmaceutically-acceptable counterion. Structures for additional compounds according to the present invention, all verified by NMR, are provided in FIG. 55.

In one embodiment, $R_2$ is H, one of $R_1$, $R_3$, and $R_4$ is methyl, and the others of $R_1$, $R_3$, and $R_4$ are H. In a further embodiment, the compound has the structure (where R5 is methyl and $R_1$, $R_3$, and $R_4$ are H):

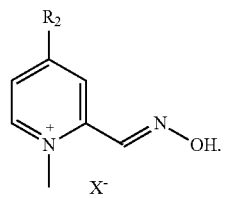

In embodiments, $R_1$, $R_3$, and $R_4$ are H, R5 is methyl, and $R_2$ is hydroxypropyl; hydroxybutyl; $C_1$-$C_4$ alkyloxy; propynyloxy; 3-hydroxy-3-methylbutyl; phenyl; ethyl-substituted phenyl; phenylethyl; phenylethynyl; $C_1$-$C_3$ saturated or unsaturated alkyl; —$CF_3$; 2,2,2-trifluoro ethoxy; ethylthio; or one of $R_1$, $R_3$, and $R_4$ is methyl, the others of $R_1$, $R_3$, and $R_4$ are H, $R_2$ is H, and $X^-$ is a pharmaceutically-acceptable anion. In examples, $R_2$ is methyl, phenyl, phenylethyl, trifluoromethyl, 3-hydroxypropyl, 4-hydroxybutyl, 3-hydroxy-3-methylbutyl, ethoxyl, butoxyl, isopropoxyl, 2,2,2-trifluoroethoxyl, prop-2-yn-1-yloxyl, phenylethynyl, or ethylthio, and $R_1$, $R_3$, and $R_4$ are H. In various embodiments, the anion is $Cl^-$ or $I^-$.

In a further embodiment, $R_1$, $R_3$, and $R_4$ are H, and $R_2$ is methyl, propyl, butyl, phenyl, 2-melhoxyphenyl, 3-methoxyphenyl, 4-methoxyphenyl, 4-methoxybutyl, 4-fluorobutyl, 2-fluorophenyl, 3-fluorophenyl, 4-fluorophenyl, ethoxyl, propoxyl, isopropoxyl, butoxyl, phenoxyl, o-tolyloxyl, m-tolyloxyl, p-tolyloxyl, 2-hydroxyethoxyl, 2-fluorophenoxyl, 3-fluorophenoxyl, 4-fluorophenoxyl, 2-methoxyphenoxyl, 3-methoxyphenoxyl, 4-methoxyphenoxyl, prop-2-yn-1-yloxy, 2,2,2-trifluoroethoxyl, ethylthio, propylthio, isopropylthio, butylthio, tert-butylthio, phenylthio, 3-hydroxypropyl, 4-hydroxybutyl, 3-hydroxy-3-methylbutyl, ethylamino, or 4-hydroxybut-1-yn-1-yl.

Also provided herein is a composition, such as a pharmaceutically-acceptable composition, comprising a 2-pralidoxime analog compound according to any aspect or embodiment described herein, and a carrier, such as a pharmaceutically-acceptable excipient. The composition may be formulated into a dosage form, such as an oral dosage form or an autoinjection device for delivery upon exposure to, or possible exposure to, a nerve agent, pesticide, or an acetylcholinesterase inhibitor.

In further embodiments, provided herein is a method of treating a patient exposed to a nerve agent, pesticide, or acetylcholinesterase inhibitor, such as an organophosphorus compound, e.g. a nerve agent such as sarin, or a pesticide. Also provided is a method of dephosphorylating phosphorylated acetylcholinesterase, e.g., in a patient. The methods comprise administering to the patient an amount of a 2-PAM analog compound as described herein effective to treat a patient for exposure to a organophosphorus nerve agent, pesticide, or acetylcholinesterase inhibitor, e.g., to dephosphorylate a phosphorylated active serine of acetylcholinesterase in a patient, or to improve one or more clinical symptoms of acetylcholinesterase inhibition in a patient, such as preventing seizures, respiratory arrest, and/or death, with the object or goal of thereby dephosphorylating a phosphorylated active serine of acetylcholinesterase in the patient, or improving one or more clinical symptoms of acetylcholinesterase inhibition in the patient, such as preventing seizures, respiratory arrest, and/or death.

EXAMPLES

The Examples below illustrate that that the 4- and 6-positions of 2-PAM tolerate structural perturbation without loss of potency. When the 4-position was endowed with hydroxyalkyl groups, these analogs showed equal potency to 2-PAM in vitro to rescue phosphylated acetylcholine esterase. When mice were injected with paraoxon, the described 2-PAM analogs showed similar or slightly better activity than 2-PAM.

General Procedures:
  Compounds:
  Compounds depicted in FIGS. 1-55 were synthesized. Selected examples of synthesis schemes are provided in the Examples below. NMR spectra are provided for selected synthesized compounds, and described intermediates were verified by NMR.
  Ellman's Assay:
  A solution of 1.20 mM reactivator in 100 mM phosphate pH 7.4 buffer (100 µL) was added to the wells of a clear 96-well plate. One hundred millimolar phosphate pH 7.4 buffer (50 µL) was added to the wells as the diluent, and two-fold serial dilutions of the reactivator were performed; the total volume of reactivator in the wells following the dilution was 50 µL. 1.02 mM Ellman's reagent (5,5'-dithiobis(2-nitrobenzoic acid) (DTNB)) in 100 mM phosphate pH 7.4 buffer (19.5 µL) and 1.36 mM acetylthiocholine iodide (ATCh) in 100 mM phosphate pH 7.4 buffer (19.5 µL) were transferred to the wells with the reactivator solutions.
  Separately, 100 U/mL human acetylcholinesterase (AChE) in 20 mM Tris pH 7.4 buffer (10 µL per well) was inhibited with 200 µM paraoxon-ethyl dissolved in isopropanol (1 µL per well). An additional aliquot of 100 U/mL human AChE (40 µL) was mock-inhibited with isopropanol (4 µL). After incubating for 10 min at 25° C., the inhibited enzyme solution (11 µL) was added to the wells containing the reactivator solution. The mock inhibited enzyme (11 µL) was added to wells containing 0 µM reactivator. Absorbance was measured at 405 nm in 5 min intervals in a Modulus II Microplate Multimode Reader.
  The data were then analyzed. The time point for the absorbance measurement was chosen as the time at which the samples containing 600 µM 2-PAM stopped increasing in absorbance. The background absorbance value was defined as the average of the absorbance values of the samples containing the inhibited human AChE and no reactivator. The background absorbance was subtracted from all samples. The absorbance values were then normalized by dividing by the average absorbance value of the samples containing the inhibited human AChE and the highest concentration of 2-PAM. The data were plotted using GraphPad Prism 7 software. $EC_{50}$ values were determined by fitting a sigmoidal curve to the data. Data for each reactivator were plotted with the data for 2-PAM as a reference.
  Inhibition of Acetylcholinesterase by the Reactivator:
  A solution of 0 or 1.2 mM reactivator in 100 mM phosphate pH 7.4 buffer (50 µL) was added to the wells. 0 or 100 U/mL human AChE in 20 mM Tris pH 7.4 buffer (10 µL) was added to the reactivators. The solutions were incubated at 24° C. for 10 min. A solution containing 500

μM DTNB and 650 μM ATCh in 100 mM pH 7.4 phosphate buffer (40 μL) was added to the wells, and the absorbance at 405 nm was measured in a Modulus II Microplate Multimode Reader. The data were plotted using GraphPad Prism 7 software. Data for each reactivator were plotted with the data for 2-PAM as a reference.

Inhibition of Acetylcholinesterase by the Reactivator:

0 or 200 μM reactivator in 1% v/v DMSO in 100 mM phosphate pH 7.4 buffer (50 μL) were added to the wells. 0 or 100 U/mL human AChE in 20 mM Tris pH 7.4 buffer (10 μL) was added to the reactivators. The solutions were incubated at 24° C. for 10 min. A solution containing 500 μM DTNB and 650 μM ATCh in 100 mM pH 7.4 phosphate buffer (40 μL) was added to the wells, and the absorbance at 405 nm was measured in a Modulus II Microplate Multimode Reader. The data were plotted using GraphPad Prism 7 software. Data for each reactivator were plotted with the data for 2-PAM as a reference.

Example 1

Preparation of 4-bromo-2-methylpyridine 1-oxide (RKB7036) 4-Bromo-2-methylpyridine 1-oxide was synthesized following the literature protocol found at *Chem. Eur. J.*, 2014, 20, 559-563: A 500-mL round-bottomed flask was charged with 4-bromo-2-methylpyridine (15.96 g, 92.75 mmol) and 2,2,2-trifluoro-1-phenylethanone (1.30 mL, 9.28 mmol, 10 mol %). Then, t-BuOH (46 mL), aqueous buffer solution (46 mL, 0.6 M $K_2CO_3/4\times10^{-5}$ M EDTA tetrasodium salt), MeCN (7.27 mL, 139 mmol, 1.5 equiv), and 30% aqueous $H_2O_2$ (31.6 mL, 232 mmol, 2.5 equiv) were added consecutively. The reaction mixture was left stirring for 21 h open to air at 22° C. After this period, the reaction was diluted with $H_2O$ (100 mL) and extracted with $CH_2Cl_2$ (3×100 mL) using a separatory funnel. The combined organic layers were dried over anhydrous $Na_2SO_4$, filtered, and concentrated in vacuo to give 4-bromo-2-methylpyridine 1-oxide as a pale-yellow oil. The conversion of the crude material was determined to be 76% by $^1H$ NMR, and the material was used directly in the next step without further purification.

Preparation of (4-bromopyridin-2-yl)methanol (RKB7118) A 1-L round-bottom flask with 4-bromo-2-methylpyridine 1-oxide (12.93 g, 68.71 mmol) was purged with nitrogen gas three times and charged with $CH_2Cl_2$ (200 mL). The reaction solution was cooled to 0° C. with an ice-water bath. TFAA (28.7 mL, 206 mmol, 3 equiv) in $CH_2Cl_2$ (60 mL) was added via addition funnel at 0° C. dropwise over 40 min. After the addition was complete, the temperature was raised to 22° C., and the reaction was stirred at the same temperature. After 44 h, t-BuOH (200 mL) and saturated aqueous $K_2CO_3$ (100 mL) were added at 23° C. After the reaction was stirred at the same temperature for 21 h, most of the organic solvent was removed in vacuo, and the resulting slurry was diluted with $H_2O$ and extracted with $CH_2Cl_2$ (3×200 mL) using a separatory funnel. The combined organic layers were dried over anhydrous $Na_2SO_4$, filtered, and concentrated in vacuo to give (4-bromopyridin-2-yl)methanol (10.12 g, 78% yield) as a gold oil that was 98% pure by $^1H$ NMR.

Preparation of 4-bromopicolinaldehyde (RKB7120) A 1-L round-bottomed flask with a reflux condenser was purged with nitrogen gas three times, and (4-bromopyridin-2-yl)methanol (10.07 g, 53.56 mmol), DCE (500 mL), and $MnO_2$ (27.94 g, 321.4 mmol, 6 equiv) were added consecutively. The mixture was heated to reflux. After 2 h, the reaction mixture was cooled to 23° C. filtered through Celite®, rinsed with EtOAc, and concentrated in vacuo. The crude material was combined with another batch prepared using the same procedure and purified by flash chromatography (40% EtOAc in hexanes) on silica gel (200 mL) to afford 4-bromopicolinaldehyde (8.88 g, 53% combined yield) as a red solid.

Preparation of 4-bromo-2-(dimethoxymethyl)pyridine (RKB7065) A 250-mL round-bottom flask with 4-bromopicolinaldehyde (6.96 g, 37.42 mmol) was charged with MeOH (50 mL) and 1.0 M $H_2SO_4$ in MeOH (41.2 mL, 41.2 mmol, 1.1 equiv). A reflux condenser was attached, and the solution was heated to reflux open to air. After 2 h, the reaction mixture was cooled to 23° C. and quenched with saturated aqueous $NaHCO_3$ (50 mL). The organic solvent was removed in vacuo, and the aqueous layer was extracted with EtOAc (3×50 mL) using a separatory funnel. The combined organic layers were dried over anhydrous $Na_2SO_4$, filtered, and concentrated in vacuo to give 4-bromo-2-(dimethoxymethyl)pyridine (6.88 g, 79% yield) as a yellow oil.

Preparation of 3-(2-(dimethoxymethyl)pyridin-4-yl) prop-2-yn-1-ol (RKB6154) A 25-mL round-bottom flask with 4-bromo-2-(dimethoxymethyl)pyridine (517 mg, 2.23 mmol) was purged with nitrogen gas three times, treated with $Pd(PPh_3)_2Cl_2$ (78.2 mg, 0.111 mmol, 5 mol %) and CuI (15.6 mg, 0.111 mmol. 5 mol %), and then purged again with nitrogen gas three times. The mixture was treated with anhydrous 1,4-dioxane (3 mL), $Et_3N$ (1.24 mL, 8.92 mmol, 4 equiv), and propargylic alcohol (198 μL, 3.345 mmol, 1.5 equiv) at 24° C. The resulting solution was heated to 50° C. (external temperature) and stirred. After 2 h, the reaction mixture was cooled to 24° C., and a small amount of charcoal was added. The mixture was filtered by gravity through filter paper, and the remaining residue was rinsed with EtOAc. The filtrate was partially concentrated in vacuo and purified directly by flash chromatography (40 to 80% EtOAc in hexanes with 3% MeOH) on silica gel (20 mL) to afford 3-(2-(dimethoxymethyl)pyridin-4-yl)prop-2-yn-1-ol (430 mg, 93% yield) as a brown oil.

Preparation of 3-(2-(dimethoxymethyl)pyridin-4-yl)propan-1-ol (RKB7285) A 100-mL round-bottom flask was charged with 3-(2-(dimethoxymethyl)pyridin-4-yl)prop-2-yn-1-ol (580 mg, 2.80 mmol), EtOH (14 mL), 5 wt. %, PVC (109 mg, 30.0 μmol, 1 mol %), and a few drops of AcOH at 23° C. The resulting suspension was purged with hydrogen gas three times and stirred vigorously at the same temperature for 17 h until the reaction was determined to be complete by TLC analysis. The suspension was filtered by gravity through filter paper, and the resulting filtrate was concentrated in vacuo. The crude material was purified by flash chromatography (40 to 80% EtOAc in hexanes with 1% MeOH) on silica gel (20 mL) to afford 3-(2-(dimethoxymethyl)pyridin-4-yl)propan-1-ol (340 mg, 56% yield) as a yellow oil.

Preparation of (E)-4-(3-hydroxypropyl)picolinaldehyde Oxime (RKB8089) A 25-mL round-bottomed flask open to air with 3-(2-(dimethoxymethyl)pyridin-4-yl)propan-1-ol (367 mg, 1.74 mmol) was charged with H$_2$O (2 mL) and 5.0 M H$_2$SO$_4$ in H$_2$O (380 µL, 1.91 mmol, 1.1 equiv). The solution was heated to 80° C. (external temperature). After stirring at the same temperature for 2 h, the reaction mixture was cooled to 23° C. and treated with K$_2$CO$_3$ (720 mg, 5.21 mmol, 3 equiv) followed by MeOH (10 mL) and NH$_2$OH·HCl (133 mg, 1.91 mmol, 1.1 equiv) at the same temperature. A reflux condenser was attached, and the reaction was heated to reflux while open to air. After 2 h, the reaction mixture was cooled to 23° C. and diluted with saturated aqueous NH$_4$Cl (10 mL). The resulting aqueous layer was extracted with EtOAc (3×10 mL) using a separatory funnel. The combined organic layers were dried over anhydrous Na$_2$SO$_4$, filtered, and concentrated in vacuo to afford (E)-4-(3-hydroxypropyl)picolinaldehyde oxime (215 mg, 69% yield) as a yellow solid that was 94% pure by $^1$H NMR.

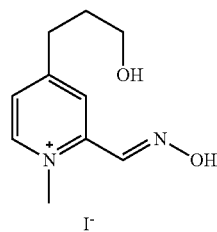

Figure 56:
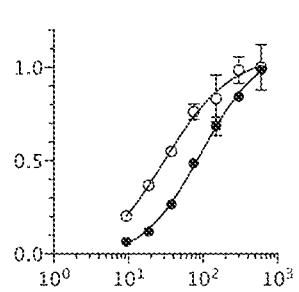
FIG. 56. Normalized AChE activity of RKB6186 compared to 2-PAM. $EC_{50}$(RKB6186)=94±1 μM; $EC_{50}$(2-PAM)=30±2 μM; $EC_{50}$ values are given as mean±SEM. Conditions: 0-600 μM RKB6186, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 57:
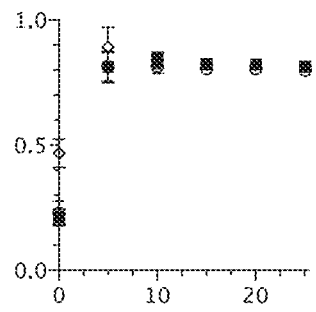
FIG. 57. Inhibition of human AChE by RKB6186. Conditions: 0 or 600 μM RKB6186, 10 U/mL human AChE, 200 μM DTNB, 267 μM ATCh, 9:1 100 mM phosphate pH 7.4:20 mM Tris pH 7.4.

Preparation of (E)-2-((hydroxyimino)methyl)-4-(3-hydroxypropyl)-1-methylpyridin-1-ium Iodide (RKB8064) A 25-mL sealed tube with (E)-4-(3-hydroxypropyl)picolinaldehyde oxime (494 mg, 2.77 mmol) was charged with acetone (10 mL) and MeI (6.34 mL, 102 mmol, 37 equiv). The vessel was sealed and heated to 70° C. (external temperature). After 8 h, the reaction mixture was cooled to 23° C., transferred to a 25-mL round-bottomed flask, concentrated in vacuo, and the resulting solid was recrystallized from hot EtOH (5 mL) to afford (E)-2-((hydroxyimino)methyl)-4-(3-hydroxypropyl)-1-methylpyridin-1-ium iodide (602 mg, 67% yield) as a red solid. In vitro data for (E)-2-((hydroxyimino)methyl)-4-(3-hydroxypropyl)-1-methylpyridin-1-ium iodide(RKB6186) is provided in FIGS. 56 and 57.

Example 2

Preparation of 4-(2-(dimethoxymethyl)pyridin-4-yl)but-3-yn-1-ol (RKB7260) A 50-mL round-bottom flask with 4-bromo-2-(dimethoxymethyl)pyridine (1.67 g, 7.19 mmol) was purged with nitrogen gas three times, treated with Pd(PPh$_3$)$_2$Cl$_2$ (252 mg, 0.359 mmol, 5 mol %) and CuI (50.4 mg, 0.359 mmol, 5 mol %), and then purged again with nitrogen gas three times. The mixture was treated with anhydrous 1,4-dioxane (10 mL), Et$_3$N (4.00 mL, 28.8 mmol, 4 equiv), and 3-butynyl-1-ol (820 µL, 10.8 mmol, 1.5 equiv) at 24° C. The resulting solution was heated to 50° C. and stirred. After 1 h, the reaction mixture was cooled to 24° C., and a small amount of charcoal was added. The mixture was filtered by gravity through filter paper, and the remaining residue was rinsed with EtOAc. The filtrate was partially concentrated in vacuo and purified directly by flash chromatography (40 to 90% EtOAc in hexanes with 3% MeOH) on silica gel (60 mL) to afford 4-(2-(dimethoxymethyl)pyridin-4-yl)but-3-yn-1-ol (1.33 g, 84% yield) as a brown oil.

Preparation of 4-(2-(dimethoxymethyl)pyridin-4-yl)butan-1-ol (RKB7261) A 250-mL round-bottom flask was charged with 4-(2-(dimethoxymethyl)pyridin-4-yl)but-3-yn-1-ol (1.18 g, 5.33 mmol), EtOH (30 mL), 5 wt. % PVC (218 mg, 50.0 µmol, 1 mol %), and a few drops of AcOH at 23° C. The resulting suspension was purged with hydrogen gas three times and stirred vigorously at the same temperature. After 1 h, more PVC (813 mg, 200 µmol, 4 mol %) was added and the suspension was purged again with hydrogen gas three times and stirred vigorously. After 2 h, the suspension was filtered by gravity through filter paper and concentrated in vacuo to deliver 4-(2-(dimethoxymethyl)pyridin-4-yl)butan-1-ol (1.17 g, 97% yield) as a yellow-brown oil. The material was used directly in the next step without further purification.

Preparation of 4-(4-hydroxybutyl)picolinaldehyde (RKB8025) A 50-mL round-bottomed flask open to air with 4-(2-(dimethoxymethyl)pyridin-4-yl)butan-1-ol (630 mg, 2.28 mmol) was charged with H$_2$O (20 mL) and 5.0 M H$_2$SO$_4$ in H$_2$O (615 µL, 3.08 mmol, 1.3 equiv). A reflux condenser was attached, and the solution was heated to reflux. After 3 h, the reaction mixture was cooled to 23° C., quenched with saturated aqueous NaHCO$_3$ (50 mL), and extracted with EtOAc (3×20 mL) using a separatory funnel. The combined organic layers were dried over anhydrous Na$_2$SO$_4$, filtered, and concentrated in vacuo. The crude material was combined with a second batch prepared following the same protocol and purified by flash chromatography (60 to 100% EtOAc in hexanes with 1% MeOH) on silica gel (60 mL) to afford 4-(4-hydroxybutyl)picolinaldehyde (862 mg, 77% combined yield) as a yellow oil.

Preparation of (E)-4-(4-hydroxybutyl)picolinaldehyde Oxime (RKB8026) A 25-mL round-bottomed flask that was open to air was charged with 4-(4-hydroxybutyl)picolinaldehyde (756 mg, 4.22 mmol), MeOH (8 mL), H$_2$O (2 mL), K$_2$CO$_3$ (1.11 g, 8.02 mmol, 1.9 equiv), and NH$_2$OH·HCl (323 mg, 4.64 mmol, 1.1 equiv). A reflux condenser was attached, and after the reaction mixture was heated to reflux for 2 h, the reaction mixture was cooled to 23° C. and diluted with 1.2 M pH 7.0 buffer (20 mL). The organic solvent was removed in vacuo, and the resulting aqueous layer was extracted with EtOAc (5×10 mL) using a separatory funnel. The combined organic layers were dried over anhydrous Na$_2$SO$_4$, filtered, and concentrated in vacuo to afford (E)-4-(4-hydroxybutyl) picolinaldehyde oxime (552 mg, 67% yield) which was more than 95% pure by $^1$H NMR.

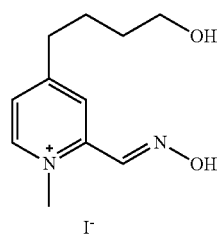

Preparation of (E)-4-(4-hydroxybutyl)-2-((hydroxyimino)methyl)-1-methylpyridin-1-ium Iodide (RKB8031) A 10-mL sealed tube with (E)-4-(4-hydroxybutyl)picolinaldehyde oxime (462 mg, 2.38 mmol) was charged with acetone (5 mL) and MeI (225 µL, 35.9 mmol, 15 equiv). The vessel was sealed and heated to 85° C. (external temperature). After 8 h at the same temperature, the reaction mixture was cooled to 23° C., transferred to a 25-mL round-bottomed flask, concentrated, and the resulting solid was recrystallized from hot EtOH (10 mL) to afford (E)-4-(4-hydroxybutyl)-2-((hydroxyimino)methyl)-1-methylpyridin-1-ium iodide (408 mg. 51% yield) as a brown solid.

Figure 58:
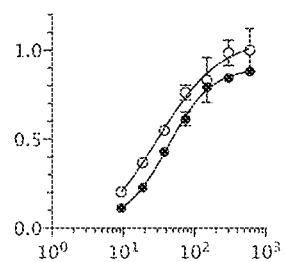
FIG. 58. Normalized AChE activity of RKB6259 compared to 2-PAM. $EC_{50}$(RKB6259)=43±1 μM; $EC_{50}$(2-PAM)=30±2 μM; $EC_{50}$ values are given as mean±SEM. Conditions: 0-600 μM RKB6259, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 59:
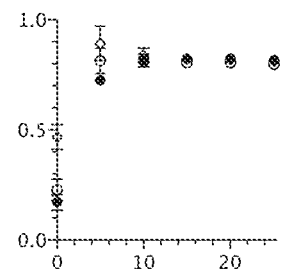
FIG. 59. Inhibition of human AChE by RKB6259. Conditions: 0 or 600 μM RKB6259, 10 U/mL human AChE, 200 μM DTNB, 267 μM ATCh, 9:1 100 mM phosphate pH 7.4:20 mM Tris pH 7.4.

In vitro data for (E)-4-(4-hydroxybutyl)-2-((hydroxyimino)methyl)-1-methylpyridin-1-ium iodide(RKB6259) is provided in FIGS. 58 and 59.

Figure 60:
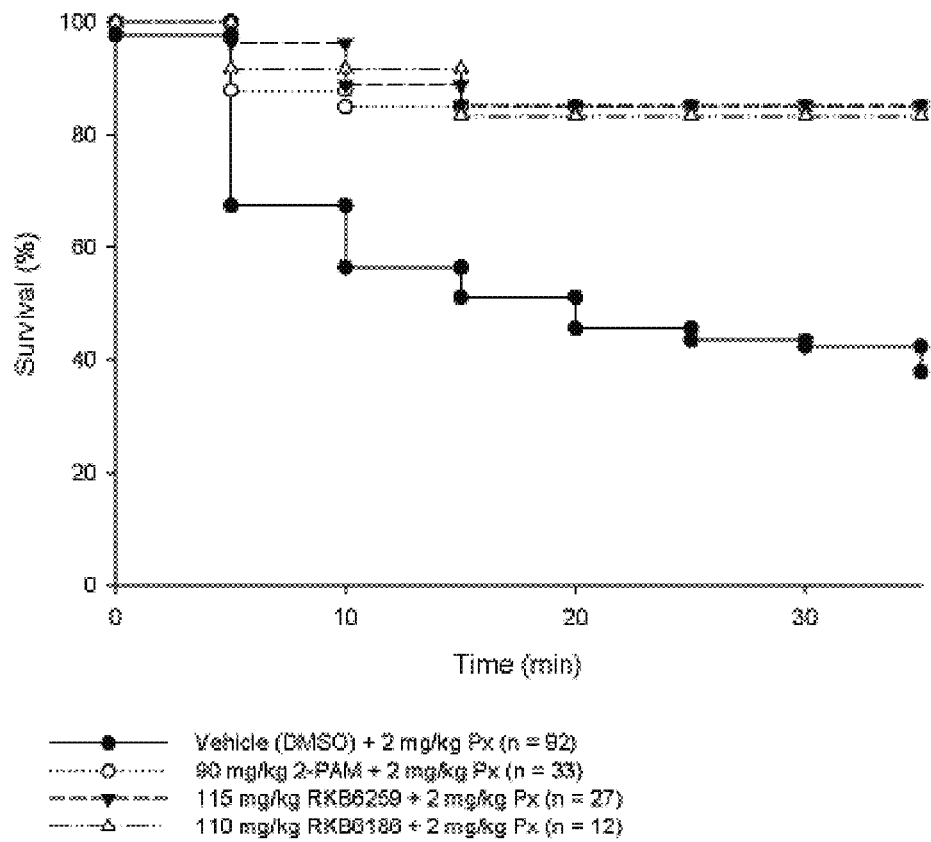
FIG. 60 provides a graph showing survival (%) with 2 mg/kg paraoxon and vehicle, 2-PAM, RKB6259, and RKB6186.

Animal Study Data:

Male C57BL/6J 9-11 week old mice (Jackson Labs) were injected intraperitoneally (i.p.) with 2 mg/kg paraoxon-ethyl (Sigma cat. No 36186), followed immediately by i.p. injection of 90 mg/kg 2-PAM (Sigma cat. No P60205) or 115 mg/kg RKB6259 or 110 mg/kg RKB6186 or vehicle (DMSO). Injection volume of paraoxon-ethyl was 60 µL, and of treatments was 100 µL. All solutions were prepared the same day as injection. Mice were housed 4 per cage and observed for 35 min post-injection. Time of death and signs of toxicity (straub tail, immobility, tremor, dyspnea, etc.) were recorded. A single exposure group was normally comprised of 6-12 mice. See, FIG. 60.

Example 3

Preparation of 2-(dimethoxymethyl)-4-phenylpyridine (RKB8048) A 150-mL sealed tube with 4-bromo-2-(dimethoxymethyl)pyridine (1.27 g, 5.47 mmol) was charged with toluene (37 mL), H$_2$O (12 mL), K$_2$CO$_3$ (3.02 g, 21.9 mmol, 4 equiv), Pd(OAc)$_2$ (61.4 mg, 274 µmol, 5 mol %), PPh$_3$ (287 mg, 1.09 mmol, 20 mol %) and phenyl boronic acid (1.00 g, 8.20 mmol, 1.5 equiv). The vessel was sealed and the reaction mixture was heated to 110° C. (external temperature). After 45 h, the reaction mixture was cooled to 23° C. and extracted with EtOAc (3×10 mL) using a separatory funnel. The combined organic layers were washed with brine (20 mL), dried over anhydrous Na$_2$SO$_4$, filtered, and concentrated in vacuo. The crude material was purified by flash chromatography (20 to 55% EtOAc in hexanes) on silica gel (60 mL) to afford 2-(dimethoxymethyl)-4-phenylpyridine (955 mg, 76% yield) as an orange oil.

Preparation of 4-phenylpicolinaldehyde (RKB8049) A 50-mL round-bottomed flask that was open to air with 2-(dimethoxymethyl)-4-phenylpyridine (805 mg, 3.50 mmol) was charged with H$_2$O (20 mL) and H$_2$SO$_4$ in H$_2$O (772 µL, 5 M, 3.86 mmol, 1.2 equiv). The reaction mixture was heated to 80° C. After 2 h, the reaction mixture was cooled to 23° C., quenched with saturated aqueous NaHCO$_3$ (10 mL) and extracted with EtOAc (3×10 mL) using a separatory funnel. The combined organic layers were washed with brine (20 mL), dried over anhydrous Na$_2$SO$_4$, filtered, and concentrated in vacuo. The crude material was purified by flash chromatography (20% EtOAc in hexanes) on silica gel (40 mL) to afford 4-phenylpicolinaldehyde (526 mg. 82% yield) as white solid.

Preparation of (E)-4-phenylpicolinaldehyde Oxime (RKB8050) A 50-mL round-bottomed flask that was open to air with 4-phenylpicolinaldehyde (351 mg, 1.91 mmol) was charged with MeOH (12 mL), H$_2$O (1 mL), K$_2$CO$_3$ (396 mg, 2.87 mmol, 1.9 equiv) and NH$_2$OH·HCl (133 mg, 1.91 mmol). A reflux condenser was attached and the reaction mixture was heated to reflux. After 90 min, the reaction mixture was cooled to 23° C. and diluted with pH 7.0 buffer (10 mL, 1.2 M). The organic solvent was removed in vacuo and the resulting aqueous layer was extracted with EtOAc (3×10 mL) using a separatory funnel. The combined organic layers were washed with brine (20 mL), dried over anhydrous Na$_2$SO$_4$, filtered, and concentrated in vacuo to afford (E)-4-phenylpicolinaldehyde oxime (370 mg, 98% yield) as a white solid which was pure by $^1$H NMR.

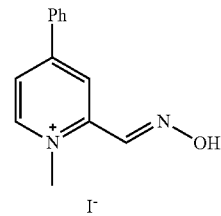 [SMILES: C[n+]1ccc(-c2ccccc2)cc1/C=N/O ; [I-]]

Figure 61:
FIG. 61. Normalized AChE activity of RKB6242 compared to 2-PAM. $EC_{50}$(RKB6242)=69±1 μM; $EC_{50}$(2-PAM)=30±2 μM; $EC_{50}$ values are given as mean±SEM. Conditions: 0-600 μM RKB6242, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 62:
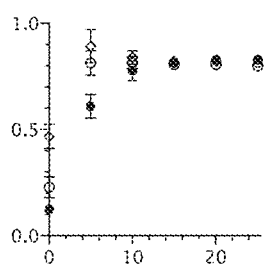
FIG. 62. Inhibition of human AChE by RKB6242. Conditions: 0 or 600 μM RKB6242, 10 U/mL human AChE, 200 μM DTNB, 267 μM ATCh, 9:1 100 mM phosphate pH 7.4:20 mM Tris pH 7.4.

Preparation of (E)-2-((hydroxyimino)methyl)-1-methyl-4-phenylpyridin-1-ium Iodide (RKB8051) A 10-mL sealed tube with (E)-4-phenylpicolinaldehyde oxime (180 mg, 910 µmol) was charged with acetone (1 mL) and MeI (113 µL, 1.81 mmol, 2 equiv). The vessel was sealed and heated to 68° C. After 6 h, the reaction mixture was cooled to 23° C., concentrated in vacuo, and the resulting solid was recrystallized from hot EtOH (30 mL) to afford (E)-2-((hydroxyimino)methyl)-1-methyl-4-phenylpyridin-1-ium iodide (297 mg, 96% yield) as fluffy orange crystals. Data is provided in FIGS. 61 and 62.

Example 4

Preparation of (4-ethoxypyridin-2-yl)methanol (RKB6223) A 100-mL round-bottomed flask open to air was charged with (4-nitropyridin-2-yl)methanol (1.03 g, 6.69 mmol), EtOH (17 mL), and EtONa (1.73 g, 25.4 mmol, 3.8 equiv). The vessel was fitted with a reflux condenser and heated to reflux. After 15 h, more EtONa (2.52 g, 37.0 mmol, 5.5 equiv) was added, and the reaction mixture was let stir at reflux. After 3 h, the reaction mixture was cooled to 23° C. and neutralized with aqueous 4.0 M HCl. The mixture was concentrated in vacuo to remove organic solvent and then dissolved in saturated aqueous NaHCO₃. The resulting aqueous layer was extracted with CH₂Cl₂ (3×30 mL) using a reparatory funnel. The combined organic layers were dried over anhydrous Na₂SO₄, filtered, and concentrated in vacuo to afford (4-ethoxypyridin-2-yl)methanol (1.03 g, quantitative yield) as a red solid which was pure by ¹H NMR.

Preparation of 4-ethoxypicolinaldehyde (RKB8044) A 100-mL round-bottomed flask that was purged with nitrogen gas three times was charged with (4-ethoxypyridin-2-yl)methanol (337 mg, 2.20 mmol), DCE (10 mL), and MnO₂ (541 mg, 6.60 mmol, 3 equiv). The vessel was fitted with a reflux condenser and heated to reflux. After 2 h, the slurry was cooled to 23° C. and filtered through Celite®, rinsed with CH₂Cl₂, and concentrated in vacuo. The crude material was purified by flash chromatography (40% EtOAc in hexanes) on silica gel (30 mL) to afford 4-ethoxypicolinaldehyde (187 mg, 56% yield) as a yellow oil.

Preparation of (E)-4-ethoxypicolinaldehyde Oxime (RKB6228) A 100-mL round-bottomed flask that was open to air was charged with 4-ethoxypicolinaldehyde (716 mg, 4.74 mmol 1 equiv), MeOH (50 mL), H₂O (5 mL), K₂CO₃ (983 mg, 7.11 mmol, 1.5 equiv), and NH₂OH·HCl (311 mg, 4.47 mmol, 1 equiv). A reflux condenser was attached, and after the reaction mixture was heated to reflux for 1 h, the reaction mixture was cooled to 23° C. and diluted with 1.2 M pH 7.0 buffer (20 mL). The organic solvent was removed in vacuo, and the resulting aqueous layer was extracted with CH₂Cl₂ (3×20 mL) using a reparatory funnel. The combined organic layers were dried over anhydrous Na₂SO₄, filtered, and concentrated in vacuo to afford (E)-4-ethoxypicolinaldehyde oxime (573 mg, 73% yield) as a yellow-white solid that was used directly without further purification.

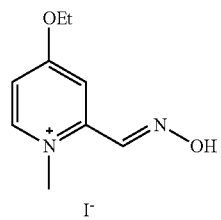

Preparation of (E)-4-ethoxy-2-((hydroxyimino) methyl)-1-methylpyridin-1-ium Iodide (RKB6229) A 5-mL sealed tube with (E)-4-ethoxypicolinaldehyde oxime (69.5 mg, 0.418 mmol) was charged with acetone (500 μL) and MeI (500 μL, 8.07 mmol, 19 equiv). The vessel was sealed and heated to 80° C. After 1 h, the reaction mixture was cooled to 23° C. and a small amount of charcoal was added. The mixture was filtered by gravity through filter paper, the remaining residue was rinsed with EtOAc, and concentrated in vacuo to afford (E)-4-ethoxy-2-((hydroxyimino)methyl)-1-methylpyridin-1-ium iodide (94.6 mg, 73% yield) as a yellow solid.

Figure 63:
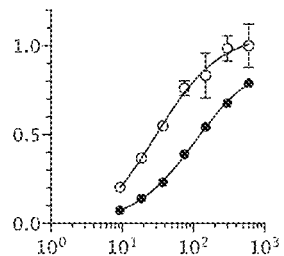
FIG. 63. Normalized AChE activity of RKB6229 compared to 2-PAM. $EC_{50}$(RKB6229)=106±1 μM; $EC_{50}$(2-PAM)=30±2 μM; $EC_{50}$ values are given as mean±SEM. Conditions: 0-600 μM RKB6229, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 64:
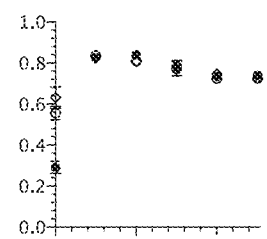
FIG. 64. Inhibition of human AChE by RKB6229. Conditions: 0 or 600 μM RKB6229, 10 U/mL human AChE, 200 μM DTNB, 267 μM ATCh, 9:1 100 mM phosphate pH 7.4:20 mM Tris pH 7.4.

In vitro data for (E)-4-ethoxy-2-((hydroxyimino)methyl)-1-methylpyridin-1-ium iodide is provided in FIGS. 63 and 64.

Example 5

Preparation of (4-(2,2,2-trifluoroethoxy)pyridin-2-yl)methanol (RKB6214) A 100-mL round-bottom flask was charged with (4-nitropyridin-2-yl)methanol (1.02 g, 6.63 mmol), CF₃CH₂OH (17 mL), and CF₃CH₂ONa (3.07 g, 25.2 mmol, 3.8 equiv, prepared from CF₃CH₂OH and NaH). A reflux condenser was attached, and after the reaction mixture was heated to reflux for 14 h, the reaction mixture was cooled to 23° C., and additional CF₃CH₂ONa (2.04 g, 16.7 mmol, 2.5 equiv) was added. The reaction mixture was heated to reflux for 24 h, cooled to 23° C., and neutralized with aqueous 4.0 M HCl. The mixture was concentrated in vacuo. The resulting residue was dissolved in saturated aqueous NaHCO₃, and the product was extracted with EtOAc (3×30 mL) using a separatory funnel. The combine organic layers were dried over anhydrous Na₂SO₄, filtered, and concentrated in vacuo to deliver (4-(2,2,2-trifluoroethoxy)pyridin-2-yl)methanol (1.08 g, 79% yield).

Preparation of 4-(2,2,2-trifluoroethoxy)picolinaldehyde (RKB6215) A 250-mL round-bottomed flask with a reflux condenser was purged with nitrogen gas three times, and (4-(2,2,2-trifluoroethoxy)pyridin-2-yl)methanol (964 mg, 4.65 mmol, 1 equiv), DCE (60 mL), and MnO₂ (2.43 g, 27.9 mmol, 6 equiv) were added consecutively. The mixture was heated to reflux. After 3 h, the reaction mixture was cooled to 23° C., filtered through Celite®, rinsed with EtOAc, and concentrated in vacuo to afford 4-(2,2,2-trifluoroethoxy) picolinaldehyde (669 mg, 70% yield).

Preparation of (E)-4-(2,2,2-trifluoroethoxy)picolinaldehyde oxime (RKB6219) A 25-mL round-bottomed flask that was open to air was charged with 4-(2,2,2-trifluoroethoxy)picolinaldehyde (669 mg, 3.26 mmol), MeOH (50 mL), H₂O (5 mL), K₂CO₃ (676 mg, 4.89 mmol, 1.5 equiv), and NH₂OH·HCl (227 mg, 3.26 mmol, equiv). A reflux condenser was attached, and after the reaction mixture was heated to reflux for 1 h, the reaction mixture was cooled to 23° C. and diluted with 1.2 M pH 7.0 buffer (20 mL). The organic solvent was removed in vacuo, and the resulting aqueous layer was extracted with EtOAc (3×20 mL) using a separatory funnel. The combined organic layers were dried over anhydrous Na₂SO₄, filtered, and concentrated in vacuo to afford (E)-4-(2,2,2-trifluoroethoxy)picolinaldehyde oxime (555 mg, 77% yield).

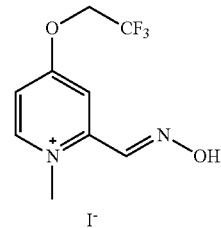 [SMILES: C[n+]1ccc(OCC(F)(F)F)cc1/C=N/O ; [I-]]

Figure 65:
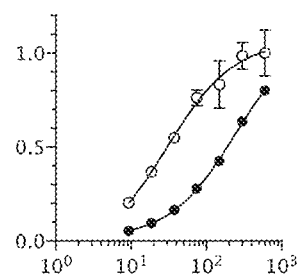
FIG. 65. Normalized AChE activity of RKB6220 compared to 2-PAM. $EC_{50}$(RKB6220)=240±1 μM; $EC_{50}$(2-PAM)=30±2 μM; $EC_{50}$ values are given as mean±SEM. Conditions: 0-600 μM RKB6220, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 66:
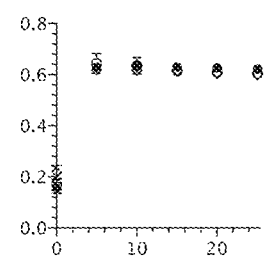
FIG. 66. Inhibition of human AChE by RKB6220. Conditions: 0 or 100 μM RKB6220, 10 U/mL human AChE, 200 μM DTNB, 267 μM ATCh, 9:1 100 mM phosphate pH 7.4:20 mM Tris pH 7.4.

Preparation of (E)-2-((hydroxyimino)methyl)-1-methyl-4-(2,2,2-trifluoroethoxy)pyridin-1-ium Iodide (RKB6220) A 10-mL sealed tube with (E)-4-(2,2,2-trifluoroethoxy)picolinaldehyde oxime (424 mg, 1.92 mmol) was charged with acetone (1 mL) and MeI (1.20 mL, 19.4 mmol, 10 equiv). The vessel was sealed and heated to 60° C. (external temperature). After 3 h at the same temperature, the reaction mixture was cooled to 23° C., and concentrated in vacuo to afford (E)-2-((hydroxyimino)methyl)-1-methyl-4-(2,2,2-trifluoroethoxy)pyridin-1-ium iodide (288 mg, 41% yield) as a brown solid. In vitro data for (E)-2-((hydroxyimino)methyl)-1-methyl-4-(2,2,2-trifluoroethoxy)pyridin-1-ium iodide is provided in FIGS. 65 and 66.

Example 6

Preparation of (4-(prop-2-yn-1-yloxy)pyridin-2-yl)methanol (RK B6278) A 50-mL round-bottom flask was charged with (4-nitropyridin-2-yl)methanol (1.07 g, 6.94 mmol), propargyl alcohol (5 mL), and the sodium alkoxide of propargyl alcohol (2.22 g, 28.44 mmol, 4.1 equiv, prepared from propargylic alcohol and NaH). A reflux condenser was attached, and after the reaction mixture was heated to reflux for 2 h, the reaction mixture was cooled to 23° C., quenched with saturated aqueous NH$_4$Cl (5 mL), and extracted with CH$_2$Cl$_2$ (3×10 mL) using a separatory funnel. The combine organic layers were dried over anhydrous Na$_2$SO$_4$, filtered, and concentrated in vacuo to deliver (4-(prop-2-yn-1-yloxy)pyridin-2-yl)methanol (830 mg, 73% yield). The crude material was used directly in the next step without further purification.

Preparation of 4-(prop-2-yn-1-yloxy)picolinaldehyde (RKB6279) A 250-mL round-bottomed flask with a reflux condenser was purged with nitrogen gas three times, and (4-(prop-2-yn-1-yloxy)pyridin-2-yl)methanol (830 mg, 5.09 mmol), DCE (63 mL), and MnO$_2$ (2.65 g, 30.53 mmol, 6 equiv) were added consecutively. The mixture was heated to reflux. After 4 h, the reaction mixture was cooled to 23° C., filtered through Celite®, rinsed with EtOAc, and concentrated in vacuo. The crude material was purified by flash chromatography (40% EtOAc in hexanes) on silica gel (40 mL) to afford 4-(prop-2-yn-1-yloxy)picolinaldehyde (180 mg, 22% yield) as white-orange crystals.

Preparation of (E)-4-(prop-2-yn-1-yloxy)picolinaldehyde oxime (RKB6282) A 100-mL round-bottomed that was open to air flask with 4-(prop-2-yn-1-yloxy)picolinaldehyde (154 mg, 0.956 mmol) was charged with MeOH (20 mL), H$_2$O (2 mL), K$_2$CO$_3$ (276 mg, 2.0 mmol, 2 equiv) and NH$_2$OH·HCl (72.7 mg, 1.05 mmol, 1.1 equiv). A reflux condenser was attached and the reaction mixture was heated to reflux. After 1 h, the reaction mixture was cooled to 23° C. and diluted with 1.2 M pH 7.0 buffer (20 mL), The organic solvent was removed in vacuo and the resulting aqueous layer was extracted with EtOAc (3×15 mL) using a separatory funnel. The combined organic layers were dried over anhydrous Na$_2$SO$_4$, filtered, and concentrated in vacuo to afford (E)-4-(prop-2-yn-1-yloxy)picolinaldehyde oxime (159 mg, 95% yield) as a cream-colored powder which was pure by $^1$H NMR.

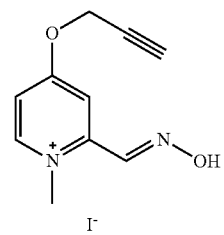

Figure 67:
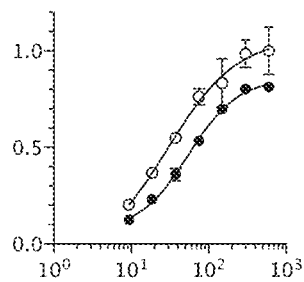
FIG. 67. Normalized AChE activity of RKB6284 compared to 2-PAM. $EC_{50}$(RKB6284)=55±1 μM; $EC_{50}$(2-PAM)=30±2 μM; $EC_{50}$ values are given as mean±SEM. Conditions: 0-600 μM RKB6284, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 68:
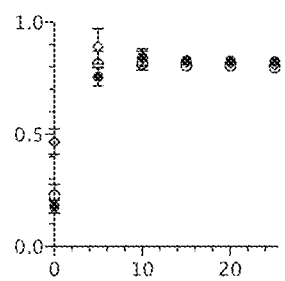
FIG. 68. Inhibition of human AChE by RKB6284. Conditions: 0 or 600 μM RKB6284, 10 U/mL human AChE, 200 μM DTNB, 267 μM ATCh, 9:1 100 mM phosphate pH 7.4:20 mM Tris pH 7.4.

Preparation of (E)-2-((hydroxyimino)methyl)-1-methyl-4-(prop-2-yn-1-yloxy)pyridin-1-ium Iodide (RKB6284) A 10-mL sealed tube with (E)-4-(prop-2-yn-1-yloxy)picolinaldehyde oxime (55.9 mg, 0.32 mmol) was charged with acetone (500 and MeI (491 µL, 7.93 mmol, 25 equiv). The vessel was sealed and heated to 70° C. After 2 h, the reaction mixture was cooled to 23° C., passed through a C18 column and concentrated in vacuo to afford (E)-2-((hydroxyimino)methyl)-1-methyl-4-(prop-2-yn-1-yloxy)pyridin-1-ium iodide (93.2 mg, 92% yield) as golden-colored crystals. In vitro data for (E)-2-((hydroxyimino)methyl)-1-methyl-4-(prop-2-yn-1-yloxy)pyridin-1-ium iodide is provided in FIGS. 67 and 68.

Example 7

Preparation of 2-(dimethoxymethyl)-4-(ethylthio)pyridine (RKB7067) A 10-mL sealed tube with 4-bromo-2-(dimethoxymethyl)pyridine (658 mg, 2.84 mmol) was charged with DMSO (1.42 mL), K$_2$CO$_3$ (432 mg, 3.12 mmol, 1.1 equiv), and EtSH (1.06 L, 14.2 mmol, 5 equiv). The vessel was sealed and heated to 85° C. After 18 h, the reaction mixture was cooled to 23° C., diluted with H$_2$O (30 mL), extracted with CH$_2$Cl$_2$ (10 mL, 2×), and the combined organic layers were dried over anhydrous Na$_2$SO$_4$, filtered, and concentrated in vacuo. The crude material was purified by flash chromatography (20-50% EtOAc in hexanes) on silica gel (40 mL) to afford 2-(dimethoxymethyl)-4-(ethylthio)pyridine (284 mg, 47% yield) as a yellow oil.

Preparation of 4-(ethylthio)picolinaldehyde (RKB8055) A 25-mL round-bottomed flask that was open to air with 2-(dimethoxymethyl)-4-(ethylthio)pyridine (220 mg, 1.03 mmol) was charged with H$_2$O (12 mL) and 5.0 M H$_2$SO$_4$ in H$_2$O (228 µL, 1.14 mmol, 1.1 equiv). The reaction mixture was heated to 80° C. After 4 h, the reaction mixture was cooled to 23° C., quenched with saturated aqueous NaHCO$_3$ (10 mL), and extracted with EtOAc (3×10 mL) using a separatory funnel. The combined organic layers were washed with brine (10 mL), dried over anhydrous Na$_2$SO$_4$, filtered, and concentrated in vacuo to afford 4-(ethylthio)picolinaldehyde (167 mg, 96% yield) as a yellow oil that was pure by $^1$H NMR.

Preparation of (E)-4-(ethylthio)picolinaldehyde Oxime (RKB8056) A 50-mL round-bottomed flask that was open to air with 4-(ethylthio)picolinaldehyde (113 mg, 0.67 mmol) was charged with MeOH (8 mL), H$_2$O (2 mL), K$_2$CO$_3$ (177 mg, 1.28 mmol, 1.9 equiv) and NH$_2$OH·HCl (51.4 mg, 0.74 mmol, 1.1 equiv). A reflux condenser was attached and the reaction mixture was heated to reflux. After 2 h, the reaction mixture was cooled to 23° C. and diluted with pH 7.0 buffer (8 mL, 1.2 M). The organic solvent was removed in vacuo and the resulting aqueous layer was extracted with EtOAc (3×8 mL) using a separatory funnel. The combined organic layers were washed with brine (5 mL), dried over anhydrous Na$_2$SO$_4$, filtered, and concentrated in vacuo to afford (E)-4-(ethylthio)picolinaldehyde oxime (122 mg, 99% yield) as a white solid which was pure by $^1$H NMR.

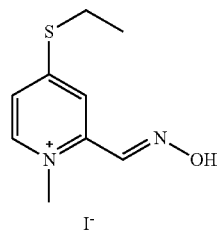

Preparation of (E)-4-(ethylthio)-2-((hydroxyimino)methyl)-1-methylpyridin-1-ium Iodide (RKB8057) A 25-mL sealed tube with (E)-4-(ethylthio)picolinaldehyde oxime (89.3 mg, 0.49 mmol) was charged with acetone (500 μL) and MeI (62.0 μL, 1.0 mmol, 2 equiv). The vessel was sealed and heated to 70° C. (external temperature). After 5 h, the reaction mixture was cooled to 23° C., concentrated in vacuo, and the conversion was determined to be 65% by $^1$H NMR. The crude material was returned to the sealed tube with acetone (1.0 mL) and MeI (150.0 μL, 2.55 mmol, 5 equiv). The vessel was sealed and heated to 70° C. After 4 h, the reaction mixture was cooled to 23° C., concentrated in vacuo, and the resulting solid was recrystallized from hot EtOH (5 mL) to afford (E)-4-(ethylthio)-2-((hydroxyimino)methyl)-1-methylpyridin-1-ium iodide (86.7 mg, 55% yield) as a light-brown powder.

Figure 69:
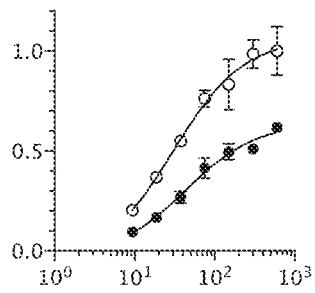
FIG. 69. Normalized AChE activity of RKB7070 compared to 2-PAM. $EC_{50}$(RKB7070)=43±1 μM; $EC_{50}$(2-PAM)=30±2 μM; $EC_{50}$ values are given as mean±SEM. Conditions: 0-600 μM RKB7070, 10 U/mL human AChE, 200 μM DTNB, 267 μM ATCh, 20 μM paraoxon-ethyl, 1:89:10 isopropanol:100 mM phosphate pH 7.4:20 mM Tris pH 7.4.
Figure 70:
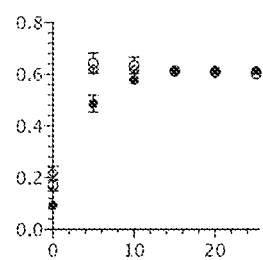
FIG. 70. Inhibition of human AChE by RKB7070. Conditions: 0 or 100 μM RKB7070, 10 U/mL human AChE, 200 μM DTNB, 267 μM ATCh, 9:1 100 mM phosphate pH 7.4:20 mM Tris pH 7.4.

In vitro data for (E)-4-(ethylthio)-2-((hydroxyimino)methyl)-1-methylpyridin-1-ium iodide is provided in FIGS. 69 and 70.

Example 8

Preparation of 2,4-dimethylpyridine N-oxide (ADG2072) 2,4-Dimethylpyridine N-oxide was synthesized following the literature protocol found at Chem.-Eur. J, 2014, 20, 559-563: A 500-mL pear-shaped flask was charged with 2,4-lutidine (4.8 mL, 44.8 mmol) at 23° C. under an open atmosphere. Aqueous 0.6 M K$_2$CO$_3$ (22 mL), t-BuOH (22 mL), MeCN (3.5 mL, 67 mmol, 1.5 equiv), 30% aqueous H$_2$O$_2$ (27.0 mL, 135 mmol, 3 equiv), and 2,2,2-trifluoroacetophenone (620 μL, 4.48 mmol, 10 mol %) were added sequentially in one portion, and the reaction mixture continued to stir at 23° C. under an open atmosphere for 27 h. After this period, H$_2$O (25 mL) was added, and the resulting reaction mixture was allowed to stir for 2 h at 23° C. under an open atmosphere. The reaction mixture was extracted with CH$_2$Cl$_2$ (4×30 mL) using a separatory funnel. The combined organic layers were dried over anhydrous Na$_2$SO$_4$, filtered, and concentrated in vacuo. The crude residue was purified by flash chromatography (60 to 100% EtOAc in hexanes) on silica gel (110 mL) to afford 2,4-dimethylpyridine N-oxide as a yellow oil (3.56 g, 65% yield).

Preparation of (4-methylpyridin-2-yl)methanol (ADG2075) A 200-mL pear-shaped flask with 2,4-lutidine N-oxide (1.98 g, 16.1 mmol) was purged with nitrogen gas three times and charged with CH$_2$Cl$_2$ (25 mL) at 23° C. TFAA (6.8 mL, 48 mmol, 3 equiv) in CH$_2$Cl$_2$ (18 mL) was added, and the resulting reaction mixture was stirred at 23° C. for 48 h. After this period, the reaction mixture was cooled to 0° C. Then, t-BuOH (10 mL) and saturated aqueous K$_2$CO$_3$ (10 mL) were added to the reaction mixture. The resulting mixture was stirred for 20 h and gradually warmed to 23° C. The mixture was extracted with CH$_2$Cl$_2$ (3×20 mL) using a separatory funnel. The combined organic layers were dried over anhydrous Na$_2$SO$_4$, filtered, and concentrated in vacuo. The resulting crude residue was purified by flash chromatography (50 to 95% EtOAc in hexanes) on silica gel (60 mL) to afford (4-methylpyridin-2-yl)methanol as a dark brown oil (1.16 g, 51% yield).

Preparation of 4-methylpicolinaldehyde (ADG2076) A 50-mL pear-shaped flask with a reflux condenser was purged with nitrogen gas three times, and (4-methylpyridin-2-yl)methanol (780 mg, 6.28 mmol), DCE (27 mL), and MnO$_2$ (2.73 g, 31.4 mmol, 5 equiv) were added consecutively. The mixture was heated to reflux. After 13 h, the reaction mixture was cooled to 23° C., filtered through Celite®, washed with EtOAc, and concentrated in vacuo. The crude residue was purified by flash chromatography (40 to 70% EtOAc in hexanes) on silica gel (50 mL) to afford 4-methylpicolinaldehyde as a yellow oil (462 mg, 60% yield).

Preparation of (E)-4-methylpicolinaldehyde Oxime (ADG2077) A 50-mL pear-shaped flask open to air was charged with 4-methylpicolinaldehyde (312 mg. 2.57 mmol), MeOH (26 mL), H$_2$O (4 mL), K$_2$CO$_3$ (427 mg, 3.08 mmol, 1.2 equiv), and NH$_2$OH·HCl (179 mg, 2.57 mmol, 1 equiv). A reflux condenser was attached, and after the reaction mixture was heated to reflux for 4 h, the reaction mixture was cooled to 23° C. The organic solvent was removed in vacuo and the resulting aqueous layer was extracted with EtOAc (3×30 mL) using a separatory funnel. The combined organic layers were dried over anhydrous Na$_2$SO$_4$, filtered, and concentrated in vacuo to afford (E)-4-methylpicolinaldehyde oxime as a light brown solid (303 mg, 86% yield). This material was used directly without further purification.

Preparation of (E)-2-((hydroxyimino)methyl)-1,4-dimethylpyridin-1-ium Iodide (ADG2078) A 10-mL sealed tube with (E)-4-methylpicolinaldehyde oxime (202 mg, 1.48 mmol) was charged with acetone (3 mL) and MeI (978 μL, 14.8 mmol, 10 equiv). The vessel was sealed and heated to 45° C. (external temperature). After 20 h at the same temperature, the reaction mixture was cooled to 23° C. A small amount of charcoal was added and the mixture was stirred for 4 h at 23° C. The mixture was filtered by gravity through filter paper, and the remaining residue was rinsed with MeOH. The filtrate was concentrated in vacuo to yield (E)-2-[(hydroxyimino)methyl]-1,4-dimethylpyridin-1-ium N-methyl oxime as a light brown solid (295 mg, 72% yield).

Figure 71:
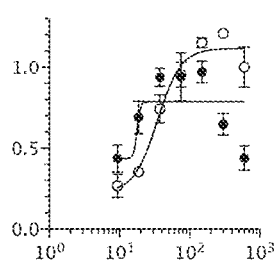
FIG. 71. *Electrophorus electricus* (electric eel) AChE activity of (E)-2-[(hydroxyimino)methyl]-1,4-dimethylpyridin-1-ium (ADG2078) compared to 2-PAM at 20 minutes. $EC_{50}$(ADG2078)=18±1 μM; $EC_{50}$ (2-PAM)=34±1 μM; $EC_{50}$ values are given as mean±SEM. Conditions: 0-600 μM ADG2078, 10 U/mL eel AChE. 200 μM DTNB, 267 μM ATCh, 20 μM paraoxon-methyl, 1:89:10 (v/v) isopropanol: 100 mM phosphate pH 7.4:20 mM Tris pH 7.4.
Figure 72:
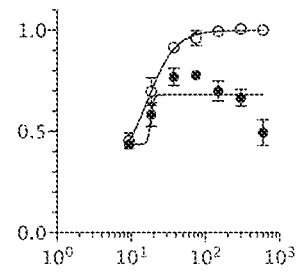
FIG. 72. *Electrophorus electricus* (electric eel) AChE activity of (E)-2-[(hydroxyimino)methyl]-1,4-dimethylpyridin-1-ium (ADG2078) compared to 2-PAM at 20 minutes, EC50(ADG2078)=18±1 μM; EC50 (2-PAM)=16±1 μM; EC50 values are given as mean±SEM. Conditions: 0-600 μM ADG2078, 10 U/mL eel AChE, 200 μM DTNB, 267 μM ATCh, 20 μM paraoxon-ethyl, 1:89:10 (v/v) isopropanol: 100 mM phosphate pH 7.4:20 mM Tris pH 7.4.
Figure 73:
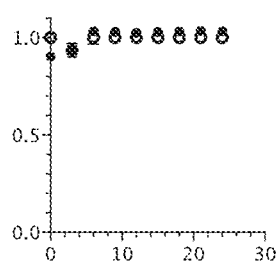
FIG. 73. Inhibition of *Electrophorus electricus* (electric eel) AChE by (E)-2-[(hydroxyimino)methyl]-1,4-dimethylpyridin-1-ium (ADG2078). Conditions: 0 or 600 μM ADG2078, 10 U/mL eel AChE, 200 μM DTNB, 267 μM ATCh, 9:1 (v/v) 100 mM phosphate pH 7.4:20 mM Tris pH 7.4.

In vitro data for (E)-2-((hydroxyimino)methyl)-1,4-dimethylpyridin-1-ium iodide (ADG2078) is provided in FIGS. 71-73.

Example 9

Preparation of 2,6-dimethylpyridine N-oxide (ADG2061) 2,6-Dimethylpyridine N-oxide was synthesized following the literature protocol found at *Chem.-Eur. J.*, 2014, 20, 559-563: A 500-mL pear-shaped flask was charged with 2,6-lutidine (10.7 mL, 100 mmol) at 23° C. under an open atmosphere. Aqueous 0.6 M $K_2CO_3$ (50 mL), t-BuOH (50 mL), MeCN (8.0 mL, 150 mmol. 1.5 equiv), 30% aqueous $H_2O_2$ (60 mL, 500 mmol), and 2,2,2-trifluoroacetophenone (1.4 mL, 10 mmol, 10 mol %) were added sequentially in one portion, and the reaction mixture continued to stir at 23° C. under an open atmosphere for 28 h. After this period, $H_2O$ (50 mL) was added, and the resulting reaction mixture was allowed to stir for 14 h at 23° C. under an open atmosphere. The reaction mixture was extracted with $CH_2Cl_2$ (4×50 mL) using a separatory funnel. The combined organic layers were dried over anhydrous $Na_2SO_4$, filtered, and concentrated in vacuo. The crude residue was purified by flash chromatography (60 to 100% EtOAc in hexanes) on silica gel (200 mL) to afford 2,6-dimethylpyridine N-oxide as a white solid (6.66 g, 54% yield).

Preparation of (6-methylpyridin-2-yl)methanol (ADG2065) A 200-mL pear-shaped flask with 2,6-lutidine N-oxide (2.37 g. 19.3 mmol) was purged with nitrogen gas three times and charged with $CH_2Cl_2$ (25 mL) at 23° C. TFAA (8.14 mL, 57.8 mmol, 3 equiv) in $CH_2Cl_2$ (27 mL) was added, and the resulting reaction mixture was stirred at 23° C. for 42 h. After this period, the reaction mixture was cooled to 0° C. Then, t-BuOH (10 mL) and saturated aqueous $K_2CO_3$ (10 mL) were added to the reaction mixture. The resulting mixture was stirred for 3 h and gradually warmed to 23 CC. The mixture was extracted with $CH_2Cl_2$ (3×50 mL) using a separatory funnel. The combined organic layers were dried over anhydrous $Na_2SO_4$, filtered, and concentrated in vacuo. The resulting crude residue was purified by flash chromatography (50 to 90% EtOAc in hexanes) on silica gel (80 mL) to afford (6-methylpyridin-2-yl)methanol as a dark brown oil (949 mg, 40% yield).

Preparation of 6-methylpicolinaldehyde (ADG2068) A 50-mL pear-shaped flask with a reflux condenser was purged with nitrogen gas three times, and (6-methylpyridin-2-yl)methanol (5.16 mg, 4.16 mmol), DCE (18 mL), and $MnO_2$ (1.91 g, 22.0 mmol, 5 equiv) were added consecutively. The mixture was heated to reflux. After 22 h, the reaction mixture was cooled to 23° C., filtered through Celite®, washed with EtOAc, and concentrated in vacuo. The crude residue was purified by flash chromatography (40 to 70% EtOAc in hexanes) on silica gel (10 mL) to afford 6-methylpicolinaldehyde as a yellow oil (213 mg, 42% yield).

Preparation of (E)-6-methylpicolinaldehyde oxime (ADG2069) A 50-mL pear-shaped flask open to air was charged with 6-methylpicolinaldehyde (309 mg, 2.55 mmol), MeOH (26 mL), $H_2O$ (4 mL), $K_2CO_3$ (423 mg, 3.05 mmol, 1.2 equiv), and $NH_2OH \cdot HCl$ (177 mg, 2.55 mmol, 1 equiv). A reflux condenser was attached, and after the reaction mixture was heated to reflux for 3 h, the reaction mixture was cooled to 23° C. The organic solvent was removed in vacuo, and the resulting aqueous layer was extracted with EtOAc (3×20 mL) using a separatory funnel. The combined organic layers were dried over anhydrous $Na_2SO_4$, filtered, and concentrated in vacuo to afford (E)-6-methylpicolinaldehyde oxime as an ivory solid (177 mg, 52% yield). This material was used directly without further purification.

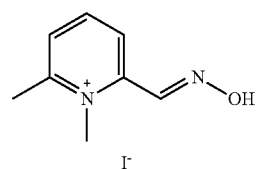

Figure 74:
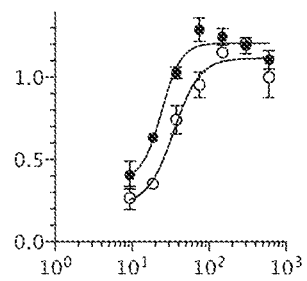
FIG. 74. *Electrophorus electricus* (electric eel) AChE activity of (E)-2-[(hydroxyimino)methyl]-1,6-dimethylpyridin-1-ium (ADG2063) compared to 2-PAM at 20 minutes. $EC_{50}$(ADG2063)=24±1 μM; $EC_{50}$ (2-PAM)=35±1 μM; $EC_{50}$ values are given as mean±SEM. Conditions: 0-600 μM ADG2063, 10 U/mL eel AChE, 200 μM DTNB, 267 μM ATCh, 20 μM paraoxon-methyl, 1:89:10 (v/v) isopropanol: 100 mM phosphate pH 7.4:20 mM Tris pH 7.4.
Figure 75:
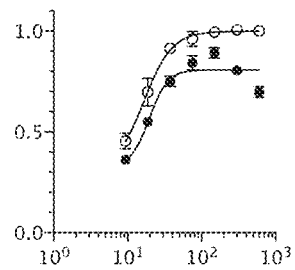
FIG. 75. *Electrophorus electricus* (electric eel) AChE activity of (E)-2-[(hydroxyimino)methyl]-1,6-dimethylpyridin-1-ium (ADG2063) compared to 2-PAM at 20 minutes. EC50(ADG2063)=18±1 μM; EC50 (2-PAM)=16±1 μM; EC50 values are given as mean±SEM. Conditions: 0-600 μM ADG2063, 10 U/mL eel AChE; 200 μM DTNB; 267 μM ATCh; 20 μM paraoxon-ethyl, 1:89:10 (v/v) isopropanol: 100 mM phosphate pH 7.4:20 mM Tris pH 7.4.
Figure 76:
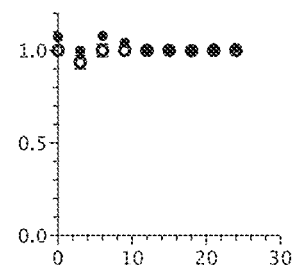
FIG. 76. Inhibition of *Electrophorus electricus* (electric eel) AChE by (E)-2-[(hydroxyimino)methyl]-1,6-dimethylpyridin-1-ium (ADG2063). Conditions: 0 or 600 μM ADG2063, 10 U/mL eel AChE, 200 μM DTNB, 267 μM ATCh, 9:1 (v/v) 100 mM phosphate pH 7.4:20 mM Tris pH 7.4.

Preparation of (E)-2-((hydroxyimino)methyl)-1,6-dimethylpyridin-1-ium Iodide (ADG2063) A 10-mL sealed tube wrapped in aluminum foil with (E)-6-methylpicolinaldehyde oxime (401 mg, 2.94 mmol) was charged with acetone (6 mL) and MeI (1.82 mL, 29.4 mmol, 10 equiv). The reaction mixture was stirred at 23° C. for 3 d. After this period, the reaction mixture was transferred to a 20-mL round-bottomed flask, concentrated in vacuo, and recrystallized from acetone to yield (E)-2-[(hydroxyimino)methyl]-1,6-dimethylpyridin-1-ium as a light brown solid (37.1 mg, 25% yield). In vitro data for (E)-2-((hydroxyimino)methyl)-1,6-dimethylpyridin-1-ium iodide (ADG2063) is provided in FIGS. 74-76

Example 10

Preparation of (4-butoxypyridin-2-yl)methanol (ADG2038) A 200-mL round-bottomed flask was charged with n-butanol (50 mL) and NaH (2.12 g, 53.57 mmol) and stirred at 0° C. under inert atmosphere for 1 h. After, (4-nitropyridin-2-yl)methanol (1.0 g, 6.5 mmol) was added to the stirring reaction mixture. The resulting reaction mixture was refluxed for 20 h. After this period, the reaction mixture was cooled with an ice bath, quenched with saturated aqueous $NH_4Cl$ and concentrated in vacuo. The resulting reside was extracted with EtOAc (3×75 mL), The combined organic layers were dried over anhydrous $Na_2SO_4$, filtered, and concentrated in vacuo. The crude material purified by flash chromatography (60 to 100% EtOAc in hexanes) on silica gel (55 mL) to afford (4-butoxypyridin-2-yl)methanol (599 mg, 51% yield) as a brown oil.

Preparation of 4-butoxypicolinaldehyde (ADG2042) A 100-mL pear-shaped flask with a reflux condenser was purged with nitrogen gas three times, and (4-butoxypyridin-2-yl)methanol (598 mg, 3.29 mmol), DCE (50 mL), and $MnO_2$ (1.15 g, 13.2 mmol, 5 equiv) were added consecutively. The mixture was heated to reflux. After 8 h, the reaction mixture was cooled to 23° C., filtered through Celite®, washed with EtOAc, and concentrated in vacuo to afford 4-butoxypicolinaldehyde as a yellow oil (802 mg, quantitative yield). This material was used directly without further purification.

Preparation of (E)-4-butoxypicolinaldehyde Oxime (ADG2044) A 200-mL pear-shaped flask open to air was charged with 4-butoxypicolinaldehyde (802 mg, 4.47 mmol), MeOH (45 mL), H$_2$O (12 mL), K$_2$CO$_3$ (804 mg, 5.81 mmol, 1.3 equiv), and NH$_2$OH·HCl (311 mg, 4.47 mmol, 1 equiv). A reflux condenser was attached, and after the reaction mixture was heated to reflux for 1.5 h, the reaction mixture was cooled to 23° C. The organic solvent was removed in vacuo, and the resulting aqueous layer was extracted with EtOAc (3×25 mL) using a separatory funnel. The combined organic layers were dried over anhydrous Na$_2$SO$_4$, filtered, and concentrated in vacuo to afford (E)-4-butoxypicolinaldehyde oxime as a light brown solid (492 mg, 57% yield). This material was used directly without further purification.

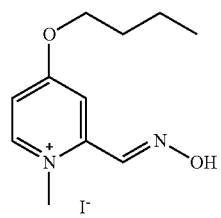

Figure 77:
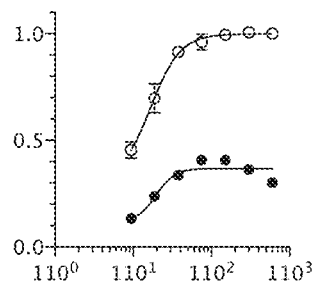
FIG. 77. *Electrophorus electricus* (electric eel) AChE activity of (E)-4-butoxy-2-[(hydroxyimino)methyl]-1-methylpyridin-1-ium iodide (ADG2058) compared to 2-PAM at 25 minutes. EC50(ADG2058)=19±1 μM; EC50 (2-PAM)=16±1 μM; EC50 values are given as mean±SEM. Conditions: 0-600 μM ADG2054, 10 U/mL eel AChE, 200 μM DTNB, 267 μM ATCh, 20 μM paraoxon-ethyl, 1:89:10 (v/v) isopropanol: 100 mM phosphate pH 7.4:20 mM Tris pH 7.4.

Preparation of (E)-4-butoxy-2-[(hydroxyimino)methyl]-1-methylpyridin-1-ium N-methyl Oxime Iodide (ADG2058) A 20-mL sealed tube with (E)-4-butoxypicolinaldehyde oxime (200 mg, 1.03 mmol) was charged with acetone (5 mL) and MeI (256 μL, 4.12 mmol, 4 equiv). The vessel was sealed and heated to 50° C. (external temperature). After 23 h at the same temperature, the reaction mixture was cooled to 23° C., transferred to a 10-mL round-bottomed flask, and concentrated in vacuo to yield (E)-4-butoxy-2-[(hydroxyimino)methyl]-1-methylpyridin-1-ium N-methyl oxime as a dark brown solid (361 mg, quantitative yield). In vitro data for (E)-4-butoxy-2-[(hydroxyimino)methyl]-1-methylpyridin-1-ium iodide (ADG2058) is provided in FIG. 77.

Example 11

Preparation of (4-isopropoxypyridin-2-yl)methanol (ADG2039) A 200-mL round-bottomed flask was charged with isopropanol (50 mL) and NaH (2.12 g, 53.57 mmol) and stirred at 0° C. under inert atmosphere for 1 h. After. (4-nitropyridin-2-yl)methanol (1.0 g, 6.5 mmol) was added to the stirring reaction mixture. The resulting reaction mixture was refluxed for 20 h. After this period, the reaction mixture was cooled with an ice bath, quenched with saturated aqueous NH$_4$Cl and concentrated in vacuo. The resulting reside was extracted with EtOAc (3×75 mL). The combined organic layers were dried over anhydrous Na$_2$SO$_4$, filtered, and concentrated in vacuo. The crude material purified by flash chromatography (60 to 100% EtOAc in hexanes) on silica gel (55 mL) to afford (4-isopropoxypyridin-2-yl)methanol (242 mg, 22% yield) as a brown oil.

Preparation of 4-isopropoxypicolinaldehyde (ADG2043) A 50-mL pear-shaped flask with a reflux condenser was purged with nitrogen gas three times, and (4-isopropoxy pyridin-2-yl)methanol (240 mg, 1.44 mmol), DCE (20 mL), and MnO$_2$ (503 mg, 5.79 mmol, 5 equiv) were added consecutively. The mixture was heated to reflux. After 8 h, the reaction mixture was cooled to 23° C., filtered through Celite®, washed with EtOAc, and concentrated in vacuo to afford 4-isopropoxypicolinaldehyde as an orange oil (148 mg, 62% yield). This material was used directly without further purification.

Preparation of (E)-4-isopropoxypicolinaldehyde Oxime (ADG2053) A 10-mL pear-shaped flask open to air was charged with 4-isopropoxypicolinaldehyde (68.5 mg, 0.414 mmol), MeOH (5 mL), H$_2$O (0.5 mL), K$_2$CO$_3$ (74.2 mg, 0.539 mmol, 1.3 equiv), and NH$_2$OH·HCl (28.7 mg, 0.414 mmol, 1 equiv). A reflux condenser was attached, and after the reaction mixture was heated to reflux for 1.5 h, the reaction mixture was cooled to 23° C. The organic solvent was removed in vacuo, and the resulting aqueous layer was extracted with EtOAc (3×10 mL) using a separatory funnel. The combined organic layers were dried over anhydrous Na$_2$SO$_4$, filtered, and concentrated in vacuo to afford (E)-4-isopropoxypicolinaldehyde oxime as a light brown solid (492 mg, 69% yield). This material was used directly without further purification.

Example 12

Preparation of 2-(dimethoxymethyl)-4-(phenylethynyl)pyridine (ADG2168)

A 500-mL round-bottom flask with 4-bromo-2-(dimethoxymethyl)pyridine (5.0 g, 21.5 mmol) was purged with nitrogen gas three times, treated with Pd(PPh$_3$)$_2$Cl$_2$ (754 mg, 1.08 mmol, 5 mol %) and CuI (204.7 mg, 1.08 mmol, 5 mol %), and then purged again with nitrogen gas three times. The mixture was dissolved in anhydrous 1,4-dioxane (16 mL), Et$_3$N (12.0 mL, 86.0 mmol, 4 equiv), and phenylacetylene (3.54 mL, 32.3 mmol, 1.5 equiv) at 23° C. The resulting solution was heated to 60° C. (external temperature) and stirred. After 17 h, the reaction mixture was cooled to 23° C., and a small amount of charcoal was added. The mixture was filtered by gravity through filter paper and the remaining residue was rinsed with EtOAc. The combined filtrate was concentrated in vacuo and purified by flash chromatography (0 to 50% EtOAc in hexanes) on silica gel (250 mL) to afford 2-(dimethoxymethyl)-4-(phenylethynyl)pyridine (4.76 g, 87% yield) as a dark brown oil.

Preparation of 4-(phenylethynyl)picolinaldehyde (ADG2169)

A 20-mL round-bottomed flask open to air with 2-(dimethoxymethyl)-4-(phenylethynyl)pyridine (1.50 g, 5.92 mmol) was charged with H$_2$O (7 mL) and 5.0 M H$_2$SO$_4$ in H$_2$O (1.40 mL, 7.01 mmol). A reflux condenser was attached, and the solution was heated to reflux 1.5 h. After this period, the reaction mixture was cooled with an ice bath, quenched with saturated aqueous NaHCO$_3$ (10 mL), and extracted with CH$_2$Cl$_2$ (3×20 mL) using a separatory funnel. The combined organic layers were dried over anhydrous Na$_2$SO$_4$, filtered, and concentrated in vacuo to yield 4-(phenylethynyl)picolinaldehyde as a brown oil (1.25 g, 98% yield). This material was used directly without further purification.

Preparation of (E)-4-(phenylethynyl)picolinaldehyde Oxime (ADG2171)

A 50-mL pear-shaped flask open to air was charged with 4-(phenylethynyl)picolinaldehyde (309 mg, 2.55 mmol), MeOH (26 mL), H$_2$O (4 mL), K$_2$CO$_3$ (423 mg, 3.05 mmol), and NH$_2$OH·HCl (77.0 mg, 2.55 mmol, 1 equiv). A reflux condenser was attached, and after the reaction mixture was heated to reflux for 3 h, the reaction mixture was cooled to 23° C. The organic solvent was removed in vacuo, and the resulting aqueous layer was extracted with EtOAc (3×20 mL) using a separatory funnel. The combined organic layers were dried over anhydrous Na$_2$SO$_4$, filtered, and concentrated in vacuo to afford (E)-4-(phenylethynyl)picolinaldehyde oxime as a light brown solid (506 mg, 81% yield). This material was used directly without further purification.

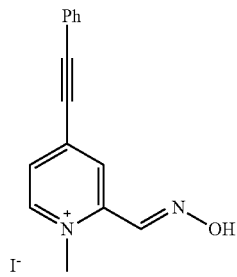 [SMILES: [I-] ; C[n+]1ccc(C#Cc2ccccc2)cc1/C=N/O]

Figure 78:
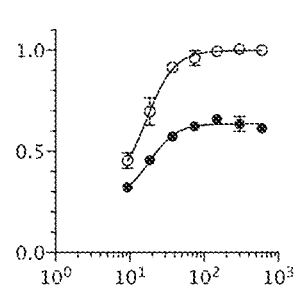
FIG. 78. *Electrophorus electricus* (electric eel) AChE activity of (E)-2-((hydroxyimino)methyl)-1-methyl-4-(phenylethynyl)pyridin-1-ium iodide (ADG2173) compared to 2-PAM at 25 minutes, EC50(ADG2173)=18±1 μM; EC50 (2-PAM)=17±1 μM; EC50 values are given as mean±SEM. Conditions: 0-600 μM ADG2173, 10 U/mL eel AChE, 200 μM DTNB, 267 μM ATCh, 20 μM paraoxon-ethyl, 1:1:88:10 (v/v) isopropanol:DMSO: 100 mM phosphate pH 7.4:20 mM Tris pH 7.4.
Figure 79:
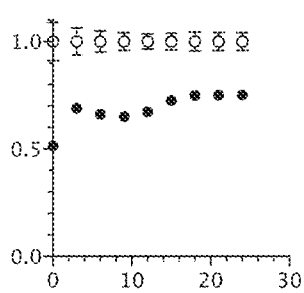
FIG. 79. Inhibition of *Electrophorus electricus* (electric eel) AChE by (E)-2-((hydroxyimino)methyl)-1-methyl-4-(phenylethynyl)pyridin-1-ium iodide (ADG2173). Conditions: 0 or 600 μM ADG2173, 10 U/mL eel AChE, 200 μM DTNB, 267 μM ATCh, 1:89:10 (v/v) DMSO: 100 mM phosphate pH 7.4:20 mM Tris pH 7.4.

Preparation of (E)-2-((hydroxyimino)methyl)-1-methyl-4-(phenylethynyl)pyridin-1-ium Iodide (ADG2173) A 10-mL sealed tube with (E)-4-(phenylethynyl)picolinaldehyde oxime (50 mg, 0.21 mmol) was charged with acetone (700 µL) and MeI (130 µL, 2.11 mmol, 10 equiv). The vessel was sealed and heated to 45° C. (external temperature). After 17 h at the same temperature, the reaction mixture was cooled to 23° C., transferred to a 10-mL round-bottomed flask, and concentrated in vacuo to yield (E)-2-[(hydroxyimino)methyl]-1-methyl-4-(phenylethynyl)pyridin-1-ium as a black solid (52 mg, 67% yield). In vitro data for (E)-2-((hydroxyimino)methyl)-1-methyl-4-(phenylethynyl)pyridin-1-ium iodide (ADG2173) is provided in FIGS. 78 and 79.

Example 13

Preparation of 2-(dimethoxymethyl)-4-phenethylpyridine (ADG2175)

A 200-mL round-bottom flask was charged with ADG2174 (1.27 g, 5.01 mmol), EtOH (84 mL), 5 wt % PVC (195 mg, 50.0 µmol, 1 mol %) at 23° C. The resulting suspension was purged with hydrogen gas three times and stirred vigorously at the same temperature for 17 h. The suspension was filtered by gravity through filter paper, and the resulting filtrate was concentrated in vacuo to yield 2-(dimethoxymethyl)-4-phenethylpyridine as a brown oil (720.0 mg, 56% yield). This material was used directly without further purification.

Preparation of 4-phenethylpicolinaldehyde (ADG2178)

A 10-mL round-bottomed flask open to air with 2-(dimethoxymethyl)-4-phenethylpyridine (477 mg, 1.99 mmol) was charged with H$_2$O (2.3 mL) and 5.0 M H$_2$SO$_4$ in H$_2$O (477 µL, 2.39 mmol). A reflux condenser was attached, and the solution was heated to reflux for 1.5 h. After this period, the reaction mixture was cooled with an ice bath, quenched with saturated aqueous NaHCO$_3$ (5 mL), and extracted with CH$_2$Cl$_2$ (3×20 mL) using a separatory funnel. The combined organic layers were dried over anhydrous Na$_2$SO$_4$, filtered, and concentrated in vacuo to yield 4-phenethylpicolinaldehyde as a brown oil (352.5 mg, 84% yield). This material was used directly without further purification.

Preparation of (E)-4-butoxypicolinaldehyde Oxime (ADG2179) A 50-mL pear-shaped flask open to air was charged with 4-phenethylpicolinaldehyde (200 mg, 0.946 mmol), MeOH (10 mL), H$_2$O (2 mL), K$_2$CO$_3$ (157 mg. 1.13 mmol, 1.2 equiv), and NH$_2$OH·HCl (65.7 mg, 0.946 mmol, 1 equiv). A reflux condenser was attached, and after the reaction mixture was heated to reflux for 2 h, the reaction mixture was cooled to 23° C. The organic solvent was removed in vacuo and the resulting aqueous layer was extracted with EtOAc (3×15 mL) using a separatory funnel. The combined organic layers were dried over anhydrous Na$_2$SO$_4$, filtered, and concentrated in vacuo to afford (E)-4-butoxypicolinaldehyde oxime as a light brown solid (179 mg, 84% yield). This material was used directly without further purification.

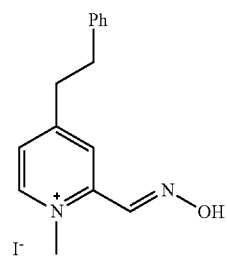 [SMILES: [I-] ; C[n+]1ccc(CCc2ccccc2)cc1/C=N/O]

Figure 80:
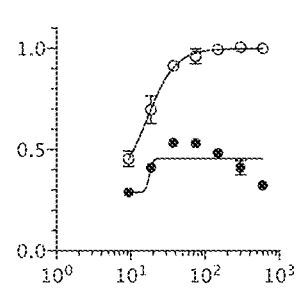
FIG. 80. *Electrophorus electricus* (electric eel) AChE activity of (E)-2-((hydroxyimino)methyl)-1-methyl-4-phenethylpyridin-1-ium N-methyl oxime iodide (ADG2180) compared to 2-PAM at 25 minutes. EC50(ADG2180)=18±1 μM; EC50 (2-PAM)=17±1 μM; EC50 values are given as mean±SEM. Conditions: 0-600 μM ADG2180, 10 U/mL eel AChE, 200 μM DTNB, 267 μM ATCh, 20 μM paraoxon-ethyl, 1:1:88:10 (v/v) isopropanol:DMSO: 100 mM phosphate pH 7.4:20 mM Tris pH 7.4.
Figure 81:
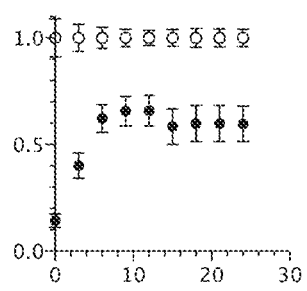
FIG. 81. Inhibition of *Electrophorus electricus* (electric eel) AChE by (E)-2-((hydroxyimino)methyl)-1-methyl-4-phenethylpyridin-1-ium iodide (ADG2180). Conditions: 0 or 600 µM ADG2180, 10 U/mL eel AChE, 200 µM DTNB, 267 µM ATCh, 1:89:10 (v/v) DMSO: 100 mM phosphate pH 7.4:20 mM Tris pH 7.4.

Preparation of (E)-2-((hydroxyimino)methyl)-1-methyl-4-phenethylpyridin-1-ium Iodide (ADG2180) A 10-mL sealed tube with (E)-4-butoxypicolinaldehyde oxime (78 mg, 0.34 mmol) was charged with acetone (1 mL) and MeI (213 µL, 3.44 mmol, 10 equiv). The vessel was sealed and heated to 50° C. (external temperature). After 15 h at the same temperature, the reaction mixture was cooled to 23° C., transferred to a 10-mL round-bottomed flask, and concentrated in vacuo to yield (E)-2-[(hydroxyimino)methyl]-1-methyl-4-phenethylpyridin-1-ium as a brown solid (125 mg, 98% yield). In vitro data for (E)-2-((hydroxyimino)methyl)-1-methyl-4-phenethylpyridin-1-ium iodide: (ADG2180) is provided in FIGS. 80 and 81.

Example 14

Preparation of 4-(trifluoromethyl)picolinaldehyde (JAB5108) A 250-mL three-necked round-bottom flask was charged with Et$_2$O (43 mL) followed by 2-bromo-4-trifluoromethylpyridine (1.00 g, 4.43 mmol). The resulting solution was cooled to −78° C. (internal temperature). 1.6 M n-BuLi (3.79 mL, 5.31 mmol, 1.2 equiv) was added to the solution dropwise over 20 min, keeping the internal temperature below −70° C. The dark red solution was stirred at −78° C. (internal temperature). After 1 h, DMF (512 µL, 6.64 mmol, 1.5 equiv) was added dropwise directly to the resulting solution. The reaction mixture was stirred at −78° C. (internal temperature) for 45 min then allowed to warm to 23° C. and stir for another 1.5 h. Saturated aqueous NH$_4$Cl (30 mL) was added to the reaction mixture and stirred at 23° C. for 30 min. The resulting layers were separated and the aqueous layer was extracted with diethyl ether (20 mL). The organic layers were combined, dried over anhydrous Na$_2$SO$_4$, filtered, and concentrated in vacuo. The crude material was purified by flash chromatography (5 to 20% EtOAc in hexanes) on silica gel (40 mL) to afford 4-(trifluoromethyl)picolinaldehyde (170 mg, 22% yield) as a clear yellow oil.

Preparation of (E)-4-(trifluoromethyl)picolinaldehyde Oxime (JAB5112) A 10-mL round-bottomed flask was charged with 4-(trifluoromethyl)picolonaldeyde (170 mg, 0.971 mmol) followed by MeOH (4.5 mL), H$_2$O (1 mL), K$_2$CO$_3$ (255 mg, 1.84 mmol, 2 equiv), and NH$_2$OH·HCl (81 mg, 1.16 mmol, 1.2 equiv). A reflux condenser was attached to the round bottom flask and the reaction was heated to reflux. After 50 min, the reaction was cooled to 23° C. and concentrated in vacuo. The residue was diluted with EtOAc (20 mL), and the organic layer was washed with brine (10 mL), dried over anhydrous Na$_2$SO$_4$, filtered, and concentrated in vacuo to afford (E)-4-(trifluoromethyl)picolinaldehyde oxime (110 mg, 60% yield) as a white solid which was pure by $^1$H NMR.

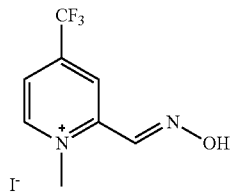

Figure 82:
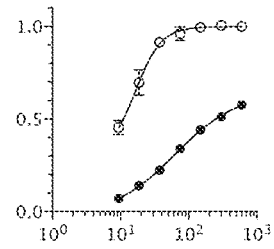
FIG. 82. *Electrophorus electricus* (electric eel) AChE activity (E)-4-(trifluoromethyl)-2-((hydroxyimino)methyl)-1-methylpyridin-1-ium iodide (JAB5117) compared to 2-PAM at 25 minutes. EC50(JAB5117)=18±1 µM; EC50 (2-PAM)=17±1 µM; EC50 values are given as mean±SEM. Conditions: 0-600 µM JAB5117, 10 U/mL eel AChE, 200 µM DTNB, 267 µM ATCh, 20 µM paraoxon-ethyl, 1:1:88:10 (v/v) isopropanol:DMSO: 100 mM phosphate pH 7.4:20 mM Tris pH 7.4.

Preparation of (E)-4-(trifluoromethyl)-2-((hydroxyimino)methyl)-1-methylpyridin-1-ium Iodide (JAB5117) A 5-mL sealed-tube flask was charged with (E)-4-(trifluoromethyl)picolinaldehyde oxime (100 mg, 526 µmol) dissolved in acetone (500 µL) and MeI (1.00 mL, 16.1 mmol, 31 equiv). The vessel was sealed and heated to 85° C. (external temperature) for 17 h. The reaction mixture was cooled to 23° C. and concentrated in vacuo. The residue was triturated with EtOAc (5 mL), filtered, and dried under high vacuum to give (E)-4-(trifluoromethyl)-2-((hydroxyimino)methyl)-1-methylpyridin-1-ium iodide (49 mg, 28% yield) as a yellow solid. In vitro data for (E)-4-(trifluoromethyl)-2-((hydroxyimino)methyl)-1-methylpyridin-1-ium iodide (JAB5117) is provided in FIG. 82.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

What is claimed is:

1. A compound having the structure:

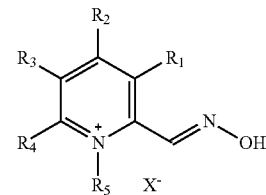

wherein:
R$_1$ and R$_3$ are H;
R$_4$ is H or methyl;
R$_2$ is H; methyl; phenyl, halomethyl;

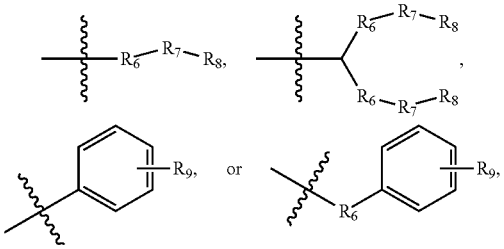

wherein each instance of R$_6$ is, independently, C, O, S, N, carbonyl, sulfinyl, or sulfonyl, each instance of R$_7$ is, independently, a C$_1$-C$_4$ saturated alkane, each instance of R$_8$ is, independently, H, hydroxyl, halo, halomethyl, phenyl, C$_1$-C$_4$ alkoxyl, amine, carboxyl, N(C$_1$-C$_4$ alkyl)$_2$, NH(C$_1$-C$_4$ alkyl), or azide, and R$_9$ is H, halo, methoxyl, methyl; prop-2-yn-1-yloxyl; 4-hydroxybut-1-yn-1-yl; 3-hydroxyprop-1-yn-1-yl; or phenylethynyl;
R$_5$ is methyl or 3-hydroxypropyl (—CH$_2$CH$_2$CH$_2$OH); and
X$^-$ is a counterion,
wherein when R$_2$ is H, R$_4$ is methyl, or
wherein when R$_2$ and R$_4$ are H, R$_5$ is 3-hydroxypropyl (—CH$_2$CH$_2$CH$_2$OH).

2. The compound of claim 1 having the structure:

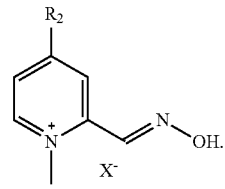

3. The compound of claim 2, wherein:
R$_1$, R$_3$, and R$_4$ are H and R$_2$ is hydroxypropyl; hydroxybutyl; C$_1$-C$_4$ alkyloxy; propynyloxy; 3-hydroxy-3-methylbutyl; phenyl; ethyl-substituted phenyl; phenylethyl; phenylethynyl; C$_1$-C$_3$ saturated or unsaturated alkyl; —CF$_3$; 2,2,2-trifluoro ethoxy; ethylthio; or ethylamino; or
one of R$_1$, R$_2$, R$_3$, and R$_4$ is methyl and the others of R$_1$, R$_2$, R$_3$, and R$_4$ are H,
and X is a pharmaceutically-acceptable anion.

4. The compound of claim 2, wherein R$_2$ is methyl, phenyl, phenylethyl, trifluoromethyl, 3-hydroxypropyl, 4-hydroxybutyl, 3-hydroxy-3-methylbutyl, ethoxyl, butoxyl, isopropoxyl, 2,2,2-trifluoroethoxyl, prop-2-yn-1-yloxyl, phenylethynyl, ethylthio, ethylamino.

5. The compound of claim 1, wherein: R$_1$, R$_3$, and R$_4$ are H and R$_2$ is methyl, propyl, butyl, phenyl, 2-methoxyphenyl, 3-methoxyphenyl, 4-methoxyphenyl, 4-methoxybutyl, 4-fluorobutyl, 2-fluorophenyl, 3-fluorophenyl, 4-fluorophenyl, ethoxyl, propoxyl, isopropoxyl, butoxyl, phenoxyl, o-tolyloxyl, m-tolyloxyl, p-tolyloxyl, 2-hydroxyethoxyl, 2-fluorophenoxyl, 3-fluorophenoxyl, 4-fluorophenoxyl, 2-methoxyphenoxyl, 3-methoxyphenoxyl, 4-methoxyphenoxyl, prop-2-yn-1-yloxy, 2,2,2-trifluoroethoxyl, ethylthio, propylthio, isopropylthio, butylthio, tert-butylthio, phenylthio, 3-hydroxypropyl, 4-hydroxybutyl, 3-hydroxy-3-methylbutyl, ethylamino, or 4-hydroxybut-1-yn-1-yl.

6. The compound of claim 1, chosen from (E)-4-butoxy-2-[(hydroxyimino)methyl]-1-methylpyridin-1-ium iodide (ADG2058), (E)-2-((hydroxyimino)methyl)-1,6-dimethylpyridin-1-ium iodide (ADG2063), (E)-2-[(hydroxyimino)methyl]-1,4-dimethylpyridin-1-ium (ADG2078), (E)-2-((hydroxyimino)methyl)-1-methyl-4-(phenylethynyl)pyridin-1-ium iodide (ADG2173), (E)-2-((hydroxyimino)methyl)-1-methyl-4-phenethylpyridin-1-ium N-methyl oxime iodide (ADG2180), (E)-2-((hydroxyimino)methyl)-1-methyl-4-(propylthio)pyridin-1-ium iodide (ADG2293), (E)-4-(butylthio)-2-((hydroxyimino)methyl)-1-methylpyridin-1-ium iodide (ADG2294), (E)-4-(tert-butylthio)-2-((hydroxyimino)methyl)-1-methylpyridin-1-ium iodide (ADG3001), (E)-2-((hydroxyimino)methyl)-1-methyl-4-(phenylthio)pyridine-1-ium iodide (ADG3002), (E)-2-((hydroxyimino)methyl)-1-methyl-4-phenoxypyridin-1-ium iodide (ADG3003), (E)-(hydroxyimino)methyl)-1-methyl-4-propoxypyridin-1-ium iodide (ADG3035), (E)-2-((hydroxyimino)methyl)-4-(isopropylthio)-1-methylpyridin-1-ium iodide (ADG3060), (E)-2-((hydroxyimino)methyl)-1-methyl-4-(p-tolyloxy)pyridine-1-ium iodide (ADG3092), (E)-2-((hydroxyimino)methyl)-1-methyl-4-(o-tolyloxy)pyridine-1-ium iodide (ADG3110), (E)-2-((hydroxyimino)methyl)-1-methyl-4-(m-tolyloxy)pyridine-1-ium iodide (ADG3111), (E)-2-((hydroxyimino)methyl)-1-methyl-4-(4-fluorophenoxy)pyridin-1-ium iodide (ADG3116), (E)-2-((hydroxyimino)methyl)-1-methyl-4-(2-methoxyphenoxy)pyridin-1-ium iodide (ADG3120), (E)-2-((hydroxyimino)methyl)-1-methyl-4-(4-methoxyphenoxy)pyrdin-1-ium iodide (ADG3121), (E)-2-((hydroxyimino)methyl)-1-4-(3-fluorophenoxy)pyridin-1-ium iodide (ADG3123),

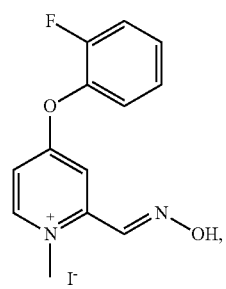

(ADG3124)

(E)-2-((hydroxyimino)methyl)-1-methyl-4-(3-methoxyphenoxy)pyrdin-1-ium iodide (ADG3128), (E)-2-((hydroxyimino)methyl)-4-(3-hydroxypropyl)-1-methylpyridin-1-ium iodide (RKB6186), (E)-2-((hydroxyimino)methyl)-1-methyl-4-(2,2,2-trifluoroethoxy)pyridin-1-ium iodide (RKB6220), (E)-4-ethoxy-2-((hydroxyimino)methyl)-1-methylpyridin-1-ium iodide (RKB6229), (E)-2-((hydroxyimino)methyl)-1-methyl-4-phenylpyridin-1-ium (RKB6242), (E)-4-(4-hydroxybutyl)-2-((hydroxyimino)methyl)-1-methylpyridin-1-ium iodide (RKB6259), (E)-2-((hydroxyimino)methyl)-1-methyl-4-(prop-2-yn-1-yloxy)pyridin-1-ium iodide (RKB6284), (E)-4-(ethylthio)-2-((hydroxyimino)methyl)-1-methylpyridin-1-ium iodide (RKB7070), (E)-4-(4-fluorophenyl)-2-((hydroxyimino)methyl)-1-methylpyridin-1-ium iodide (RKB8122), (E)-2-((hydroxyimino)methyl)-4-(4-methoxybutyl)-1-methylpyridin-1-ium iodide (RKB8160),

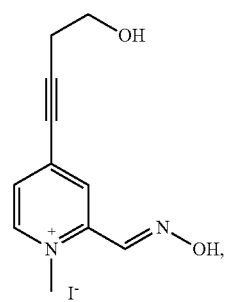

(RKB8162)

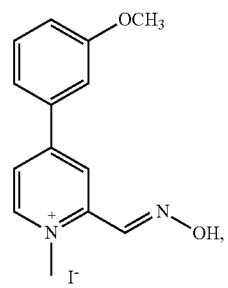

(RKB8189)

-continued

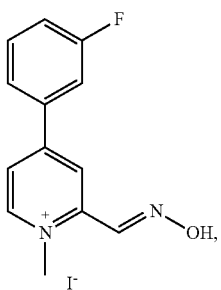
(RKB8191)

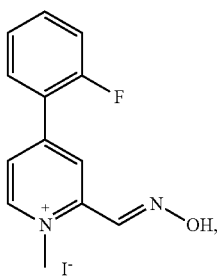
(RKB8217)

(E)-2-((hydroxyimino)methyl)-4-(2-methoxyphenyl)-1-methylpyridin-1-ium iodide (RKB8218), (E)-4-butyl-2-((hydroxyimino)methyl)-1-methylpyridin-1-ium iodide (RKB8274), (E)-4-(trifluoromethyl)-2-((hydroxyimino)methyl)-1-methylpyridin-1-ium iodide (JAB5117),

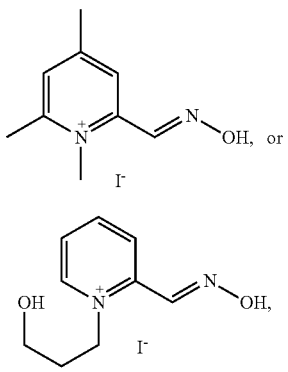
(JAB6073)

(JAB6123)

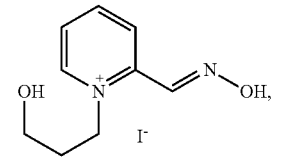

or a pharmaceutically-acceptable salt of any of the preceding.

7. The compound of claim 1, wherein $R_5$ is 3-hydroxypropyl and $R_1$, $R_2$, $R_3$, and $R_4$ are H.

8. The compound of claim 1, wherein X is I⁻ or Cl⁻.

9. The compound of claim 1, wherein $R_2$ is 3-hydroxypropyl and $R_1$, $R_3$, and $R_4$ are H, and where X is optionally Cl⁻ or I⁻.

10. The compound of claim 1, wherein $R_2$ is 3-hydroxybutyl and $R_1$, $R_3$, and $R_4$ are H, and where X is optionally Cl⁻ or I⁻.

11. A composition comprising a compound as claimed in claim 1, and a pharmaceutically-acceptable carrier.

12. The composition of claim 11, further comprising a pharmaceutically effective amount of a muscarinic acetylcholine receptor antagonist or a benzodiazepine.

* * * * *

UNITED STATES PATENT AND TRADEMARK OFFICE
CERTIFICATE OF CORRECTION

PATENT NO. : 12,065,409 B2
APPLICATION NO. : 17/058429
DATED : August 20, 2024
INVENTOR(S) : Kazunori Koide et al.

Page 1 of 1

It is certified that error appears in the above-identified patent and that said Letters Patent is hereby corrected as shown below:

In the Claims

Column 33, Lines 50-51, Claim 6, delete "(E)-(hydroxyimino) methyl)-1-methyl-4-propoxypyridin-1-ium iodide (ADG3035)," and insert -- "(E)-((hydroxyimino) methyl)-1-methyl-4-propoxypyridin-1-ium iodide (ADG3035)," --

Signed and Sealed this
Twenty-sixth Day of November, 2024

Katherine Kelly Vidal
*Director of the United States Patent and Trademark Office*